United States Patent
Oosting et al.

(10) Patent No.: US 9,527,798 B2
(45) Date of Patent: Dec. 27, 2016

(54) CYCLOPROPYLBORONIC COMPOUNDS, PREPARATION PROCESS THEREOF AND USE THEREOF

(71) Applicant: DIVERCHIM, Roissy en France (FR)

(72) Inventors: Peter Oosting, Ivry sur Seine (FR); Emmanuel Thomas, Paris (FR); Rukiye Pamuk, Rully (FR); Benoit Folleas, Senlis (FR); Jean-Louis Brayer, Nanteuil le Haudouin (FR); Benoit De Carne Carnavalet, Paris (FR); Christophe Meyer, Roissy en France (FR); Janine Cossy, Roissy en France (FR)

(73) Assignee: DIVERCHIM, Roissy en France (FR)

( * ) Notice: Subject to any disclaimer, the term of this patent is extended or adjusted under 35 U.S.C. 154(b) by 0 days.

(21) Appl. No.: 14/651,832

(22) PCT Filed: Dec. 12, 2013

(86) PCT No.: PCT/FR2013/053057
§ 371 (c)(1),
(2) Date: Jun. 12, 2015

(87) PCT Pub. No.: WO2014/091167
PCT Pub. Date: Jun. 19, 2014

(65) Prior Publication Data
US 2015/0329566 A1    Nov. 19, 2015

(30) Foreign Application Priority Data

Dec. 12, 2012 (FR) .................... 12 61973

(51) Int. Cl.
| | | |
|---|---|---|
| C07C 67/343 | (2006.01) |
| C07C 69/743 | (2006.01) |
| C07F 5/02 | (2006.01) |
| C07D 333/24 | (2006.01) |
| C07D 307/54 | (2006.01) |
| C07D 213/85 | (2006.01) |
| C07D 215/14 | (2006.01) |
| C07D 217/16 | (2006.01) |
| C07D 317/46 | (2006.01) |
| C07C 69/753 | (2006.01) |
| C07C 69/757 | (2006.01) |
| C07D 231/12 | (2006.01) |
| C07D 333/16 | (2006.01) |
| C07D 239/26 | (2006.01) |
| C07D 213/55 | (2006.01) |
| C07D 213/61 | (2006.01) |
| C07D 307/46 | (2006.01) |
| C07D 307/79 | (2006.01) |
| C07C 41/30 | (2006.01) |
| C07C 269/06 | (2006.01) |

(52) U.S. Cl.
CPC ............ *C07C 67/343* (2013.01); *C07C 41/30* (2013.01); *C07C 69/743* (2013.01); *C07C 69/753* (2013.01); *C07C 69/757* (2013.01); *C07C 269/06* (2013.01); *C07D 213/55* (2013.01); *C07D 213/61* (2013.01); *C07D 213/85* (2013.01); *C07D 215/14* (2013.01); *C07D 217/16* (2013.01); *C07D 231/12* (2013.01); *C07D 239/26* (2013.01); *C07D 307/46* (2013.01); *C07D 307/54* (2013.01); *C07D 307/79* (2013.01); *C07D 317/46* (2013.01); *C07D 333/16* (2013.01); *C07D 333/24* (2013.01); *C07F 5/02* (2013.01); *C07F 5/025* (2013.01); *C07B 2200/09* (2013.01); *C07C 2102/02* (2013.01)

(58) Field of Classification Search
CPC .......................... C07C 67/343; C07C 69/743
See application file for complete search history.

(56) References Cited

U.S. PATENT DOCUMENTS

2009/0203750 A1    8/2009    Kozikowski et al.

FOREIGN PATENT DOCUMENTS

WO    2007-025144    3/2007

OTHER PUBLICATIONS

French search report, dated Sep. 11, 2013; Application No. FR 1261973.
International search report, dated Jun. 4, 2014; Application No. PCT/FR2013/053057.
Fontani et al., "Synthesis of Cyclopropylboronic Acid Esters by Carbene Transfer to 1-Alkenylboronic Acid Esters," Synthesis, vol. 1991. No. 8, Jan. 1, 1991, pp. 605-609.
Hohn et al., "Synthesis of Enantiomerically Pure Cyclopropyl Trifluoroborates," Synlett, vol. 2006, No. 10, Jun. 12, 2006, pp. 1531-1534.
Pietruszka et al., "Enantiomerically Pure Cyclopropylboronic Esters," European Journal of Organic Chemistry, vol. 2009, No. 34, Dec. 1, 2009, pp. 5998-6008.
Vaultier et al., "Product subclass 28: Vinylboranes," Science of Synthesis, Dec. 23, 2004, pp. 721-853.

*Primary Examiner* — Golam M M Shameem
(74) *Attorney, Agent, or Firm* — Young & Thompson

(57) ABSTRACT

Cyclopropylboronic compounds, the preparation process thereof and the use thereof.

7 Claims, No Drawings

CYCLOPROPYLBORONIC COMPOUNDS, PREPARATION PROCESS THEREOF AND USE THEREOF

A subject of the present invention is cyclopropylboronic compounds, the preparation process thereof and the use thereof.

The cyclopropane unit is present in numerous natural products (terpenes, steroids, polycetides, pheromones, metabolites of fatty acids, unusual amino acids) having very varied biological activities (antibiotic, antiviral, antifungal, antitumour, neuromediator, insecticide, regulation of plant growth, ripening of fruit).

Chrysanthemic acid and the pyrethrins, insecticides isolated from the flower *Chrysanthemum cinerariaefolium*, can be mentioned as examples of natural bioactive cyclopropanes:

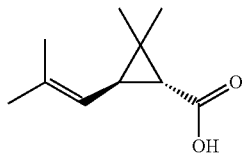

Chrysanthemic acid

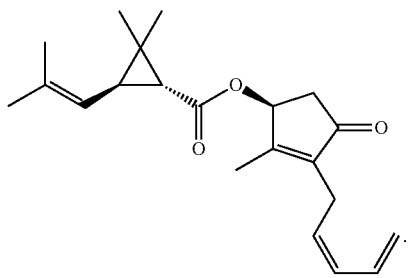

Pyrethrin I

The electronic and steric properties of cyclopropane, in particular its conformational rigidity which makes it possible to orientate the functional groups in space in a perfectly defined manner, make it a structural unit that is particularly important and useful in medicinal chemistry.

The cyclopropane unit, in particular substituted by a heteroatom (nitrogen or oxygen) is found in numerous medicinal products currently on the market, and candidate medicinal products in development, for example Tranylcypromine, Trovafloxacin, Tasimelteon and anti-virals against hepatitis C, in particular MR 200 (*J. Med. Chem.* 2011, 54(10), 3669), Simeprevir, Danoprevir, Asunaprevir, MK 5172, Sovaprevir and Vanipevir.

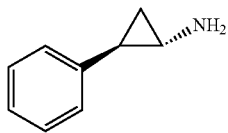

Tranylcypromine

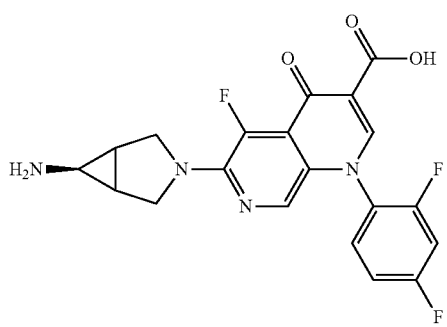

Trovafloxacin

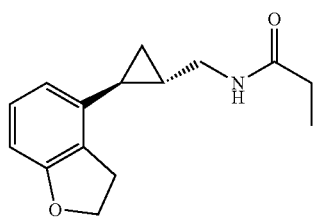

Tasimelteon

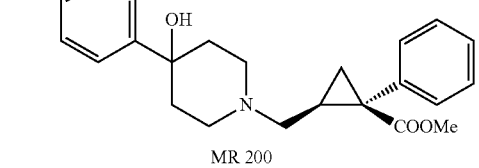

MR 200

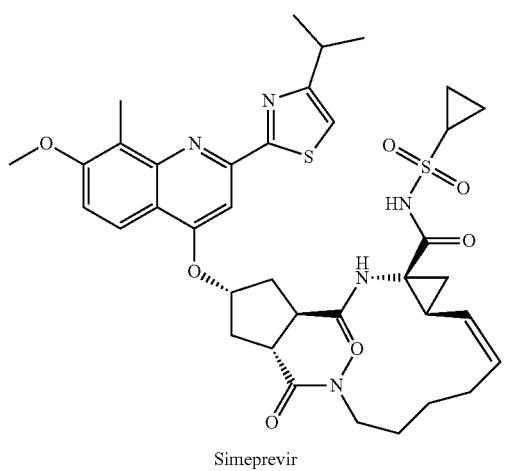

Simeprevir

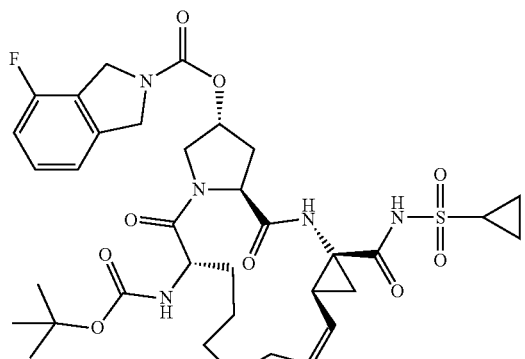

Danoprevir

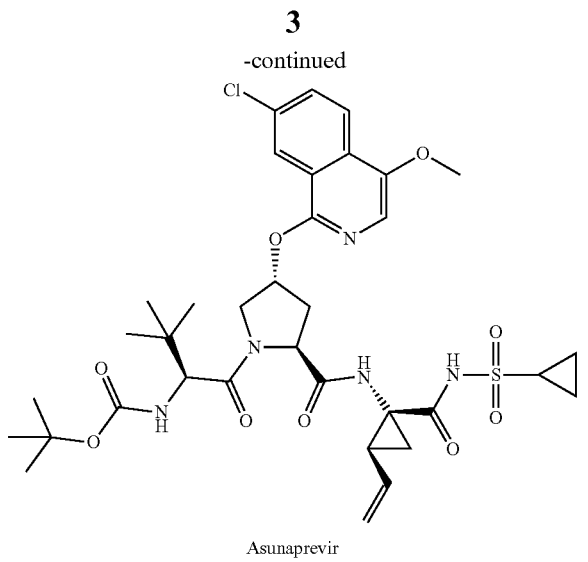

Asunaprevir

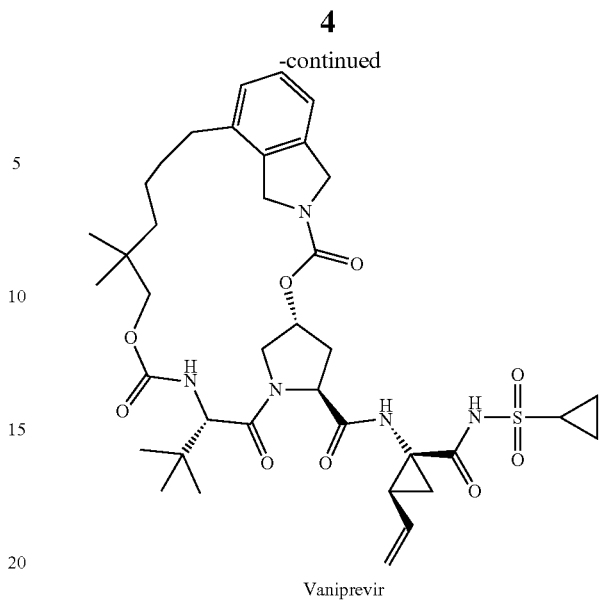

Vaniprevir

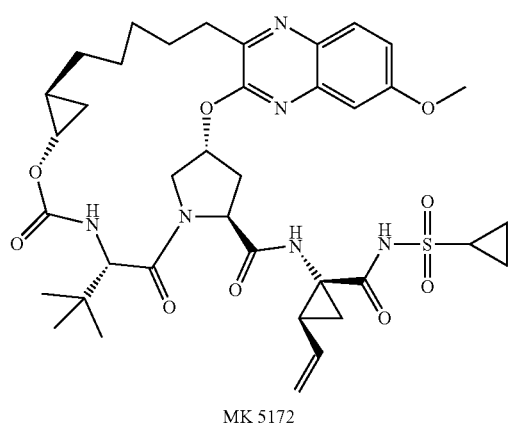

MK 5172

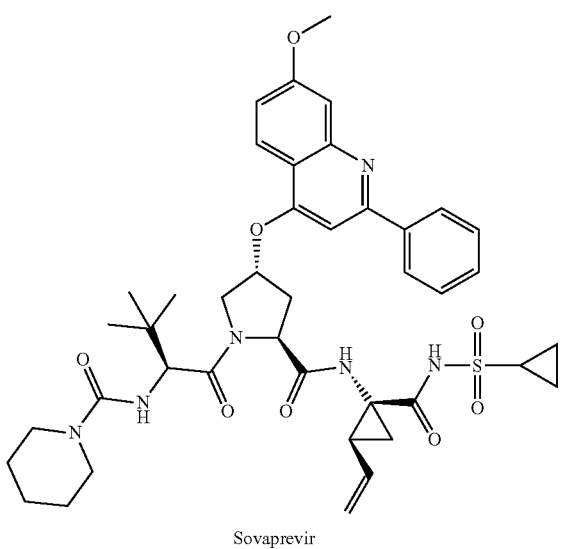

Sovaprevir

The cyclopropanic compounds also constitute important intermediates in organic synthesis. According to the nature of the substituents and their electronic properties, the ring with three members can be opened by thermal, photochemical reactions, promoted by electrophiles, nucleophiles, radicals or catalyzed by organometallic complexes, the motive force of which is the release of the ring strain.

In view of the importance of this structural element, numerous syntheses of cyclopropanes have been published. The majority of the reactions forming a cyclopropyl ring involve on the Simmons-Smith reaction, the Corey-Chaikovski reaction or the addition of a carbene formed from a diazoic compound.

However, these reactions do not allow the direct and convergent introduction of a cyclopropyl unit onto a molecule of interest.

Within the context of organometallic couplings, the organotrifluoroborates have numerous advantages as reagents compared to the boronic acids and the esters of said acids: said organotrifluoroborates are tetravalent "ate" complexes having exceptional stability in air, humidity the nucleophilic compounds. The vast majority can be stored indefinitely at ambient temperature without specific precautions. Finally, despite this stability, the organotrifluoroborate derivatives have a very high reactivity over a wide range of reactions and particularly the organometallic couplings catalyzed by a transition metal.

Thus, one of the objectives of the present invention consists of providing functionalized cyclopropyl trifluoroborate compounds.

Another objective of the invention consists of preparing said compounds by a simple and rapid process.

Another objective of the invention is the use of said functionalized cyclopropyl trifluoroborate compounds in an organometallic coupling reaction catalyzed by a transition metal in order to introduce a functionalized cyclopropyl unit into a molecule of interest.

As a result, a subject of the invention is a process for the preparation of a compound corresponding to the following formula (I):

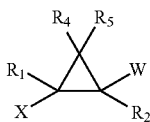
(I)

in which:

X represents a substituted boron atom chosen from the group comprising $B(OH)_2$, $B(OR)_2$, $BF_3M$, $B(OR')_3M$ in which:

R is an alkyl group comprising 1 to 14 carbon atoms or an aryl group, optionally substituted, or is such that $(OR)_2$ forms a ring between the two oxygen atoms, $(OR)_2$ being in particular chosen from the group comprising the bivalent radicals deriving from diols, such as O—$CH_2$—$CH_2$—O, O—$CH_2$—$CH_2$—$CH_2$—O, O—$CH_2$—$C(CH_3)_2$—$CH_2$—O, O—$C(CH_3)_2$—$CH_2$—$CH_2$—$C(CH_3)_2$—O, O—$CH(CH_3)$—$CH_2$—$CH_2$—$CH(CH_3)$—O, O—CH(Ph)-CH(Ph)-O, O—$CH(CH_3)$—$CH_2$—$C(CH_3)_2$—O, O-o-Ph-O, O—$CH_2$—$CH_2$—NH—$CH_2$—$CH_2$—O, O—$CH_2$—$CH_2$—$N(CH_2$—$CH_2$—$CH_3)$—$CH_2$—$CH_2$—O, O—CH(COOH)—CH(COOH)—O and its esters, and the bivalent radicals deriving from diacids, such as OCO—$CH_2$—$N(CH_3)$—$CH_2$—COO, R' is an alkyl group comprising 1 to 14 carbon atoms or is such that:
 $(OR')_3$ forms a ring between two of the oxygen atoms, $(OR')_3$ then being in the form $OR'(OR)_2$, where R' is an alkyl group comprising 1 to 14 carbon atoms and $(OR)_2$ is as defined above, or
 $(OR')_3$ forms a bicycle between the three oxygen atoms, $(OR')_3$ being in particular chosen from the group comprising the trivalent radicals deriving from triols, such as $H_3C$—C—$(CH_2$—$O)_3$, M represents the lithium $Li^+$ ion, the sodium $Na^+$ ion, the potassium $K^+$ ion, the caesium $Cs^+$ ion, the ammonium $R^cR^dR^eR^fN^+$ ion where $R^c$, $R^d$, $R^e$, $R^f$ are chosen from H or a saturated carbon-containing chain comprising in particular 1 to 6 carbon atoms chosen independently of one another, and in particular X represents $B(OH)_2$, $B(OR)_2$ or $BF_3K$, $R_1$, $R_4$ and $R_5$, identical or different, are chosen from the group constituted by:
1. H
2. the aryls comprising rings with 6 to 15 carbon atoms, optionally substituted;
3. the heterocycles or heteroaryls comprising rings with 2 to 15 carbon atoms, optionally substituted;
4. the linear or branched alkenyls comprising 1 to 12 carbon atoms, optionally substituted, or carbon rings comprising 3 to 12 carbon atoms and one or more C=C double bonds, optionally substituted;
5. the linear or branched alkynyls comprising 1 to 15 carbon atoms, optionally substituted;
6. the linear, cyclic or branched alkyl groups comprising 1 to 15 carbon atoms, optionally substituted;

$R_1$ and $R_4$, or $R_1$ and $R_5$ being able to form a ring with 5, 6, or 7 members optionally comprising a heteroatom chosen from oxygen, nitrogen and sulphur, said ring being able to be substituted;

$R_2$ is chosen from the group constituted by the groups being able to be represented by $R_1$, $R_4$ or $R_5$, as well as —$COR^a$, —$COOR^a$, —$CONH_2$, —$CONHR^a$, —$CONR^aR^b$, —CN and —$NO_2$, in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;

$R^a$ and $R^b$ being able to be linked in order to form a ring, optionally substituted, W represents a functional group chosen from —CHO, —$COR^a$, —COOH, —$COOR^a$, —$CONH_2$, —$CONHR^a$, —$CONR^aR^b$, —CONH—$SO_2$—$R^a$, —$CH_2OH$, —$CH_2OR^a$, —$CHR^bOH$, —$CHR^bOR^a$, —$CR^bR^{b'}OH$, —$CR^bR^{b'}OR^a$, —$CH_2NH_2$, —$CH_2NHZ$, —$CHR^aNHZ$, —$CH_2$—NH—COR', —OH, —$OR^a$, —OZ', —$NH_2$, —$NHR^a$, —$NR^aR^b$, —NHZ and —$NZZ_2$, in which Z and $Z_2$ represent a protective group of an amine function, and Z' represents a protective group of an alcohol function, and in which $R^a$, $R^b$ and $R^{b'}$, identical or different, represent linear, cyclic or branched, aromatic, or aromatic or non-aromatic heterocyclic alkyl, alkenyl, alkynyl groups comprising 1 to 15 carbon atoms, optionally substituted;

when W represents a functional group chosen from —CHO, —$COR^a$, —COOH, —$COOR^a$, —$CONH_2$, —$CONHR^a$, —$CONR^aR^b$, —$CH_2OH$, —$CH_2OR^a$, —$CHR^bOH$, —$CHR^bOR^a$, —$CR^bR^{b'}H$, —$CR^bR^{b'}OR^a$, —$CH_2NH_2$, —$CH_2NHZ$, —$CHR^aNHZ$, said process comprising:

a step of reaction between:
a diazoic derivative of the following formula:

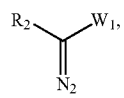

in which $R_2$ is as defined above, $W_1$ being chosen from the group constituted by —$COR^a$, —$COOR^a$, —$CONH_2$, —$CONHR^a$, and —$CONR^aR^b$, and a vinyltrifluoroborate compound of the following formula:

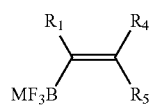

in which $R_1$, $R_4$, $R_5$ and M are as defined above, in the presence of a catalyst containing a transition metal, in order to obtain a compound of the following formula:

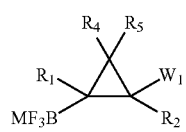

in which $R_1$, $R_2$, $R_4$, $R_5$, $W_1$ and M are as defined above, if W is different from $W_1$ and/or X is different from $MF_3B$, said process also comprising the following steps:

a step of conversion of $W_1$ to W making it possible to obtain

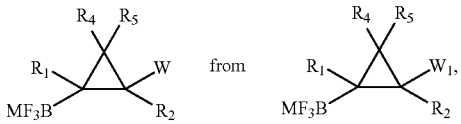

in particular, when $W_1$=COOR$^a$ and W=CHO, by reduction in order to form the corresponding alcohol, then oxidation of said alcohol, when $W_1$=—COOR$^a$ and W=CH$_2$OH or —CH$_2$OR$^b$, by the formation of an aldehyde as described previously, then by reduction of said aldehyde and optional alkylation, when $W_1$=—COR$^a$ and W=—CHR$^a$OH, —CHR$^a$OR$^b$, by reduction then optional alkylation of the alcohol obtained, when $W_1$=—COR$^a$ and W=CR$^a$R$^b$OH or —CR$^a$R$^b$OR$^{b'}$ by addition of a Grignard reagent then optional alkylation of the alcohol obtained, when $W_1$=—CONH$_2$, —CONHR$^a$ or —CONR$^a$R$^b$ and W=—CH$_2$NH$_2$, —CH$_2$NHR$^a$, —CH$_2$NR$^a$R$^b$, —CH$_2$NHZ or —CH$_2$—NH—COR$^a$, by reduction then optional protection by Z of the amine obtained or optional reaction with the acid chloride R$^a$COCl, when $W_1$=—CONH$_2$ and W=—CONHSO$_2$R$^a$, by the action of sulphonyl chloride ClSO$_2$R$^a$ on the amide, and
a step of conversion of —BF$_3$M to —X making it possible to obtain

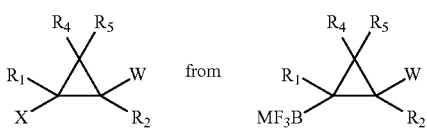

in particular, when X=B(OH)$_2$, by basic or acid hydrolysis, or by passing via a dihalogenoborane, more particularly a dichloroborane, when X=B(OR)$_2$, by passing via X=B(OH)$_2$ as described previously then by the action of an alcohol, in particular an alcohol of formula ROH, a diol or a triol, or by passing via a dihalogenoborane, more particularly a dichloroborane, then by the action of an alcohol, in particular an alcohol of formula ROH, a diol or a triol, or
a step of conversion of —BF$_3$M to —X making it possible to obtain

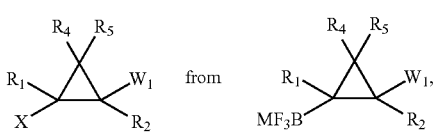

and
a step of conversion of $W_1$ to W making it possible to obtain

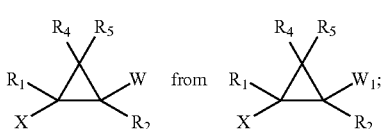

when W represents a functional group chosen from —OH, —OR$^a$, —OZ', —NH$_2$, —NHR$^a$, —NR$^a$R$^b$, —NHZ and —NZZ$_2$, in particular from —OH, —OR$^a$ and —OZ', said process comprising:

the treatment of a compound of the following formula:

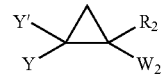

in which $R_2$ is as defined above,
and in which $W_2$ represents a functional group chosen from —OR$^a$, —OZ', —NR$^a$R$^b$ and —NZZ$_2$, in particular from —OR$^a$ and —OZ', Y being a halide, in particular —Br, Y' being a halide, in particular —Br, or H, by:
a strong base, in particular an alkyl lithium, more particularly n-butyllithium or sec-butyllithium, then
a compound of formula X"—B(OR)$_2$, R being as defined above, X" representing H, an O-alkyl group comprising 1 to 14 carbon atoms or an O-aryl group, optionally substituted,
in order to obtain a compound of the following formula:

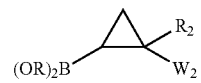

in which R, $R_2$ and $W_2$ are as defined above,
or
a reaction of the Simmons-Smith type starting from a compound of the following formula:

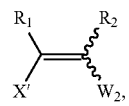

in which $R_1$ and $R_2$ are as defined previously, $W_2$ representing a functional group chosen from —OR$^a$, —OZ', —NR$^a$R$^b$ and —NZZ$_2$, in particular from —OR$^a$ and —OZ', X' representing B(OR)$_2$ or BF$_3$M, in particular B(OR)$_2$, in which R and M are as defined previously,
in order to obtain a compound of the following formula:

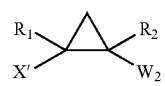

in which $R_1$, $R_2$, X' and $W_2$ are as defined above,
if W represents —OH or —NH$_2$, and/or X is different from B(OR)$_2$, said process also comprising the following steps, $R_1$ representing in particular H:
a step of conversion of $W_2$ to W, in particular the deprotection of the Z' group when $W_2$ represents —OZ' and of the Z and $Z_2$ groups when $W_2$ represents —NZZ$_2$, making it possible to obtain

and a step of conversion of B(OR)$_2$ to —X making it possible to obtain

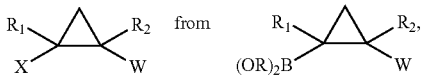

said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$, or a step of conversion of B(OR)$_2$ to —X making it possible to obtain

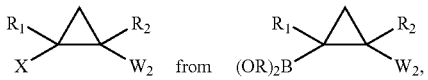

said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$, and a step of conversion of W$_2$ to W, in particular the deprotection of the Z' group when W$_2$ represents —OZ' and of the Z and Z$_2$ groups when W$_2$ represents —NZZ$_2$, making it possible to obtain

or, when X' represents BF$_3$M, W representing —OH or —NH$_2$, a step of conversion of W$_2$ to W, in particular the deprotection of the Z' group when W$_2$ represents —OZ' or of the Z and Z$_2$ groups when W$_2$ represents —NZZ$_2$, making it possible to obtain

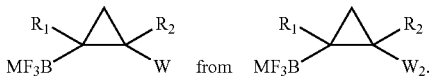

In the above and hereafter, in particular with respect to the aryls, the heterocycles, the heteroaryls, the alkenyls, the alkynyls, the alkyls, the rings optionally formed by R$_1$ and R$_4$, or R$_1$ and R$_5$, and the R$^a$, R$^b$ and R$^{b'}$ groups, by substituted is meant the fact of being substituted by:

one or more halogen atoms comprising fluorine, chlorine, bromine or iodine, hydroxy, amino or thio radicals optionally protected by "ad hoc" protective groups, —OR$^a$, —NHR$^a$, —NR$^a$R$^b$, —SR$^a$, —OCOR$^a$, —OCONHR$^a$, —OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N—(C=NCOR$^a$)NHCOR$^b$, —N(C=NCOOR$^a$)NHCO-OR$^b$ radicals, in which R$^a$ and R$^b$, identical or different, represent the linear or branched cycloalkyl, cycloalkenyl, aromatic, or aromatic or non-aromatic heterocyclic alkyl, alkenyl, alkynyl groups comprising 1 to 15 carbon atoms, optionally substituted, by alkyl radicals comprising 1 to 15 carbon atoms, optionally substituted, by linear or branched alkenyl radicals comprising 1 to 15 carbon atoms, optionally substituted, by linear or branched alkynyl radicals comprising 1 to 15 carbon atoms, optionally substituted, by linear or branched aryl radicals comprising 6 to 12 carbon atoms, optionally substituted, by aromatic or non-aromatic heterocycles comprising 2 to 12 carbon atoms, optionally substituted.

In the above and hereafter, the R$^a$, R$^b$ and R$^{b'}$ groups, identical or different, represent linear or branched cycloalkyl, cycloalkenyl, aromatic, or aromatic or non-aromatic heterocyclic alkyl, alkenyl, alkynyl groups comprising 1 to 15 carbon atoms, optionally substituted.

The term "protective group of an alcohol function" represents a group intended to protect an alcohol against undesirable reactions during the synthesis steps. The protective groups of the alcohols which are commonly used are described in Greene, "Protective Groups In Organic Synthesis" (John Wiley & Sons, New York (1981). Examples of such groups are the acetyl, benzoyl, benzyl pivaloyl, trityl, methoxytrityl, dimethoxytrityl, tetrahydropyranyl groups, and ethers such as the methyl, benzyl, allyl, ethoxyethyl, β-methoxyethoxymethyl, methoxymethyl, p-methoxybenzyl, methylthiomethyl, and silyl ethers.

The term "protective group of a thiol function" represents a group intended to protect a thiol against undesirable reactions during the synthesis steps.

The protective groups of the thiols commonly used are described in Greene, "Protective Groups In Organic Synthesis" (John Wiley & Sons, New York (1981). Examples of such groups are the benzoyl groups and ethers such as the methyl, ethoxyethyl, benzyl, p-methoxybenzyl and silyl ethers.

The term "protective group of an amine function" represents a group intended to protect an amine against undesirable reactions during the synthesis steps. The protective groups of the amines commonly used are described in Greene (ibid.). Examples of such groups are the carbamate, amide groups and the N-alkyl, acetal, N-benzyl, imine, enamine and N-heteroatom derivatives. In particular, the protective groups of the amines comprise the formyl, acetyl, benzoyl, pivaloyl, phenysulphonyl, p-toluenesulphonyl (tosyl), benzyl, t-butyloxycarbonyl (Boc), benzyloxycarbonyl (Cbz) and fluorenylmethyloxycarbonyl (Fmoc) groups.

As regards the conversion of the W$_1$ to the W group, the conversion of an ester —COOR$^a$ to the corresponding acid can be carried out by methods well known to a person skilled in the art, for example by saponification, or by acid hydrolysis.

The acid thus obtained can be converted to the corresponding aldehyde by passing via a Weinreb amide of CONR—OR' type then subsequent reduction by a hydride, for example DIBALH, in a solvent, for example THF, at low temperature.

The conversion of an ester to the corresponding aldehyde can for example be carried out by reduction of the ester by a hydride, in particular DIBAlH, in a solvent, for example THF, at low temperature, or by reduction to alcohol by the action of a hydride, in particular $NaBH_4$ or $LiAlH_4$, then subsequent oxidation to aldehyde by the action of an oxidizing reagent, for example a chromate reagent of PDC or PCC type, a periodinane of the Dess-Martin reagent or IBX type, a sulphoxide in the presence of a base according to the Swern reaction.

The conversion of a ketone —$COR^a$ to the corresponding alcohol —$CHR^aOH$ can for example be carried out by a reduction reaction under standard conditions known to a person skilled in the art, in particular the action of a borohydride, preferentially $NaBH_4$, in an alcoholic solvent, in particular methanol.

Said alcohol —$CHR^aOH$ can be converted to —$CHR^a$-$OR^b$ by the action of a strong base such as NaH or LDA then alkylation by an alkyl halide $R^b$—X.

The conversion of a ketone —$COR^a$ to a corresponding alcohol —$CR^aR^bOH$ can for example be carried out by the action of a Grignard reagent of $R^b$—MgX type in a THF or diethyl ether type solvent. Said alcohol —$CR^aR^bOH$ can be converted to —$CR^aR^bOR^{b'}$ by an alkylation reaction as described previously.

The conversion of an amide —$CONH_2$, —$CONHR^a$ or —$CONR^aR^b$ to the corresponding amine —$CH_2NH_2$, —$CH_2NHR^a$ and —$CH_2NR^aR^b$ respectively can for example be carried out by a reduction reaction of the amide function by the action of a hydride, preferentially $LiAlH_4$, in a solvent, in particular THF. If necessary, the protection of the amine by a protective group, for example the CBz group is carried out according to a procedure known to a person skilled in the art; when the protective group is for example an amide, the action of an acid chloride $R^aCOCl$ (for example EtCOCl) in the presence of a mineral or organic base in a solvent, preferentially dimethylformamide, makes it possible to form the corresponding amide.

The conversion of —$CONH_2$ to —$CONHSO_2R^a$ is for example carried out by the action of sulphonyl chloride $ClSO_2R^a$ on the amide.

As regards the conversion of the $W_2$ to the W group, the deprotection of Z', Z and/or $Z_2$ is carried out according to procedures well known to a person skilled in the art. For example the conversion of —$NZZ_2$ to —NHZ can be carried out by selective deprotection of the protective group $Z_2$, for example, in the case of Z=—COAlkyl and $Z_2$=Boc by acid hydrolysis (for example trifluoroacetic acid) in an organic solvent of the dichloromethane or dioxane type, or for example, in the case of Z=—Bn and $Z_2$=Fmoc by treatment with a secondary base (preferentially piperidine) in DMF, or for example, in the case of Z=COAlkyl and $Z_2$=CBz by hydrogenolysis in the presence of a catalyst (preferentially Pd/C) in an alcoholic solvent.

As regards the conversion of the —$BF_3M$ to the X group, the conversion of a —BF3M to a —$B(OH)_2$ group can for example be carried out by basic hydrolysis in the presence of a mineral or organic base, for example $Na_2CO_3$ or LiOH, in a water/organic solvent mixture, for example dichloromethane, acetonitrile or THF, or by acid hydrolysis in the presence of a Lewis acid, for example $FeCl_3$, or preferentially by passing to a dihalogenoborane by treatment with a silane, for example $SiCl_4$ or TMSCl, in a water/organic solvent mixture, for example dichloromethane, acetonitrile, THF, dioxane or acetone at ambient temperature then in situ hydrolysis.

The conversion of a —$BF_3M$ to a $B(OR)_2$ group can for example be carried out by intermediate passing via $B(OH)_2$ as described previously then subsequent protection in boronic ester, for example $B(Opinacol)_2$, by the action of the alcohol protective group (for example diol pinacol) in an alcoholic solvent in the optional presence of an acid catalyst, for example PTSA, and of a drying agent, for example $MgSO_4$ or a molecular sieve in a solvent, in particular an alcohol, toluene, or diethyl ether at ambient temperature or under reflux of the solvent or preferentially by passing to a dihalogenoborane by treatment with a silane, in particular $SiCl_4$ or TMSCl, in a water/organic solvent mixture, for example dichloromethane, acetonitrile, THF, dioxane or acetone, at ambient temperature then treatment with the protective group in the form of diol, for example the diol pinacol, in an alcoholic solvent.

The conversion of a —$BF_3M$ to a $B(OR')_3M$ group can for example be carried out by intermediate passing via $B(OH)_2$ as described previously then treatment with an alcohol R'OH in the presence of a strong mineral base, preferentially potash, in a solvent, preferentially warm toluene.

As regards the conversion of the —$B(OR)_2$ group to an X group, said conversion step is in particular in the presence of $MHF_2$ when X represents $BF_3M$, or is in particular a hydrolysis, more particularly in the presence of a mineral, organic base or in the presence of a Lewis acid, when X represents $B(OH)_2$.

The conversion of a —$B(OR)_2$ to a $B(OR')_3M$ group can for example be carried out by treatment with an alcohol R'OH in the presence of a strong mineral base, preferentially potash, in a solvent, preferentially warm toluene.

According to an advantageous embodiment, the present invention relates to a process for the preparation of a compound corresponding to formula (I), in which W represents a functional group chosen from —CHO, —$COR^a$, —COOH, —$COOR^a$, —$CONH_2$, —$CONHR^a$, —$CONR^aR^b$, —$CH_2OH$, —$CH_2OR^a$, —$CHR^bOH$, —$CHR^bOR^a$, —$CR^bR^{b'}OH$, —$CR^bR^{b'}OR^a$, —$CH_2NH_2$, —$CH_2NHZ$, —$CHR^aNHZ$, said process comprising:

a step of reaction between:
  a diazoic derivative of the following formula:

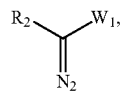

in which $R_2$ is as defined previously, $W_1$ being chosen from the group constituted by —$COR^a$, —$COOR^a$, —$CONH_2$, —$CONHR^a$, and —$CONR^aR^b$, and
a vinyltrifluoroborate compound of the following formula:

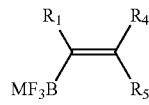

in which $R_1$, $R_4$, $R_5$ and M are as defined previously, in the presence of a catalyst containing a transition metal, in order to obtain a compound of the following formula:

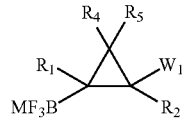

in which $R_1$, $R_2$, $R_4$, $R_5$, $W_1$ and M are as defined previously, if W is different from $W_1$ and/or X is different from $MF_3B$, said process also comprising the following steps:

a step of conversion of $W_1$ to W making it possible to obtain

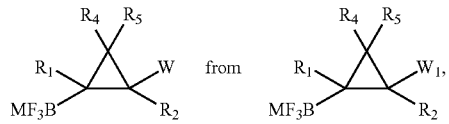

and a step of conversion of —$BF_3M$ to —X making it possible to obtain

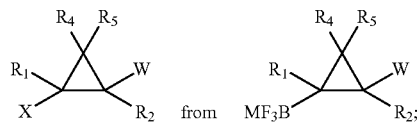

or a step of conversion of —$BF_3M$ to —X making it possible to obtain

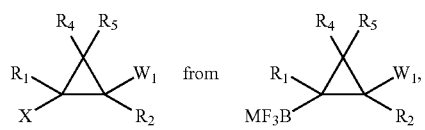

and a step of conversion of $W_1$ to W making it possible to obtain

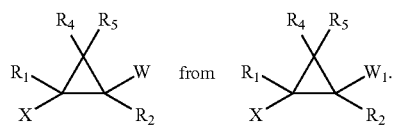

According to an advantageous embodiment, the present invention relates to a process for the preparation of a compound corresponding to formula (I), in which W represents a functional $W_1$ group chosen from —$COR^a$, —$COOR^a$, —$CONH_2$, —$CONHR^a$, and —$CONR^aR^b$, said process comprising:

a step of reaction between:

a diazoic derivative of the following formula:

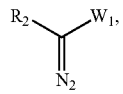

in which $R_2$ is as defined previously, $W_1$ being as defined above, and a vinyltrifluoroborate compound of the following formula:

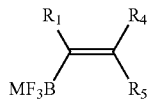

in which $R_1$, $R_4$, $R_5$ and M are as defined previously, in the presence of a catalyst containing a transition metal, in order to obtain a compound of the following formula:

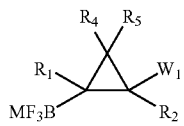

in which $R_1$, $R_2$, $R_4$, $R_5$, $W_1$ and M are as defined above.

According to an advantageous embodiment, the present invention relates to a process for the preparation of a compound corresponding to formula (I), in which W represents a functional group chosen from —CHO, —$CH_2OH$, —$CH_2OR^a$, —$CHR^bOH$, —$CHR^bOR^a$, —$CR^bR^{b'}OH$, —$CR^bR^{b'}OR^a$, —$CH_2NH_2$, —$CH_2NHZ$, —$CHR^aNHZ$, said process comprising:

a step of reaction between:

a diazoic derivative of the following formula:

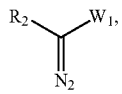

in which $R_2$ is as defined previously, $W_1$ being chosen from the group constituted by —$COR^a$, —$COOR^a$, —$CONH_2$, —$CONHR^a$, and —$CONR^aR^b$, and a vinyltrifluoroborate compound of the following formula:

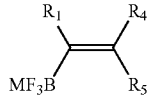

in which $R_1$, $R_4$, $R_5$ and M are as defined previously, in the presence of a catalyst containing a transition metal, in order to obtain a compound of the following formula:

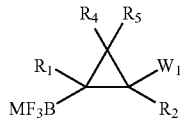

in which $R_1$, $R_2$, $R_4$, $R_5$, $W_1$ and M are as defined previously, said process also comprising the following step:

a step of conversion of $W_1$ to W making it possible to obtain

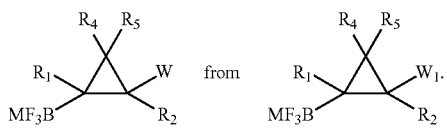

According to an advantageous embodiment, the present invention relates to a process for the preparation of a compound corresponding to formula (I), in which W represents a functional $W_1$ group chosen from —$COR^a$, —$COOR^a$, —$CONH_2$, —$CONHR^a$, and —$CONR^aR^b$, said process comprising:

a step of reaction between:
a diazoic derivative of the following formula:

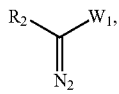

in which $R_2$ is as defined previously, $W_1$ being as defined above,
and
a vinyltrifluoroborate compound of the following formula:

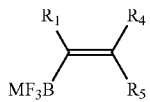

in which $R_1$, $R_4$, $R_5$ and M are as defined previously,
in the presence of a catalyst containing a transition metal, in order to obtain a compound of the following formula:

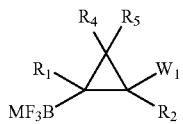

in which $R_1$, $R_2$, $R_4$, $R_5$, $W_1$ and M are as defined above,
said process also comprising the following step:
a step of conversion of $BF_3M$ to X, X representing $B(OH)_2$, $B(OR)_2$, or $B(OR')_3M$, making it possible to obtain

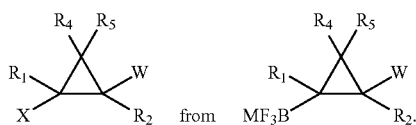

According to an advantageous embodiment, the present invention relates to a process for the preparation of a compound corresponding to formula (I), in which W represents a functional group chosen from —CHO, —$CH_2OH$, —$CH_2OR^a$, —$CHR^bOH$, —$CHR^bOR^a$, —$CR^bR^{b'}OH$, —$CR^bR^{b'}OR^a$, —$CH_2NH_2$, —$CH_2NHZ$, —$CHR^aNHZ$, said process comprising:

a step of reaction between:
a diazoic derivative of the following formula:

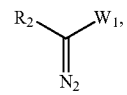

in which $R_2$ is as defined previously, $W_1$ being chosen from the group constituted by —$COR^a$, —$COOR^a$, —$CONH_2$, —$CONHR^a$, and —$CONR^aR^b$,
and
a vinyltrifluoroborate compound of the following formula:

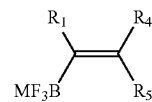

in which $R_1$, $R_4$, $R_5$ and M are as defined previously,
in the presence of a catalyst containing a transition metal, in order to obtain a compound of the following formula:

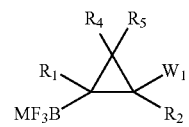

in which $R_1$, $R_2$, $R_4$, $R_5$, $W_1$ and M are as defined previously,
said process also comprising the following steps:
a step of conversion of $W_1$ to W making it possible to obtain

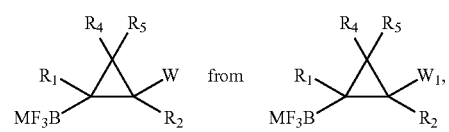

and
a step of conversion of $BF_3M$ to X, X representing $B(OH)_2$, $B(OR)_2$, or $B(OR')_3M$, making it possible to obtain

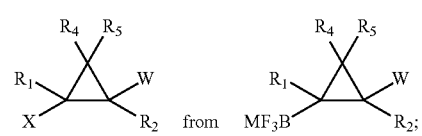

or
a step of conversion of $BF_3M$ to X, X representing $B(OH)_2$, $B(OR)_2$, or $B(OR')_3M$, making it possible to obtain

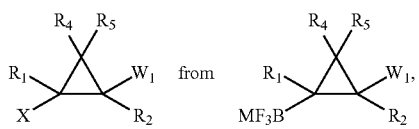

and
a step of conversion of $W_1$ to W making it possible to obtain

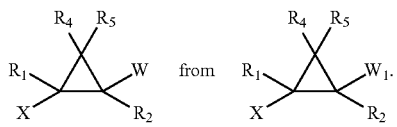

According to an advantageous embodiment, the present invention relates to a preparation process in which said catalyst containing a transition metal, said catalyst being in particular a palladium (II) complex, more particularly $Pd(OAc)_2$ or $Pd(acac)_2$, a copper (II) complex, more particularly $CuSO_4$, $Cu(acac)_2$, $Cu(tBuSalen)_2$, $Cu(OTf)_2$, a copper (I) complex, more particularly CuI or Cu(OTf), or a rhodium (II) complex, more particularly $Rh_2(OAc)_4$, $Rh_2$(Octanoate)$_4$ or $Rh_2$(5S-MEPY)$_4$ (Doyle catalyst).

According to an advantageous embodiment, the present invention relates to a preparation process, in which $W_1$ represents —COOR$^a$, R$^a$ being as defined previously.

According to an advantageous embodiment, the present invention relates to a preparation process, in which $R_2$ is chosen from the group constituted by the —COR$^a$, —COOR$^a$, —CONH$_2$, —CONHR$^a$, —CONR$^a$R$^b$, —CN and —NO$_2$ groups,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;
R$^a$ and R$^b$ being able to be linked in order to form a ring, optionally substituted.

According to an advantageous embodiment, the present invention relates to a preparation process, in which $R_2$ represents H.

According to an advantageous embodiment, the present invention relates to a preparation process, in which $R_1$, $R_4$ and $R_5$ represent H, an aryl, a heterocycle, a heteroaryl or an alkyl as defined previously.

According to an advantageous embodiment, the present invention relates to a preparation process, in which $R_1$, $R_2$, $R_4$ and $R_5$ represent H.

According to an advantageous embodiment, the present invention relates to a preparation process, in which W represents a functional group chosen from —CONH—SO$_2$-cyclopropyl, —CH$_2$—NH—CO—CH$_2$—CH$_3$, and the group of the following formula:

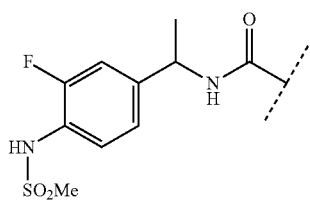

According to an advantageous embodiment, the present invention relates to a process for the preparation of a compound corresponding to the following formula (I-A)

(I-A)

in which:
X represents a substituted boron atom chosen from the group comprising $B(OH)_2$, $B(OR)_2$, $BF_3M$, $B(OR')_3M$ in which:
R is an alkyl group comprising 1 to 14 carbon atoms or an aryl group, optionally substituted, or is such that (OR)$_2$ forms a ring between the two oxygen atoms, (OR)$_2$ being in particular chosen from the group comprising the bivalent radicals deriving from diols, such as O—CH$_2$—CH$_2$—O, O—CH$_2$—CH$_2$—CH$_2$—O, O—CH$_2$—C(CH$_3$)$_2$—CH$_2$—O, O—C(CH$_3$)$_2$—CH$_2$—CH$_2$—C(CH$_3$)$_2$—O, O—CH(CH$_3$)—CH$_2$—CH$_2$—CH(CH$_3$)—O, O—CH(Ph)-CH(Ph)-O, O—CH(CH$_3$)—CH$_2$—C(CH$_3$)$_2$—O, O-o-Ph-O, O—CH$_2$—CH$_2$—NH—CH$_2$—CH$_2$—O, O—CH$_2$—CH$_2$—N(CH$_2$—CH$_2$—CH$_3$)—CH$_2$—CH$_2$—O, O—CH(COOH)—CH(COOH)—O and its esters, and the bivalent radicals deriving from diacids, such as OCO—CH$_2$—N(CH$_3$)—CH$_2$—COO,
R' is an alkyl group comprising 1 to 14 carbon atoms or is such that:
(OR')$_3$ forms a ring between two of the oxygen atoms, (OR')$_3$ then being in the form OR'(OR)$_2$, where R' is an alkyl group comprising 1 to 14 carbon atoms and (OR)$_2$ is as defined above, or
(OR')$_3$ forms a bicycle between the three oxygen atoms, (OR')$_3$ being in particular chosen from the group comprising the trivalent radicals deriving from triols, such as H$_3$C—C—(CH$_2$—O)$_3$,
M represents the lithium Li$^+$ ion, the sodium Na$^+$ ion, the potassium K$^+$ ion, the caesium Cs$^+$ ion, the ammonium R$^c$R$^d$R$^e$R$^f$N$^+$ ion where R$^c$, R$^d$ R$^e$, R$^f$ are chosen from H or a saturated carbon-containing chain comprising in particular 1 to 6 carbon atoms chosen independently of one another,
and in particular X represents $B(OH)_2$, $B(OR)_2$ or $BF_3K$,
$R_1$ and $R_4$, identical or different, are chosen from the group constituted by:
1. H
2. the aryls comprising rings with 6 to 15 carbon atoms, optionally substituted;
3. the heterocycles or heteroaryls comprising rings with 2 to 15 carbon atoms, optionally substituted;
4. the linear or branched alkenyls comprising 1 to 12 carbon atoms, optionally substituted, or carbon rings comprising 3 to 12 carbon atoms and one or more C=C double bonds, optionally substituted;
5. the linear or branched alkynyls comprising 1 to 15 carbon atoms, optionally substituted;
6. the linear, cyclic or branched alkyl groups comprising 1 to 15 carbon atoms, optionally substituted;
at least one of the $R_1$ and $R_4$ groups representing H,
$R_2$ is chosen from the group constituted by the groups being able to be represented by $R_1$ or $R_4$, as well as —COR$^a$, —COOR$^a$, —CONH$_2$, —CONHR$^a$, —CONR$^a$R$^b$, —CN and —NO$_2$, in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;

$R^a$ and $R^b$ being able to be linked in order to form a ring, optionally substituted, W represents a functional group chosen from —CHO, —$COR^a$, —COOH, —$COOR^a$, —$CONH_2$, —$CONHR^a$, —$CONR^aR^b$, —CONH—$SO_2$—$R^a$, —$CH_2OH$, —$CH_2OR^a$, —$CHR^bOH$, —$CHR^bOR^a$, —$CR^bR^{b'}OH$, —$CR^bR^{b'}OR^a$, —$CH_2NH_2$, —$CH_2NHZ$, —$CHR^aNHZ$, —$CH_2$—NH—$COR^a$, in which Z represents a protective group of an amine function, and in which $R^a$, $R^b$ and $R^{b'}$, identical or different, represent linear, cyclic or branched, aromatic, or aromatic or non-aromatic heterocyclic alkyl, alkenyl, alkynyl groups comprising 1 to 15 carbon atoms, optionally substituted;

said process comprising:

a step of reaction between:

a diazoic derivative of the following formula:

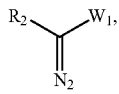

in which $R_2$ is as defined above, $W_1$ being chosen from the group constituted by —$COR^a$, —$COOR^a$, —$CONH_2$, —$CONHR^a$, and —$CONR^aR^b$, and a vinyltrifluoroborate compound of the following formula:

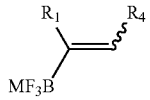

in which $R_1$, $R_4$ and M are as defined above, in the presence of a catalyst containing a transition metal, in order to obtain a compound of the following formula:

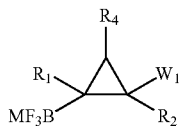

in which $R_1$, $R_2$, $R_4$, $W_1$ and M are as defined above, if W is different from $W_1$ and/or X is different from $MF_3B$, said process also comprising the following steps:

a step of conversion of $W_1$ to W making it possible to obtain

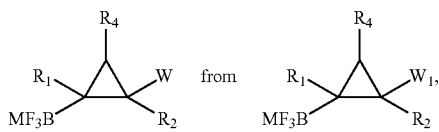

in particular, when $W_1$=$COOR^a$ and W=CHO, by reduction in order to form the corresponding alcohol, then oxidation of said alcohol, when $W_1$=—$COOR^a$ and W=$CH_2OH$ or —$CH_2OR^b$, by the formation of an aldehyde as described previously, then by reduction of said aldehyde and optional alkylation, when $W_1$=—$COR^a$ and W=—$CHR^aOH$, —$CHR^aOR^b$, by reduction then optional alkylation of the alcohol obtained, when $W_1$=—$COR^a$ and W=$CR^aR^bOH$ or —$CR^aR^bOR^{b'}$ by addition of a Grignard reagent then optional alkylation of the alcohol obtained, when $W_1$=—$CONH_2$, —$CONHR^a$ or —$CONR^aR^b$ and W=—$CH_2NH_2$, —$CH_2NHR^a$, —$CH_2NR^aR^b$, —$CH_2NHZ$ or —$CH_2$—NH—$COR^a$, by reduction then optional protection by Z of the amine obtained or optional reaction with the acid chloride $R^aCOCl$, when $W_1$=—$CONH_2$ and W=—$CONHSO_2R^a$, by the action of sulphonyl chloride $ClSO_2R^a$ on the amide, and a step of conversion of —$BF_3M$ to —X making it possible to obtain

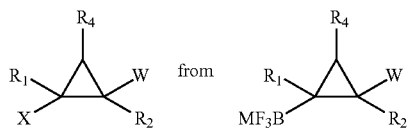

in particular, when X=$B(OH)_2$, by basic or acid hydrolysis, or by passing via a dihalogenoborane, more particularly a dichloroborane, when X=$B(OR)_2$, by passing via X=$B(OH)_2$ as described previously then by the action of an alcohol, in particular an alcohol of formula ROH, a diol or a triol, or by passing via a dihalogenoborane, more particularly a dichloroborane, then by the action of an alcohol, in particular an alcohol of formula ROH, a diol or a triol, or a step of conversion of —$BF_3M$ to —X making it possible to obtain

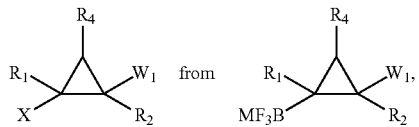

and a step of conversion of $W_1$ to W making it possible to obtain

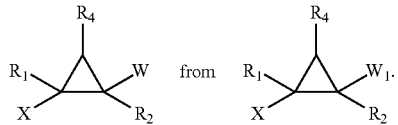

According to an advantageous embodiment, the present invention relates to a process for the preparation of a compound corresponding to the following formula (I-B)

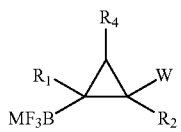

(I-B)

in which:
M represents the lithium Li+ ion, the sodium Na+ ion, the potassium K+ ion, the caesium Cs+ ion, the ammonium $R^cR^dR^eR^fN^+$ ion where $R^c$, $R^d$ $R^e$, $R^f$ are chosen from H or a saturated carbon-containing chain comprising in particular 1 to 6 carbon atoms chosen independently of one another, $BF_3M$ representing in particular $BF_3K$, $R_1$ and $R_4$, identical or different, are chosen from the group constituted by:
1. H
2. the aryls comprising rings with 6 to 15 carbon atoms, optionally substituted;
3. the heterocycles or heteroaryls comprising rings with 2 to 15 carbon atoms, optionally substituted;
4. the linear or branched alkenyls comprising 1 to 12 carbon atoms, optionally substituted, or carbon rings comprising 3 to 12 carbon atoms and one or more C=C double bonds, optionally substituted;
5. the linear or branched alkynyls comprising 1 to 15 carbon atoms, optionally substituted;
6. the linear, cyclic or branched alkyl groups comprising 1 to 15 carbon atoms, optionally substituted;
at least one of the $R_1$ and $R_4$ groups representing H, $R_2$ is chosen from the group constituted by the groups being able to be represented by $R_1$ or $R_4$, as well as —$COR^a$, —$COOR^a$, —$CONH_2$, —$CONHR^a$, —$CONR^aR^b$, —CN and —$NO_2$,
in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;
$R^a$ and $R^b$ being able to be linked in order to form a ring, optionally substituted, W represents a functional group chosen from —CHO, —$COR^a$, —COOH, —$COOR^a$, —$CONH_2$, —$CONHR^a$, —$CONR^aR^b$, —CONH—$SO_2$—$R^a$, —$CH_2OH$, —$CH_2OR^a$, —$CHR^bOH$, —$CHR^bOR^a$, —$CR^bR^{b'}OH$, —$CR^bR^{b'}OR^a$, —$CH_2NH_2$, —$CH_2NHZ$, —$CHR^aNHZ$, —$CH_2$—NH—$COR^a$,
in which Z represents a protective group of an amine function, and
in which $R^a$, $R^b$ and $R^{b'}$, identical or different, represent linear, cyclic or branched, aromatic, or aromatic or non-aromatic heterocyclic alkyl, alkenyl, alkynyl groups comprising 1 to 15 carbon atoms, optionally substituted;

said process comprising:
a step of reaction between:
a diazoic derivative of the following formula:

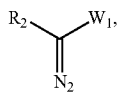

in which $R_2$ is as defined above, $W_1$ being chosen from the group constituted by —$COR^a$, —$COOR^a$, —$CONH_2$, —$CONHR^a$, and —$CONR^aR^b$, and
a vinyltrifluoroborate compound of the following formula:

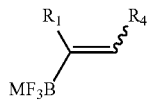

in which $R_1$, $R_4$ and M are as defined above,
in the presence of a catalyst containing a transition metal, in order to obtain a compound of the following formula:

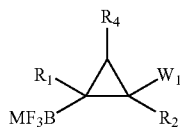

in which $R_1$, $R_2$, $R_4$, $W_1$ and M are as defined above,
if W is different from $W_1$, said process also comprising the following steps:
a step of conversion of $W_1$ to W making it possible to obtain

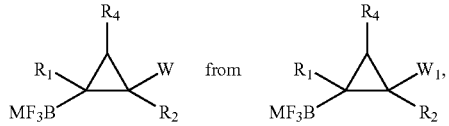

in particular, when $W_1$=$COOR^a$ and W=CHO, by reduction in order to form the corresponding alcohol, then oxidation of said alcohol, when $W_1$=—$COOR^a$ and W=$CH_2OH$ or —$CH_2OR^b$, by the formation of an aldehyde as described previously, then by reduction of said aldehyde and optional alkylation, when $W_1$=—$COR^a$ and W=—$CHR^aOH$, —$CHR^aOR^b$, by reduction then optional alkylation of the alcohol obtained, when $W_1$=—$COR^a$ and W=$CR^aR^bOH$ or —$CR^aR^bOR^{b'}$ by addition of a Grignard reagent then optional alkylation of the alcohol obtained, when $W_1$=—$CONH_2$, —$CONHR^a$ or —$CONR^aR^b$ and W=—$CH_2NH_2$, —$CH_2NHR^a$, —$CH_2NR^aR^b$, —$CH_2NHZ$ or —$CH_2$—NH—$COR^a$, by reduction then optional protection by Z of the amine obtained or optional reaction with the acid chloride $R^aCOCl$, when $W_1$=—$CONH_2$ and W=—$CONHSO_2R^a$, by the action of sulphonyl chloride $ClSO_2R^a$ on the amide.

According to an advantageous embodiment, the present invention relates to a process for the preparation of a compound of formula (I-A), in which:

when $R_1$, $R_2$ and $R_4$ represent H and B represents $B(OH)_2$, $B(OR)_2$, or $B(OR')_3M$, then W is chosen from —$COR^a$, —$CONH_2$, —$CONHR^a$, —$CONR^aR^b$, when $R_1$, $R_2$ and $R_4$ represent H and B represents $BF_3M$, then W is chosen from —COOH, —$COOR^a$, —CHO, —$COR^a$—$CONH_2$, —$CONHR^a$, —$CONR^aR^b$, when W represents CH$_2$OH, —CH$_2$OR$^a$, —CHR$^b$OH, —CHR$^b$OR$^a$, —CR$^b$R$^{b'}$OH, or —CR$^b$R$^{b'}$OR$^a$, and B represents B(OH)$_2$, B(OR)$_2$, or B(OR')$_3$M, then:
R$_1$ does not represent H, or
R$_2$ and R$_4$ do not represent H,
when W represents CH$_2$OH, —CH$_2$OR$^a$, —CHR$^b$OH, —CHR$^b$OR$^a$, —CR$^b$R$^{b'}$OH, or —CR$^b$R$^{b'}$OR$^a$, and B represents BF$_3$M, then R$_1$ or R$_2$ do not represent H.
when W represents —COOH or —COOR$^a$, and B represents B(OH)$_2$, B(OR)$_2$, or B(OR')$_3$M, then:
R$_1$ does not represent H, or
R$_2$ and R$_4$ do not represent H.

According to an advantageous embodiment, the present invention relates to a process for the preparation of a compound of formula (I-B), in which:
when R$_1$, R$_2$ and R$_4$ represent H, then W is chosen from —COOH, —COOR$^a$, —CHO, —COR$^a$—CONH$_2$, —CONHR$^a$, —CONR$^a$R$^b$,
when W represents CH$_2$OH, —CH$_2$OR$^a$, —CHR$^b$OH, —CHR$^b$OR$^a$, —CR$^b$R$^{b'}$OH, or —CR$^b$R$^{b'}$OR$^a$, then R$_1$ or R$_2$ do not represent H.

According to an advantageous embodiment, the present invention relates to a process for the preparation of a compound of formula (I-A) or (I-B) in which said catalyst containing a transition metal is a palladium (II) complex, more particularly Pd(OAc)$_2$ or Pd(acac)$_2$, a copper (II) complex, more particularly CuSO$_4$, Cu(acac)$_2$, Cu(tBu-Salen)$_2$, Cu(OTf)$_2$, a copper (I) complex, more particularly CuI or Cu(OTf), or a rhodium (II) complex, more particularly Rh$_2$(OAc)$_4$, Rh$_2$(Octanoate)$_4$ or Rh$_2$(5S-MEPY)$_4$ (Doyle catalyst).

According to an advantageous embodiment, the present invention relates to a process for the preparation of a compound of formula (I-A) or (I-B) in which said catalyst containing a transition metal is a palladium (II) complex, more particularly Pd(OAc)$_2$ or Pd(acac)$_2$, or a copper (II) complex, more particularly CuSO$_4$, Cu(acac)$_2$, Cu(tBu-Salen)$_2$, Cu(OTf)$_2$.

According to an advantageous embodiment, the present invention relates to a process for the preparation of a compound of formula (I-A) or (I-B), in which W$_1$ is chosen from the group constituted by —COOR$^a$, —CONH$_2$, —CONHR$^a$, and —CONR$^a$R$^b$, R$^a$ and R$^b$ being as defined previously.

According to an advantageous embodiment, the present invention relates to a process for the preparation of a compound of formula (I-A) or (I-B), in which W$_1$ represents —COOR$^a$, R$^a$ being as defined previously, R$^a$ representing in particular an alkyl, a cycloalkyl, a benzyl, optionally substituted.

According to an advantageous embodiment, the present invention relates to a process for the preparation of a compound of formula (I-A) or (I-B) in which W represents a functional group chosen from —CHO, —COR$^a$, —COOH, —COOR$^a$, —CONH$_2$, —CONHR$^a$, —CONR$^a$R$^b$, —CONH—SO$_2$—R$^a$, W$_1$ being in particular chosen from the group constituted by —COOR$^a$, —CONH$_2$, —CONHR$^a$, and —CONR$^a$R$^b$, R$^a$ and R$^b$ being as defined previously, W$_1$ representing more particularly —COOR$^a$, R$^a$ being as defined previously, R$^a$ representing in particular an alkyl, a cycloalkyl, a benzyl, optionally substituted.

According to an advantageous embodiment, the present invention relates to a process for the preparation of a compound of formula (I-A) or (I-B) in which W represents a functional group chosen from —CHO, —COR$^a$, —COOH and —COOR$^a$, W$_1$ representing in particular —COOR$^a$, R$^a$ being as defined previously, R$^a$ representing in particular an alkyl, a cycloalkyl, a benzyl, optionally substituted.

According to an advantageous embodiment, the present invention relates to a process for the preparation of a compound of formula (I-A) or (I-B) in which W and W$_1$ represent —COOR$^a$, R$^a$ being as defined previously, R$^a$ representing in particular an alkyl, a cycloalkyl, a benzyl, optionally substituted.

According to an advantageous embodiment, the present invention relates to a process for the preparation of a compound of formula (I-A) or (I-B) in which W represents a functional group chosen from —CONH—SO$_2$-cyclopropyl, —CH$_2$—NH—CO—CH$_2$—CH$_3$ and the group of the following formula:

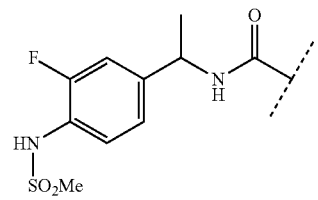

According to an advantageous embodiment, the present invention relates to a process for the preparation of a compound of formula (I-A) or (I-B) in which R$_2$ represents H.

According to an advantageous embodiment, the present invention relates to a process for the preparation of a compound of formula (I-A) or (I-B) in which R$_2$ is chosen from the group constituted by the —COR$^a$, —COOR$^a$, —CONH$_2$, —CONHR$^a$, —CONR$^a$R$^b$, —CN and —NO$_2$ groups,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;
R$^a$ and R$^b$ being able to be linked in order to form a ring, optionally substituted.

According to an advantageous embodiment, the present invention relates to a process for the preparation of a compound of formula (I-A) or (I-B) in which R$_2$ is chosen from the group constituted by the —COR$^a$, —COOR$^a$, —CONH$_2$, —CONHR$^a$, —CONR$^a$R$^b$ and —NO$_2$ groups,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;
R$^a$ and R$^b$ being able to be linked in order to form a ring, optionally substituted.

According to an advantageous embodiment, the present invention relates to a process for the preparation of a compound of formula (I-A) or (I-B) in which R$_2$ is chosen from the group constituted by the —COOR$^a$, —CONH$_2$, —CONHR$^a$ and —CONR$^a$R$^b$ groups,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;
R$^a$ and R$^b$ being able to be linked in order to form a ring, optionally substituted.

According to an advantageous embodiment, the present invention relates to a process for the preparation of a compound of formula (I-A) or (I-B) in which R$_1$, R$_2$ and R$_4$ represent H.

According to an advantageous embodiment, the present invention relates to a process for the preparation of a compound of formula (I-A) or (I-B) in which $R_1$ represents H.

According to an advantageous embodiment, the present invention relates to a process for the preparation of a compound of formula (I-A) or (I-B) in which $R_1$ represents H and $R_4$ represents an aryl, a heterocycle, a heteroaryl or an alkyl as defined previously.

According to an advantageous embodiment, the present invention relates to a process for the preparation of a compound of formula (I-A) or (I-B) in which $R_4$ represents H.

According to an advantageous embodiment, the present invention relates to a process for the preparation of a compound of formula (I-A) or (I-B) in which $R_4$ represents H and $R_1$ represents an aryl, a heterocycle, a heteroaryl or an alkyl as defined previously.

According to an advantageous embodiment, the present invention relates to a process for the preparation of a compound of formula (I-A) or (I-B) in which $R_1$ and $R_2$ represent H and $R_4$ represents an aryl, a heterocycle, a heteroaryl or an alkyl as defined previously.

According to an advantageous embodiment, the present invention relates to a process for the preparation of a compound of formula (I-A) or (I-B) in which $R_2$ and $R_4$ represent H and $R_1$ represents an aryl, a heterocycle, a heteroaryl or an alkyl as defined previously.

According to an advantageous embodiment, the present invention relates to a process for the preparation of a compound of formula (I-A) or (I-B) in which $R_1$ represents H, $R_4$ represents an aryl, a heterocycle, a heteroaryl or an alkyl as defined previously, and $R_2$ is chosen from the group constituted by the —$COR^a$, —$COOR^a$, —$CONH_2$, —$CONHR^a$, —$CONR^aR^b$ and —$NO_2$ groups, in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;

$R^a$ and $R^b$ being able to be linked in order to form a ring, optionally substituted.

According to an advantageous embodiment, the present invention relates to a process for the preparation of a compound of formula (I-A) or (I-B) in which $R_4$ represents H, $R_1$ represents an aryl, a heterocycle, a heteroaryl or an alkyl as defined previously, and $R_2$ is chosen from the group constituted by the —$COR^a$, —$COOR^a$, —$CONH_2$, —$CONHR^a$, —$CONR^aR^b$ and —$NO_2$ groups, in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;

$R^a$ and $R^b$ being able to be linked in order to form a ring, optionally substituted.

According to an advantageous embodiment, the present invention relates to a process for the preparation of a compound of formula (I-A) or (I-B) in which $R_1$ and $R_4$ represent H, and $R_2$ is chosen from the group constituted by the —$COR^a$, —$COOR^a$, —$CONH_2$, —$CONHR^a$, —$CONR^aR^b$ and —$NO_2$ groups, in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;

$R^a$ and $R^b$ being able to be linked in order to form a ring, optionally substituted.

According to an advantageous embodiment, the present invention relates to a process for the preparation of a compound of formula (I-A) or (I-B) in which $R_1$ represents H, said catalyst being a palladium (II) complex, more particularly $Pd(OAc)_2$ or $Pd(acac)_2$.

According to an advantageous embodiment, the present invention relates to a process for the preparation of a compound of formula (I-A) or (I-B) in which $R_4$ represents H, said catalyst being a copper (II) complex, in particular $CuSO_4$, $Cu(acac)_2$, $Cu(tBuSalen)_2$, $Cu(OTf)_2$, or a copper (I) complex, in particular CuI or Cu(OTf), said catalyst being more particularly $CuSO_4$, $Cu(acac)_2$, $Cu(tBuSalen)_2$ or $Cu(OTf)_2$.

According to an advantageous embodiment, the present invention relates to a process for the preparation of a compound corresponding to the following formula (I-C)

(I-C)

in which:

X represents a substituted boron atom chosen from the group comprising $B(OH)_2$, $B(OR)_2$, $BF_3M$, $B(OR')_3M$ in which:

R is an alkyl group comprising 1 to 14 carbon atoms or an aryl group, optionally substituted, or is such that $(OR)_2$ forms a ring between the two oxygen atoms, $(OR)_2$ being in particular chosen from the group comprising the bivalent radicals deriving from diols, such as O—$CH_2$—$CH_2$—O, O—$CH_2$—$CH_2$—$CH_2$—O, O—$CH_2$—$C(CH_3)_2$—$CH_2$—O, O—$C(CH_3)_2$—$CH_2$—$CH_2$—$C(CH_3)_2$—O, O—$CH(CH_3)$—$CH_2$—$CH_2$—CH($CH_3$)—O, O—CH(Ph)-CH(Ph)-O, O—$CH(CH_3)$—$CH_2$—$C(CH_3)_2$—O, O-o-Ph-O, O—$CH_2$—$CH_2$—NH—$CH_2$—$CH_2$—O, O—$CH_2$—$CH_2$—N($CH_2$—$CH_2$—$CH_3$)—$CH_2$—$CH_2$—O, O—CH(COOH)—CH(COOH)—O and its esters, and the bivalent radicals deriving from diacids, such as OCO—$CH_2$—N($CH_3$)—$CH_2$—COO, R' is an alkyl group comprising 1 to 14 carbon atoms or is such that:

(OR')$_3$ forms a ring between two of the oxygen atoms, (OR')$_3$ then being in the form OR'(OR)$_2$, where R' is an alkyl group comprising 1 to 14 carbon atoms and $(OR)_2$ is as defined above, or (OR')$_3$ forms a bicycle between the three oxygen atoms, (OR')$_3$ being in particular chosen from the group comprising the trivalent radicals deriving from triols, such as $H_3C$—C—($CH_2$—O)$_3$, M represents the lithium $Li^+$ ion, the sodium $Na^+$ ion, the potassium $K^+$ ion, the caesium $Cs^+$ ion, the ammonium $R^cR^dR^eR^fN^+$ ion where $R^c$, $R^d$, $R^e$, $R^f$ are chosen from H or a saturated carbon-containing chain comprising in particular 1 to 6 carbon atoms chosen independently of one another, and in particular X represents $B(OH)_2$, $B(OR)_2$ or $BF_3K$, $R_1$ and $R_4$, identical or different, are chosen from the group constituted by:
1. H
2. the aryls comprising rings with 6 to 15 carbon atoms, optionally substituted;
3. the heterocycles or heteroaryls comprising rings with 2 to 15 carbon atoms, optionally substituted;
4. the linear or branched alkenyls comprising 1 to 12 carbon atoms, optionally substituted, or carbon rings comprising 3 to 12 carbon atoms and one or more C=C double bonds, optionally substituted;
5. the linear or branched alkynyls comprising 1 to 15 carbon atoms, optionally substituted;
6. the linear, cyclic or branched alkyl groups comprising 1 to 15 carbon atoms, optionally substituted;
at least one of the $R_1$ and $R_4$ groups representing H,
$R_2$ is chosen from the group constituted by H and the —$COR^a$, —$COOR^a$, —$CONH_2$, —$CONHR^a$, —$CONR^aR^b$ and —$NO_2$ groups,
in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;
$R^a$ and $R^b$ being able to be linked in order to form a ring, optionally substituted,
W represents a functional group chosen from —CHO, —$COR^a$, —COOH, —$COOR^a$, —$CONH_2$, —$CONHR^a$, —$CONR^aR^b$,
in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;
said process comprising:
a step of reaction between:
a diazoic derivative of the following formula:

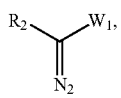

in which $R_2$ is as defined above, $W_1$ being chosen from the group constituted by —$COOR^a$, —$CONH_2$, —$CONHR^a$, and —$CONR^aR^b$,
and
a vinyltrifluoroborate compound of the following formula:

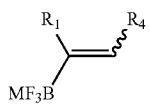

in which $R_1$, $R_4$ and M are as defined above,
in the presence of a catalyst containing a transition metal, said catalyst being a palladium (II) complex, more particularly $Pd(OAc)_2$ or $Pd(acac)_2$, or a copper (II) complex, more particularly $CuSO_4$, $Cu(acac)_2$, $Cu(tBuSalen)_2$, $Cu(OTf)_2$,
said catalyst being in particular a palladium (II) complex, more particularly $Pd(OAc)_2$ or $Pd(acac)_2$, when $R_1$ represents H, said catalyst being in particular a copper (II) complex, in particular $CuSO_4$, $Cu(acac)_2$, $Cu(tBuSalen)_2$, $Cu(OTf)_2$, when $R_4$ represents H,
in order to obtain a compound of the following formula:

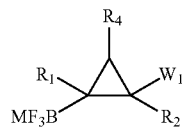

in which $R_1$, $R_2$, $R_4$, $W_1$ and M are as defined above,
if W is different from $W_1$ and/or X is different from $MF_3B$,
said process also comprising the following steps:
a step of conversion of $W_1$ to W making it possible to obtain

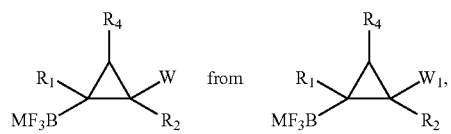

in particular, when $W_1$=$COOR^a$ and W=CHO, by reduction in order to form the corresponding alcohol, then oxidation of said alcohol, when $W_1$=—$CONH_2$ and W=—$CONHSO_2R^a$, by the action of sulphonyl chloride $ClSO_2R^a$ on the amide,
and
a step of conversion of —$BF_3M$ to —X making it possible to obtain

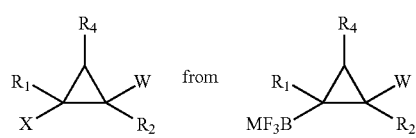

in particular, when X=$B(OH)_2$, by basic or acid hydrolysis, or by passing via a dihalogenoborane, more particularly a dichloroborane, when X=$B(OR)_2$, by passing via X=$B(OH)_2$ as described previously then by the action of an alcohol, in particular an alcohol of formula ROH, a diol or a triol, or by passing via a dihalogenoborane, more particularly a dichloroborane, then by the action of an alcohol, in particular an alcohol of formula ROH, a diol or a triol,
or
a step of conversion of —$BF_3M$ to —X making it possible to obtain

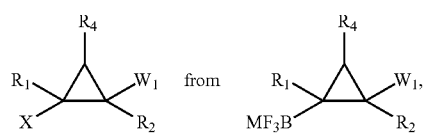

and
a step of conversion of $W_1$ to W making it possible to obtain

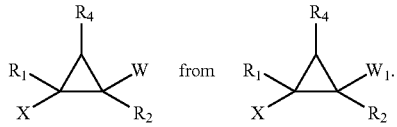

According to an advantageous embodiment, the present invention relates to a process for the preparation of a compound corresponding to the following formula (I-D)

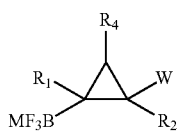

(I-D)

in which:

M represents the lithium $Li^+$ ion, the sodium $Na^+$ ion, the potassium $K^+$ ion, the caesium $Cs^+$ ion, the ammonium $R^cR^dR^eR^fN^+$ ion where $R^c$, $R^d$ $R^e$, $R^f$ are chosen from H or a saturated carbon-containing chain comprising in particular 1 to 6 carbon atoms chosen independently of one another, $BF_3M$ representing in particular $BF_3K$, $R_1$ and $R_4$, identical or different, are chosen from the group constituted by:
1. H
2. the aryls comprising rings with 6 to 15 carbon atoms, optionally substituted;
3. the heterocycles or heteroaryls comprising rings with 2 to 15 carbon atoms, optionally substituted;
4. the linear or branched alkenyls comprising 1 to 12 carbon atoms, optionally substituted, or carbon rings comprising 3 to 12 carbon atoms and one or more C=C double bonds, optionally substituted;
5. the linear or branched alkynyls comprising 1 to 15 carbon atoms, optionally substituted;
6. the linear, cyclic or branched alkyl groups comprising 1 to 15 carbon atoms, optionally substituted;
at least one of the $R_1$ and $R_4$ groups representing H, $R_2$ is chosen from the group constituted by H and the —$COR^a$, —$COOR^a$, —$CONH_2$, —$CONHR^a$, —$CONR^aR^b$ and —$NO_2$ groups,
in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;
$R^a$ and $R^b$ being able to be linked in order to form a ring, optionally substituted;
W represents a functional group chosen from —CHO, —$COR^a$, —COOH, —$COOR^a$, —$CONH_2$, —$CONHR^a$, —$CONR^aR^b$,
in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;
said process comprising:
a step of reaction between:
a diazoic derivative of the following formula:

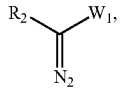

in which $R_2$ is as defined above, $W_1$ being chosen from the group constituted by —$COOR^a$, —$CONH_2$, —$CONHR^a$, and —$CONR^aR^b$,
and
a vinyltrifluoroborate compound of the following formula:

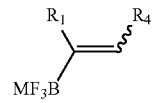

in which $R_1$, $R_4$ and M are as defined above,
in the presence of a catalyst containing a transition metal, said catalyst being a palladium (II) complex, more particularly $Pd(OAc)_2$ or $Pd(acac)_2$, or a copper (II) complex, more particularly $CuSO_4$, $Cu(acac)_2$, $Cu(tBuSalen)_2$, $Cu(OTf)_2$,
said catalyst being in particular a palladium (II) complex, more particularly $Pd(OAc)_2$ or $Pd(acac)_2$, when $R_1$ represents H,
said catalyst being in particular a copper (II) complex, in particular $CuSO_4$, $Cu(acac)_2$, $Cu(tBuSalen)_2$, $Cu(OTf)_2$, when $R_4$ represents H,
in order to obtain a compound of the following formula:

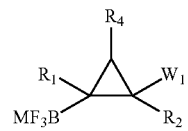

in which $R_1$, $R_2$, $R_4$, $W_1$ and M are as defined above, if W is different from $W_1$, said process also comprising the following steps:
a step of conversion of $W_1$ to W making it possible to obtain

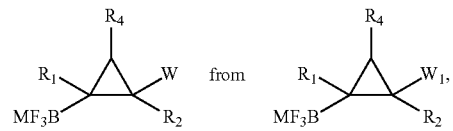

in particular, when $W_1$=$COOR^a$ and W=CHO, by reduction in order to form the corresponding alcohol, then oxidation of said alcohol, when $W_1$=—$CONH_2$ and W=—$CONHSO_2R^a$, by the action of sulphonyl chloride $ClSO_2R^a$ on the amide.

According to an advantageous embodiment, the present invention relates to a process for the preparation of a compound of formula (I-C), in which:
when $R_1$, $R_2$ and $R_4$ represent H and B represents $B(OH)_2$, $B(OR)_2$, or $B(OR')_3M$, then W is chosen from —$COR^a$, —$CONH_2$, —$CONHR^a$, —$CONR^aR^b$,
when W represents —COOH or —$COOR^a$, and B represents $B(OH)_2$, $B(OR)_2$, or $B(OR')_3M$, then:
$R_1$ does not represent H, or
$R_2$ and $R_4$ do not represent H.

According to an advantageous embodiment, the present invention relates to a process for the preparation of a compound of formula (I-C) or (I-D), in which $W_1$ represents —COOR$^a$, R$^a$ being as defined previously, R$^a$ representing in particular an alkyl, a cycloalkyl, a benzyl, optionally substituted.

According to an advantageous embodiment, the present invention relates to a process for the preparation of a compound of formula (I-C) or (I-D) in which W represents a functional group chosen from —CHO, —COR$^a$, —COOH and —COOR$^a$, W$_1$ representing in particular —COOR$^a$, R$^a$ being as defined previously, R$^a$ representing in particular an alkyl, a cycloalkyl, a benzyl, optionally substituted.

According to an advantageous embodiment, the present invention relates to a process for the preparation of a compound of formula (I-C) or (I-D) in which W and W$_1$ represent —COOR$^a$, R$^a$ being as defined previously, R$^a$ representing in particular an alkyl, a cycloalkyl, a benzyl, optionally substituted.

According to an advantageous embodiment, the present invention relates to a process for the preparation of a compound of formula (I-C) or (I-D) in which R$_2$ represents H.

According to an advantageous embodiment, the present invention relates to a process for the preparation of a compound of formula (I-C) or (I-D) in which R$_2$ is chosen from the group constituted by the —COOR$^a$, —CONH$_2$, —CONHR$^a$ and —CONR$^a$R$^b$ groups, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;

R$^a$ and R$^b$ being able to be linked in order to form a ring, optionally substituted.

According to an advantageous embodiment, the present invention relates to a process for the preparation of a compound of formula (I-C) or (I-D) in which R$_1$, R$_2$ and R$_4$ represent H.

According to an advantageous embodiment, the present invention relates to a process for the preparation of a compound of formula (I-C) or (I-D) in which R$_1$ represents H.

According to an advantageous embodiment, the present invention relates to a process for the preparation of a compound of formula (I-C) or (I-D) in which R$_1$ represents H and R$_4$ represents an aryl, a heterocycle, a heteroaryl or an alkyl as defined previously.

According to an advantageous embodiment, the present invention relates to a process for the preparation of a compound of formula (I-C) or (I-D) in which R$_4$ represents H.

According to an advantageous embodiment, the present invention relates to a process for the preparation of a compound of formula (I-C) or (I-D) in which R$_4$ represents H and R$_1$ represents an aryl, a heterocycle, a heteroaryl or an alkyl as defined previously.

According to an advantageous embodiment, the present invention relates to a process for the preparation of a compound of formula (I-C) or (I-D) in which R$_1$ and R$_2$ represent H and R$_4$ represents an aryl, a heterocycle, a heteroaryl or an alkyl as defined previously.

According to an advantageous embodiment, the present invention relates to a process for the preparation of a compound of formula (I-C) or (I-D) in which R$_2$ and R$_4$ represent H and R$_1$ represents an aryl, a heterocycle, a heteroaryl or an alkyl as defined previously.

According to an advantageous embodiment, the present invention relates to a process for the preparation of a compound of formula (I-C) or (I-D) in which R$_1$ represents H, R$_4$ represents an aryl, a heterocycle, a heteroaryl or an alkyl as defined previously, and R$_2$ is chosen from the group constituted by the —COR$^a$, —COOR$^a$, —CONH$_2$, —CONHR$^a$, —CONR$^a$R$^b$ and —NO$_2$ groups, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;

R$^a$ and R$^b$ being able to be linked in order to form a ring, optionally substituted.

According to an advantageous embodiment, the present invention relates to a process for the preparation of a compound of formula (I-C) or (I-D) in which R$_4$ represents H, R$_1$ represents an aryl, a heterocycle, a heteroaryl or an alkyl as defined previously, and R$_2$ is chosen from the group constituted by the —COR$^a$, —COOR$^a$, —CONH$_2$, —CONHR$^a$, —CONR$^a$R$^b$ and —NO$_2$ groups, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;

R$^a$ and R$^b$ being able to be linked in order to form a ring, optionally substituted.

According to an advantageous embodiment, the present invention relates to a process for the preparation of a compound of formula (I-C) or (I-D) in which R$_1$ and R$_4$ represent H, and R$_2$ is chosen from the group constituted by the —COR$^a$, —COOR$^a$, —CONH$_2$, —CONHR$^a$, —CONR$^a$R$^b$ and —NO$_2$ groups, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;

R$^a$ and R$^b$ being able to be linked in order to form a ring, optionally substituted.

According to an advantageous embodiment, the present invention relates to a preparation process, in which W represents —COOR$^a$, —CONH$_2$, —CONHR$^a$, —CONR$^a$R$^b$, —CH$_2$OH, —CH$_2$OR$^a$, —CHR$^b$OH, —CHR$^b$OR$^a$, —CR$^b$R$^{b'}$OH, —CR$^b$R$^{b'}$OR$^a$, —CH$_2$NH$_2$, —CH$_2$NHZ, —CHR$^a$NHZ, said process comprising:

a step of reaction between:
a diazoic derivative of the following formula:

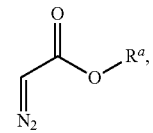

in which R$^a$ is as defined previously,
and
a vinyltrifluoroborate compound of the following formula:

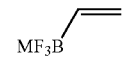

in which M is as defined previously, M representing in particular K,
in the presence of a catalyst containing a transition metal, in order to obtain a compound of the following formula:

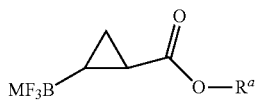

in which $R^a$ and M are as defined above,
if W is different from —COOR$^a$ and/or X is different from MF$_3$B, said process also comprising the following steps:
a step of conversion of —COOR$^a$ to W making it possible to obtain

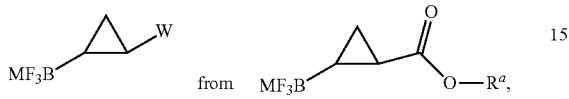

and
a step of conversion of —BF$_3$M to —X making it possible to obtain

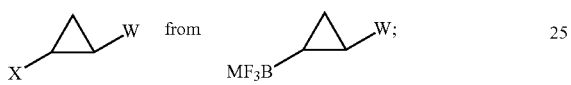

or
a step of conversion of —BF$_3$M to —X making it possible to obtain

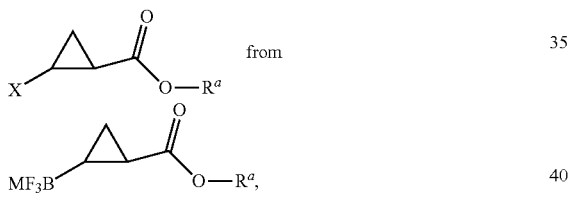

and
a step of conversion of —COOR$^a$ to W making it possible to obtain

According to an advantageous embodiment, the present invention relates to a process for the preparation of a compound of formula (I), in the form of a trans racemic compound of formula (I-1):

and its enantiomer, (I-1)
in which X, $R_1$, $R_2$, $R_4$, $R_5$ and W are as defined previously, said process comprising:

a step of reaction between:
a diazoic derivative of the following formula:

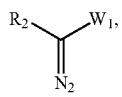

in which $R_2$ is as defined above, $W_1$ being chosen from the group constituted by —COR$^a$, —COOR$^a$, —CONH$_2$, —CONHR$^a$, and —CONR$^a$R$^b$,
and
a vinyltrifluoroborate compound of the following formula:

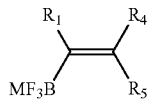

in which $R_1$, $R_4$, $R_5$ and M are as defined above,
in the presence of a catalyst containing a transition metal, in order to obtain a compound of the following formula:

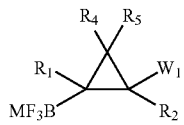

in which $R_1$, $R_2$, $R_4$, $R_5$, $W_1$ and M are as defined above, in the form of a mixture comprising the pairs of enantiomers of the following formulae:

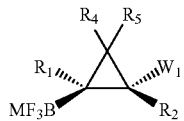

and its enantiomer, and

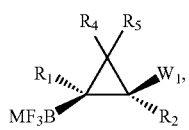

and its enantiomer,
a step of separation of said pairs of enantiomers, in particular by recrystallization, in order to obtain the following pair of trans enantiomers:

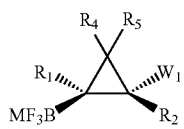

and its enantiomer, if W is different from $W_1$ and/or X is different from $MF_3B$, said process also comprising the following steps:

a step of conversion of $W_1$ to W making it possible to obtain

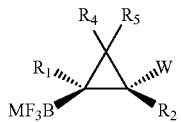

and its enantiomer from

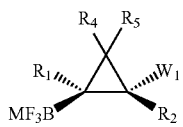

and its enantiomer,
and
a step of conversion of —$BF_3M$ to —X making it possible to obtain

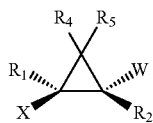

and its enantiomer from

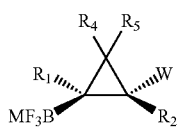

and its enantiomer
or
a step of conversion of —$BF_3M$ to —X making it possible to obtain

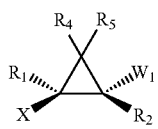

and its enantiomer from

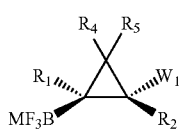

and its enantiomer, and
a step of conversion of $W_1$ to W making it possible to obtain

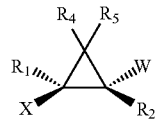

and its enantiomer from

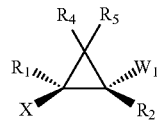

and its enantiomer.

The term "trans" relates to the X group and the W group, and signifies that said X and W groups are not in the same half space, with respect to the plane defined by the cyclopropyl.

For example the compound potassium [(1S,2S)-2-ethoxycarbonylcyclopropyl]-trifluoroborate of the following formula:

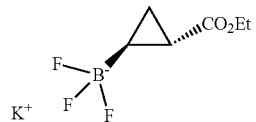 [SMILES: [K+] ; CCOC(=O)[C@H]1C[C@@H]1[B-](F)(F)F]

is trans.

The term "trans" relates to a pair of enantiomers. The following two compounds:

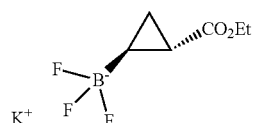 and

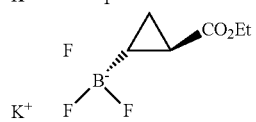

are trans.

Thus, when a "trans" compound of the following formula is mentioned:

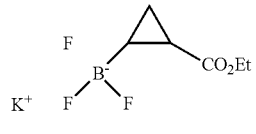

it refers to the following pair of enantiomers:

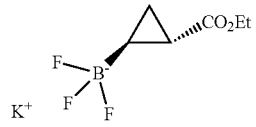 and

-continued

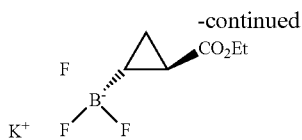

When $R_2$=W, for example $R_2$=W=—COOR$^a$, the concept of "trans" cannot be defined, and the following pair of enantiomers is considered:

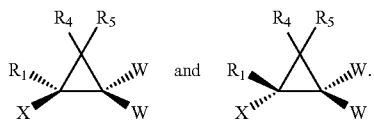

According to an advantageous embodiment, the present invention relates to a process for the preparation of a compound of formula (I), in which $R_1$, $R_2$, $R_4$ and $R_5$ represent H, in the form of a racemic trans compound of formula (I-1a):

and its enantiomer, (I-1a)
in which X and W are as defined previously, said process comprising:
  a step of reaction between:
    a diazoic derivative of the following formula:

$W_1$ being chosen from the group constituted by —COR$^a$, —COOR$^a$, —CONH$_2$, —CONHR$^a$, and —CONR$^a$R$^b$, $W_1$ representing in particular —COOR$^a$,
  and
    a vinyltrifluoroborate compound of the following formula:

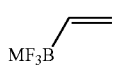

in which M is as defined above,
  in the presence of a catalyst containing a transition metal, in order to obtain a compound of the following formula:

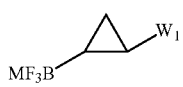

in which $W_1$ and M are as defined above, in the form of a mixture comprising the pairs of enantiomers of the following formulae:

and its enantiomer, and

and its enantiomer,
a step of separation of said pairs of enantiomers, in particular by recrystallization, in order to obtain the following pair of trans enantiomers:

and its enantiomer,
if W is different from $W_1$ and/or X is different from MF$_3$B, said process also comprising the following steps:
  a step of conversion of $W_1$ to W making it possible to obtain

and its enantiomer from

and its enantiomer,
and
a step of conversion of —BF$_3$M to —X making it possible to obtain

and its enantiomer from

and its enantiomer
or
a step of conversion of —BF$_3$M to —X making it possible to obtain

and its enantiomer from

and its enantiomer,
and
a step of conversion of $W_1$ to W making it possible to obtain

and its enantiomer from

and its enantiomer.

According to an advantageous embodiment, the present invention relates to a process for the preparation of a compound of formula (I), in the form of a racemic cis compound of formula (I-2):

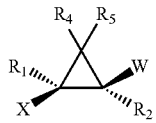

and its enantiomer, (I-2)
in which X, $R_1$, $R_2$, $R_4$, $R_5$ and W are as defined previously, said process comprising:
  a step of reaction between:
    a diazoic derivative of the following formula:

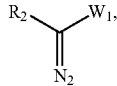

in which $R_2$ is as defined above, $W_1$ being chosen from the group constituted by —COR$^a$, —COOR$^a$, —CONH$_2$, —CONHR$^a$, and —CONR$^a$R$^b$,
and
a vinyltrifluoroborate compound of the following formula:

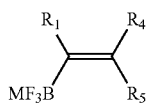

in which $R_1$, $R_4$, $R_5$ and M are as defined above,
in the presence of a catalyst containing a transition metal, in order to obtain a compound of the following formula:

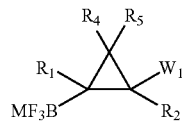

in which $R_1$, $R_2$, $R_4$, $R_5$, $W_1$ and M are as defined above, in the form of a mixture comprising the pairs of enantiomers of the following formulae:

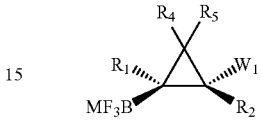

and its enantiomer, and

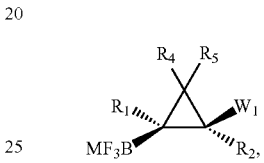

and its enantiomer,
a step of separation of said pairs of enantiomers, in particular by recrystallization, in order to obtain the following pair of trans enantiomers:

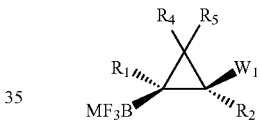

and its enantiomer,
if W is different from $W_1$ and/or X is different from $MF_3B$, said process also comprising the following steps:
  a step of conversion of $W_1$ to W making it possible to obtain

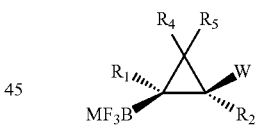

and its enantiomer from

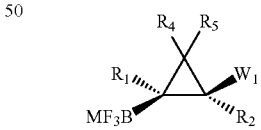

and its enantiomer,
and
a step of conversion of —BF$_3$M to —X making it possible to obtain

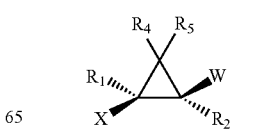

and its enantiomer from

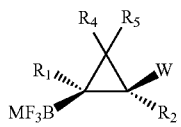

and its enantiomer,
or
a step of conversion of —BF$_3$M to —X making it possible to obtain

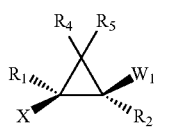

and its enantiomer from

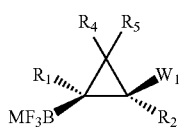

and its enantiomer,
and
a step of conversion of W$_1$ to W making it possible to obtain

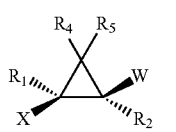

and its enantiomer from

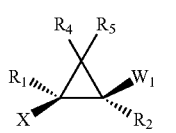

and its enantiomer.

The term "cis" relates to both the X group and the W group, and signifies that said groups X and W are in the same half space, with respect to the plane defined by the cyclopropyl.

For example the compound potassium [(1S,2R)-2-ethoxycarbonylcyclopropyl]-trifluoroborate of the following formula:

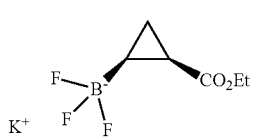 [SMILES: [K+] ; CCOC(=O)[C@@H]1C[C@@H]1[B-](F)(F)F]

is cis.

The term "cis" relates to a pair of enantiomers. The following two compounds:

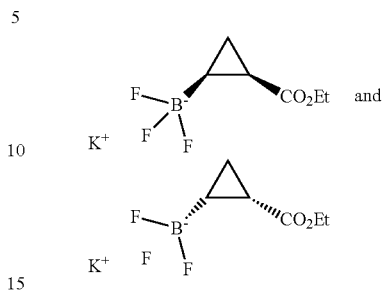

are cis.

Thus, when a "cis" compound of the following formula is mentioned:

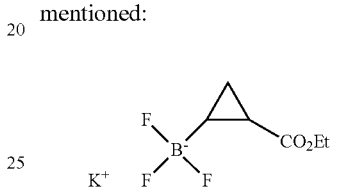

it refers to the following pair of enantiomers:

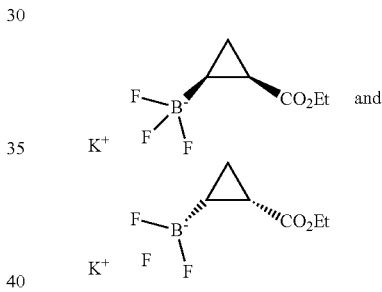

When R$_2$=W, for example R$_2$=W=—COOR$^a$, the concept of "cis" cannot be defined, and the following pair of enantiomers is considered:

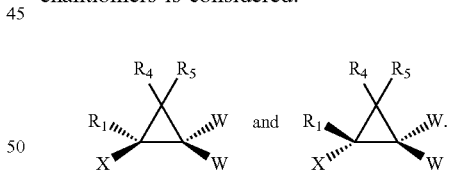

According to an advantageous embodiment, the present invention relates to a process for the preparation of a compound of formula (I), in which R$_1$, R$_2$, R$_4$ and R$_5$ represent H, in the form of a racemic cis compound of formula (I-2a):

and its enantiomer, (I-2a)
in which X and W are as defined previously, said process comprising:

a step of reaction between:

a diazoic derivative of the following formula:

$W_1$ being chosen from the group constituted by —COR$^a$, —COOR$^a$, —CONH$_2$, —CONHR$^a$, and —CONR$^a$R$^b$, $W_1$ representing in particular —COOR$^a$, and a vinyltrifluoroborate compound of the following formula:

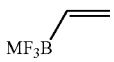

in which M is as defined above, in the presence of a catalyst containing a transition metal, in order to obtain a compound of the following formula:

in which $W_1$ and M are as defined above, in the form of a mixture comprising the pairs of enantiomers of the following formulae:

and its enantiomer, and

and its enantiomer, a step of separation of said pairs of enantiomers, in particular by recrystallization, in order to obtain the following pair of cis enantiomers:

and its enantiomer, if W is different from $W_1$ and/or X is different from MF$_3$B, said process also comprising the following steps:

a step of conversion of $W_1$ to W making it possible to obtain

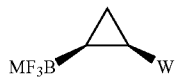

and its enantiomer from

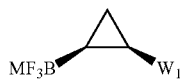

and its enantiomer,
and
a step of conversion of —BF$_3$M to —X making it possible to obtain

and its enantiomer from

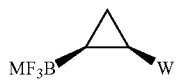

and its enantiomer,
or
a step of conversion of —BF$_3$M to —X making it possible to obtain

and its enantiomer from

and its enantiomer,
and
a step of conversion of $W_1$ to W making it possible to obtain

and its enantiomer from

and its enantiomer.

According to an advantageous embodiment, the present invention relates to a process for the preparation of a compound corresponding to formula (I), in which W represents a functional group chosen from —OH, —OR$^a$, —OZ', —NH$_2$, —NHR$^a$, —NR$^a$R$^b$, —NHZ and —NZZ$_2$, in particular from —OH, —OR$^a$ and —OZ', said process comprising:

the treatment of a compound of the following formula:

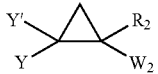

in which R$_2$ is as defined previously, R$_2$ representing in particular H, and in which W$_2$ represents a functional group chosen from —OR$^a$, —OZ', —NR$^a$R$^b$ and —NZZ$_2$, in particular from —OR$^a$ and —OZ', Y being a halide, in particular —Br, Y' being a halide, in particular —Br, or H, by:
a strong base, in particular an alkyl lithium, more particularly n-butyllithium or sec-butyllithium, then a compound of formula X"—B(OR)$_2$, R being as defined above, X" representing H, an O-alkyl group comprising 1 to 14 carbon atoms or an O-aryl group, optionally substituted, in order to obtain a compound of the following formula:

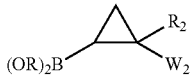

in which R, R$_2$ and W$_2$ are as defined above,
or
a reaction of the Simmons-Smith type starting from a compound of the following formula:

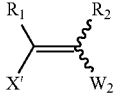

in which R$_1$ and R$_2$ are as defined previously, R$_1$ and R$_2$ representing in particular H, W$_2$ representing a functional group chosen from —OR$^a$, —OZ', —NR$^a$R$^b$ and —NZZ$_2$, in particular from —OR$^a$ and —OZ', X' representing B(OR)$_2$ or BF$_3$M, in particular B(OR)$_2$, in which R and M are as defined previously,
in order to obtain a compound of the following formula:

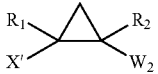

in which R$_1$, R$_2$, X' and W$_2$ are as defined above,
if W represents —OH or —NH$_2$, and/or X is different from B(OR)$_2$, said process also comprising the following steps, R$_1$ representing in particular H:

a step of conversion of W$_2$ to W, in particular the deprotection of the Z' group when W$_2$ represents —OZ' or of the Z and Z$_2$ groups when W$_2$ represents —NZZ$_2$, making it possible to obtain

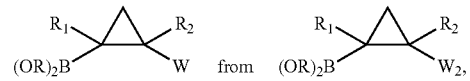

and
a step of conversion of B(OR)$_2$ to —X making it possible to obtain

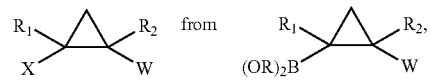

said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$,
or
a step of conversion of B(OR)$_2$ to —X making it possible to obtain

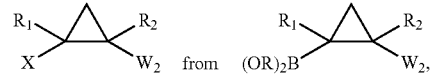

said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$,
and
a step of conversion of W$_2$ to W, in particular the deprotection of the Z' group when W$_2$ represents —OZ' or of the Z and Z$_2$ groups when W$_2$ represents —NZZ$_2$, making it possible to obtain

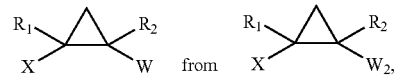

or, when X' represents BF$_3$M, W representing —OH or —NH$_2$,
a step of conversion of W$_2$ to W, in particular the deprotection of the Z' group when W$_2$ represents —OZ' or of the Z and Z$_2$ groups when W$_2$ represents —NZZ$_2$, making it possible to obtain

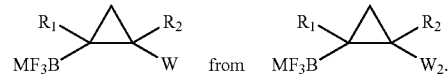

According to an advantageous embodiment, the present invention relates to a process for the preparation of a compound corresponding to formula (I), in which W represents a functional W$_2$ group chosen from —OR$^a$, —OZ', —NR$^a$R$^b$ and —NZZ$_2$, in particular from —OR' and —OZ', said process comprising:

the treatment of a compound of the following formula:

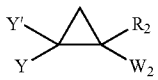

in which $R_2$ is as defined previously,
and in which $W_2$ is as described above, Y being a halide, in particular —Br, Y' being a halide, in particular —Br, or H, by:
  a strong base, in particular butyllithium, more particularly n-butyllithium, then
  a compound of formula X"—B(OR)$_2$, R being as defined above, X" representing H, an O-alkyl group comprising 1 to 14 carbon atoms or an O-aryl group, optionally substituted,
in order to obtain a compound of the following formula:

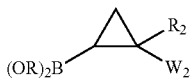

in which R and $W_2$ are as defined above,
or
a reaction of the Simmons-Smith type starting from a compound of the following formula:

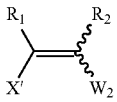

in which $W_2$, $R_1$ and $R_2$ are as defined previously, X' representing B(OR)$_2$ or BF$_3$M, in particular B(OR)$_2$, in which R and M are as defined previously,
in order to obtain a compound of the following formula:

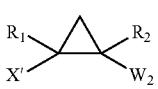

in which $R_1$, $R_2$, X' and $W_2$ are as defined above.
According to an advantageous embodiment, the present invention relates to a process for the preparation of a compound corresponding to formula (I), in which W represents an —OH or —NH$_2$ functional group, in particular —OH:
the treatment of a compound of the following formula:

in which $R_2$ is as defined previously,
and in which $W_2$ represents a functional group chosen from —OR$^a$, —OZ' and —NZZ$_2$, in particular from —OR$^a$ and —OZ', $W_2$ representing in particular —OZ', Y being a halide, in particular —Br, Y' being a halide, in particular —Br, or H, by:
  a strong base, in particular an alkyl lithium, more particularly n-butyllithium or sec-butyllithium, then
  a compound of formula X"—B(OR)$_2$, R being as defined above, X" representing H, an O-alkyl group comprising 1 to 14 carbon atoms or an O-aryl group, optionally substituted,
in order to obtain a compound of the following formula:

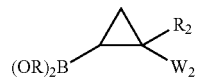

in which R and $W_2$ are as defined above,
or
a reaction of the Simmons-Smith type starting from a compound of the following formula:

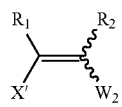

in which $R_1$ and $R_2$ are as defined previously, $W_2$ representing a functional group chosen from —OR$^a$, —OZ' and —NZZ$_2$, in particular from —OR$^a$ and —OZ', $W_2$ representing in particular —OZ', X' representing B(OR)$_2$ or BF$_3$M, in particular B(OR)$_2$, in which R and M are as defined previously,
in order to obtain a compound of the following formula:

in which $R_1$, $R_2$, X' and $W_2$ are as defined above,
said process also comprising the following step, $R_1$ representing in particular H:
  a step of conversion of $W_2$ to W, in particular the deprotection of the Z' group when $W_2$ represents —OZ' or of the Z and $Z_2$ groups when $W_2$ represents —NZZ$_2$, making it possible to obtain

or, when X' represents BF$_3$M,
a step of conversion of $W_2$ to W, in particular the deprotection of the Z' group when $W_2$ represents —OZ' or of the Z and $Z_2$ groups when $W_2$ represents —NZZ$_2$, making it possible to obtain

According to an advantageous embodiment, the present invention relates to a process for the preparation of a compound corresponding to formula (I), in which W represents a functional $W_2$ group chosen from —OR$^a$, —OZ', —NR$^a$R$^b$ and —NZZ$_2$, in particular from —OR$^a$ and —OZ', said process comprising:

the treatment of a compound of the following formula:

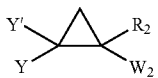

in which $R_2$ is as defined previously,
and in which $W_2$ is as described above, Y being a halide, in particular —Br, Y' being a halide, in particular —Br, or H, by:
- a strong base, in particular an alkyl lithium, more particularly n-butyllithium or sec-butyllithium then
- a compound of formula X"—$B(OR)_2$, R being as defined above, X" representing H, an O-alkyl group comprising 1 to 14 carbon atoms or an O-aryl group, optionally substituted, in order to obtain a compound of the following formula:

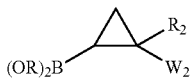

in which R and $W_2$ are as defined above,
or
a reaction of the Simmons-Smith type starting from a compound of the following formula:

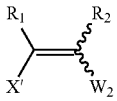

in which $W_2$, $R_1$ and $R_2$ are as defined previously, X' representing $B(OR)_2$ or $BF_3M$, in particular $B(OR)_2$, in which R and M are as defined previously,
in order to obtain a compound of the following formula:

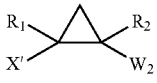

in which $R_1$, $R_2$, X' and $W_2$ are as defined above,
said process also comprising the following step, $R_1$ representing in particular H:
- a step of conversion of $B(OR)_2$ to X, X representing $B(OH)_2$, $BF_3M$ or $B(OR')_3M$, making it possible to obtain

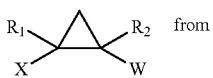 from 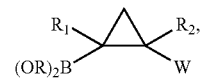

said conversion step being in particular in the presence of $MHF_2$ when X represents $BF_3M$, or in particular a hydrolysis, more particularly in the presence of a mineral, organic base or in the presence of a Lewis acid, when X represents $B(OH)_2$.

According to an advantageous embodiment, the present invention relates to a process for the preparation of a compound corresponding to formula (I), in which W represents a —OH or —$NH_2$ functional group, in particular —OH, said process comprising:

the treatment of a compound of the following formula:

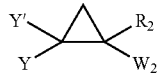

in which $R_2$ is as defined previously,
and in which $W_2$ represents a functional group chosen from —$OR^a$, —OZ' and —$NZZ_2$, in particular from —$OR^a$ and —OZ', $W_2$ representing in particular —OZ', Y being a halide, in particular —Br, Y' being a halide, in particular —Br, or H, by:
- a strong base, in particular butyllithium, more particularly n-butyllithium, then
- a compound of formula X"—$B(OR)_2$, R being as defined above, X" representing H, an O-alkyl group comprising 1 to 14 carbon atoms or an O-aryl group, optionally substituted, in order to obtain a compound of the following formula:

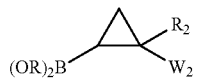

in which R and $W_2$ are as defined above,
or
a reaction of the Simmons-Smith type starting from a compound of the following formula:

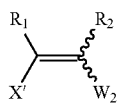

in which $R_1$ and $R_2$ are as defined previously, $W_2$ representing a functional group chosen from —$OR^a$, —OZ' and —$NZZ_2$, in particular from —$OR^a$ and —OZ', $W_2$ representing in particular —OZ', X' representing $B(OR)_2$ or $BF_3M$, in particular $B(OR)_2$, in which R and M are as defined previously,
in order to obtain a compound of the following formula:

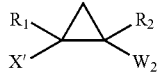

in which $R_1$, $R_2$, X' and $W_2$ are as defined above,
said process also comprising the following steps, $R_1$ representing in particular H:
- a step of conversion of $W_2$ to W, in particular the deprotection of the Z' group when $W_2$ represents —OZ' or of the Z and $Z_2$ groups when $W_2$ represents —$NZZ_2$, making it possible to obtain

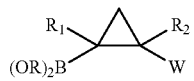 from 

and
a step of conversion of B(OR)$_2$ to X, X representing B(OH)$_2$, BF$_3$M or B(OR')$_3$M, making it possible to obtain

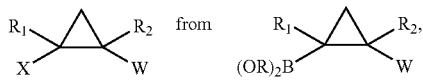

said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$, or a step of conversion of B(OR)$_2$ to X, X representing B(OH)$_2$, BF$_3$M or B(OR')$_3$M, making it possible to obtain

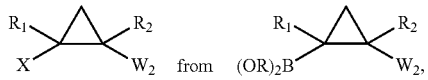

said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$, and a step of conversion of W$_2$ to W, in particular the deprotection of the Z' group when W$_2$ represents —OZ' or of the Z and Z$_2$ groups when W$_2$ represents —NZZ$_2$, making it possible to obtain

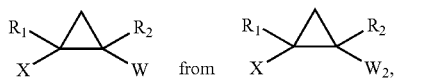

or, when X' represents BF$_3$M, W representing —OH or —NH$_2$, a step of conversion of W$_2$ to W, in particular the deprotection of the Z' group when W$_2$ represents —OZ' or of the Z and Z$_2$ groups when W$_2$ represents —NZZ$_2$, making it possible to obtain

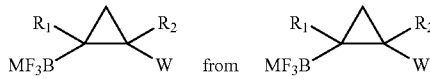

According to an advantageous embodiment, the present invention relates to a process for the preparation of a compound corresponding to formula (I), in which W represents a functional group chosen from —OH, —OR$^a$, —OZ', —NH$_2$, —NHR$^a$, —NR$^a$R$^b$, —NHZ and —NZZ$_2$, in particular from —OH, —OR$^a$ and —OZ', said process comprising:

the treatment of a compound of the following formula:

in which R$_2$ is as defined previously,
and in which W$_2$ represents a functional group chosen from —OR$^a$, —OZ', —NR$^a$R$^b$ and —NZZ$_2$, in particular from —OR$^a$ and —OZ', Y being a halide, in particular —Br, Y' being a halide, in particular —Br, or H, by:
a strong base, in particular an alkyl lithium, more particularly n-butyllithium or sec-butyllithium then
a compound of formula X"—B(OR)$_2$, R being as defined above, X" representing H, an O-alkyl group comprising 1 to 14 carbon atoms or an O-aryl group, optionally substituted,
in order to obtain a compound of the following formula:

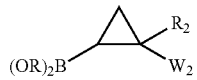

in which R, R$_2$ and W$_2$ are as defined above,
if W represents —OH or —NH$_2$, and/or X is different from B(OR)$_2$, said process also comprising the following steps:
a step of conversion of W$_2$ to W, in particular the deprotection of the Z' group when W$_2$ represents —OZ' or of the Z and Z$_2$ groups when W$_2$ represents —NZZ$_2$, making it possible to obtain

and
a step of conversion of B(OR)$_2$ to —X making it possible to obtain

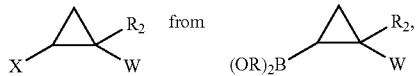

said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$, or
a step of conversion of B(OR)$_2$ to —X making it possible to obtain

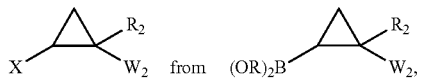

said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$, and a step of conversion of $W_2$ to W, in particular the deprotection of the Z' group when $W_2$ represents —OZ' or of the Z and $Z_2$ groups when $W_2$ represents —$NZZ_2$, making it possible to obtain

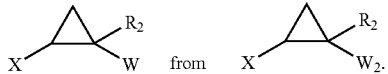

According to an advantageous embodiment, the present invention relates to a preparation process, in which $R_2$ represents H.

According to an advantageous embodiment, the present invention relates to a preparation process, in which $R_2$ represents a linear, cyclic or branched alkyl group comprising 1 to 15 carbon atoms, optionally substituted.

According to an advantageous embodiment, the present invention relates to a process for the preparation of a compound corresponding to formula (I), in which W represents a functional group chosen from —OH, —$OR^a$, —OZ', —$NH_2$, —$NHR^a$, —$NR^aR^b$, —NHZ and —$NZZ_2$, in particular from —OH, —$OR^a$ and —OZ', said process comprising:

a reaction of the Simmons-Smith type starting from a compound of the following formula:

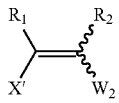

in which $R_1$ and $R_2$ are as defined previously, $W_2$ representing a functional group chosen from —$OR^a$, —OZ', —$NR^aR^b$ and —$NZZ_2$, in particular from —$OR^a$ and —OZ', X' representing $B(OR)_2$ or $BF_3M$, in particular $B(OR)_2$, in which R and M are as defined previously, in order to obtain a compound of the following formula:

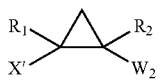

in which $R_1$, $R_2$, X' and $W_2$ are as defined above, if W represents —OH or —$NH_2$, and/or X is different from $B(OR)_2$, said process also comprising the following steps:

when X' represents $B(OR)_2$, a step of conversion of $W_2$ to W, in particular the deprotection of the Z' group when $W_2$ represents —OZ' or of the Z and $Z_2$ groups when $W_2$ represents —$NZZ_2$, making it possible to obtain

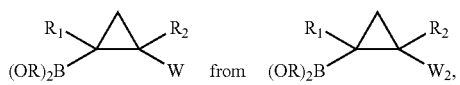

and a step of conversion of $B(OR)_2$ to —X making it possible to obtain

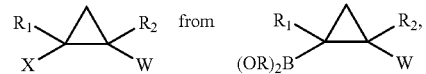

said conversion step being in particular in the presence of $MHF_2$ when X represents $BF_3M$, or in particular a hydrolysis, more particularly in the presence of a mineral, organic base or in the presence of a Lewis acid, when X represents $B(OH)_2$, or a step of conversion of $B(OR)_2$ to —X making it possible to obtain

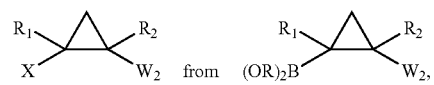

said conversion step being in particular in the presence of $MHF_2$ when X represents $BF_3M$, or in particular a hydrolysis, more particularly in the presence of a mineral, organic base or in the presence of a Lewis acid, when X represents $B(OH)_2$, and a step of conversion of $W_2$ to W, in particular the deprotection of the Z' group when $W_2$ represents —OZ' or of the Z and $Z_2$ groups when $W_2$ represents —$NZZ_2$, making it possible to obtain

or, when X' represents $BF_3M$, W representing —OH or —$NH_2$, a step of conversion of $W_2$ to W, in particular the deprotection of the Z' group when $W_2$ represents —OZ' or of the Z and $Z_2$ groups when $W_2$ represents —$NZZ_2$, making it possible to obtain

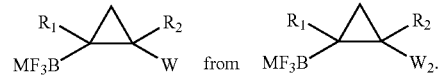

According to an advantageous embodiment, the present invention relates to a preparation process, in which $R_1$ and $R_2$ represent H.

According to an advantageous embodiment, the present invention relates to a preparation process, in which $R_1$ and $R_2$ represent, independently of one another, H or a linear, cyclic or branched alkyl group comprising 1 to 15 carbon atoms, optionally substituted.

According to an advantageous embodiment, the present invention relates to a process for the preparation of a compound corresponding to formula (I), in which W represents a functional group chosen from —OH, —$OR^a$, —OZ', —$NH_2$, —$NHR^a$, —$NR^aR^b$, —NHZ and —$NZZ_2$, in particular from —OH, —$OR^a$ and —OZ', in the form of a racemic trans compound of formula (I-1c):

and its enantiomer, (I-1c)
in which X and W are as defined previously, said process comprising:
the treatment of a compound of the following formula:

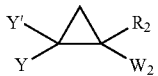

in which $R_2$ is as defined previously,
and in which $W_2$ represents a functional group chosen from —$OR^a$, —OZ', —$NR^aR^b$ and —$NZZ_2$, in particular from —$OR^a$ and —OZ', Y being a halide, in particular —Br, Y' being a halide, in particular —Br, by:
a strong base, in particular an alkyl lithium, more particularly n-butyllithium or sec-butyllithium then
a compound of formula X"—$B(OR)_2$, R being as defined above, X" representing H, an O-alkyl group comprising 1 to 14 carbon atoms or an O-aryl group, optionally substituted,
in order to obtain a compound of the following formula:

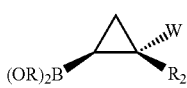

and its enantiomer,
in which R and W are as defined above,
or the following steps:
the treatment of a compound of the following formula:

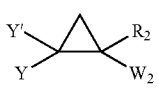

in which $R_2$ is as defined previously,
and in which $W_2$ represents a functional group chosen from —$OR^a$, —OZ', —$NR^aR^b$ and —NHZ, in particular from —$OR^a$ and —OZ', Y being a halide, in particular —Br, Y' being a halide, in particular —Br, by a strong base, in particular butyllithium, more particularly n-butyllithium, in order to obtain a compound of the following formula:

and its enantiomer,
in which W is as defined above, the treatment of the compound of the following formula:

and its enantiomer,
in which W is as defined above,
by:
a strong base, in particular an alkyl lithium, more particularly n-butyllithium or sec-butyllithium, then
a compound of formula X"—$B(OR)_2$, R being as defined above, X" representing H, an O-alkyl group comprising 1 to 14 carbon atoms or an O-aryl group, optionally substituted,
in order to obtain a compound of the following formula:

and its enantiomer,
in which R and W are as defined above,
or the following step:
a reaction of the Simmons-Smith type starting from a compound of the following formula:

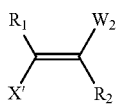

in which $R_1$ and $R_2$ are as defined previously, $W_2$ representing a functional group chosen from —$OR^a$, —OZ', —$NR^aR^b$ and —$NZZ_2$, in particular from —$OR^a$ and —OZ', X' representing $B(OR)_2$ or $BF_3M$, in particular $B(OR)_2$, in which R and M are as defined previously,
in order to obtain a compound of the following formula:

and its enantiomer,
in which $R_1$, $R_2$, X' and $W_2$ are as defined above,
if W represents —OH or —$NH_2$, and/or X is different from $B(OR)_2$, said process also comprising the following steps, $R_1$ representing in particular H:
a step of conversion of $W_2$ to W, in particular the deprotection of the Z' group when $W_2$ represents —OZ' or of the Z and $Z_2$ groups when $W_2$ represents —$NZZ_2$, making it possible to obtain

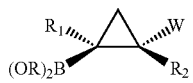

and its enantiomer from

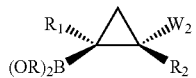

and its enantiomer,
and
a step of conversion of B(OR)$_2$ to —X making it possible to obtain

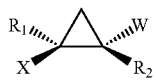

and its enantiomer from

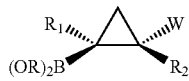

and its enantiomer, said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$,
or
a step of conversion of B(OR)$_2$ to —X making it possible to obtain

and its enantiomer from

and its enantiomer,
said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$, and
a step of conversion of W$_2$ to W, in particular the deprotection of the Z' group when W$_2$ represents —OZ' or of the Z and Z$_2$ groups when W$_2$ represents —NZZ$_2$, making it possible to obtain

and its enantiomer from

and its enantiomer,
or, when X' represents BF$_3$M, W representing —OH or —NH$_2$,
a step of conversion of W$_2$ to W, in particular the deprotection of the Z' group when W$_2$ represents —OZ' or of the Z and Z$_2$ groups when W$_2$ represents —NZZ$_2$, making it possible to obtain

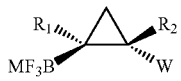

and its enantiomer from

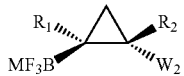

and its enantiomer.

According to an advantageous embodiment, the present invention relates to a process for the preparation of a compound corresponding to formula (I), in which W represents a functional group chosen from —OH, —OR$^a$, —OZ', —NH$_2$, —NHR$^a$, —NR$^a$R$^b$, —NHZ and —NZZ$_2$, in particular from —OH, —OR$^a$ and —OZ',
in the form of a racemic trans compound of formula (I-1b):

and its enantiomer, (I-1b)
in which X and W are as defined previously, said process comprising:
the treatment of a compound of the following formula:

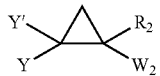

in which R$_2$ is as defined previously,
and in which W$_2$ represents a functional group chosen from —OR$^a$, —OZ', —NR$^a$R$^b$ and —NZZ$_2$, in particular from —OR$^a$ and —OZ', Y being a halide, in particular —Br, Y' being a halide, in particular —Br, by:
a strong base, in particular an alkyl lithium, more particularly n-butyllithium or sec-butyllithium, then
a compound of formula X"—B(OR)$_2$, R being as defined above, X" representing H, an O-alkyl group comprising 1 to 14 carbon atoms or an O-aryl group, optionally substituted, in order to obtain a compound of the following formula:

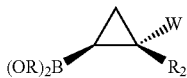

and its enantiomer,
in which R and W are as defined above,
or the following steps:
the treatment of a compound of the following formula:

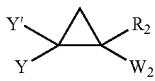

in which $R_2$ is as defined previously,
and in which $W_2$ represents a functional group chosen from $-OR^a$, $-OZ'$, $-NR^aR^b$ and $-NZZ_2$, in particular from $-OR^a$ and $-OZ'$, Y being a halide, in particular $-Br$, Y' being a halide, in particular $-Br$,
by a strong base, in particular an alkyl lithium, more particularly n-butyllithium or sec-butyllithium, in order to obtain a compound of the following formula:

and its enantiomer,
in which W is as defined above,
the treatment of the compound of the following formula:

and its enantiomer,
in which W is as defined above,
by:
  a strong base, in particular an alkyl lithium, more particularly n-butyllithium or sec-butyllithium, then
  a compound of formula X"—B(OR)$_2$, R being as defined above, X" representing H, an O-alkyl group comprising 1 to 14 carbon atoms or an O-aryl group, optionally substituted,
in order to obtain a compound of the following formula:

and its enantiomer,
in which R and W are as defined above,
if W represents $-OH$ or $-NH_2$, and/or X is different from B(OR)$_2$, said process also comprising the following steps:
  a step of conversion of $W_2$ to W, in particular the deprotection of the Z' group when $W_2$ represents $-OZ'$ or of the Z and $Z_2$ groups when $W_2$ represents $-NZZ_2$, making it possible to obtain

and its enantiomer from

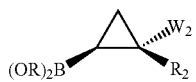

and its enantiomer,
and
a step of conversion of B(OR)$_2$ to $-X$ making it possible to obtain

and its enantiomer from

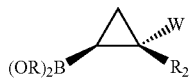

and its enantiomer, said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$, or
a step of conversion of B(OR)$_2$ to $-X$ making it possible to obtain

and its enantiomer from

and its enantiomer,
said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$, and
a step of conversion of $W_2$ to W, in particular the deprotection of the Z' group when $W_2$ represents $-OZ'$ or of the Z and $Z_2$ groups when $W_2$ represents $-NZZ_2$, making it possible to obtain

and its enantiomer from

and its enantiomer, or, when X' represents $BF_3M$, W representing —OH or —$NH_2$, a step of conversion of $W_2$ to W, in particular the deprotection of the Z' group when $W_2$ represents —OZ' or of the Z and $Z_2$ groups when $W_2$ represents —$NZZ_2$, making it possible to obtain

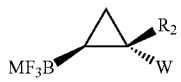

and its enantiomer from

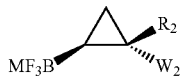

and its enantiomer.

According to an advantageous embodiment, the present invention relates to a process for the preparation of a compound corresponding to formula (I), in which W represents a functional group chosen from —OH, —$OR^a$, —OZ', —$NH_2$, —$NHR^a$, —$NR^aR^b$, —NHZ and —$NZZ_2$, in particular from —OH, —$OR^a$ and —OZ', in the form of a racemic trans compound of formula (I-1c):

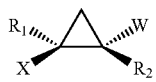

and its enantiomer, (I-1c)

in which X and W are as defined previously, said process comprising:

a step of reaction between a compound of the following formula:

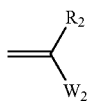

$R_2$ being as defined previously, $W_2$ representing a functional group chosen from —$OR^a$, —OZ', —$NR^aR^b$ and —$NZZ_2$, in particular from —$OR^a$ and —OZ', and a compound of the following formula:

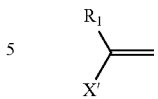

$R_1$ being as defined previously, X' representing $B(OR)_2$ or $BF_3M$, in particular $B(OR)_2$, in the presence of a catalyst comprising a transition metal chosen from the group constituted by nickel, molybdenum, tungsten, ruthenium, in particular molybdenum or ruthenium, said catalyst being more particularly a Shrock catalyst, a $1^{st}$ generation Grubbs catalyst, a $2^{nd}$ generation Grubbs catalyst, or a catalyst of the following formula:

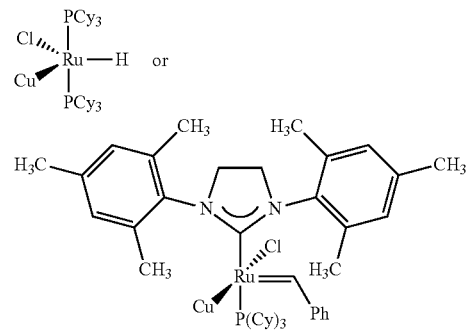

in order to form a compound of the following formula:

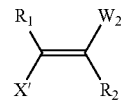

in which $R_1$, $R_2$, X' and $W_2$ are as defined above, a reaction of the Simmons-Smith type starting from a compound of the following formula:

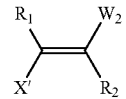

in which $R_1$, $R_2$, X' and $W_2$ are as defined above, in order to obtain a compound of the following formula:

and its enantiomer,
in which $R_1$, $R_2$, X' and $W_2$ are as defined above,
if W represents —OH or —$NH_2$, and/or X is different from $B(OR)_2$, said process also comprising the following steps:
when X' represents $B(OR)_2$,
a step of conversion of $W_2$ to W, in particular the deprotection of the Z' group when $W_2$ represents —OZ' or of the Z and $Z_2$ groups when $W_2$ represents —$NZZ_2$, making it possible to obtain

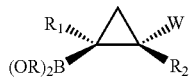

and its enantiomer from

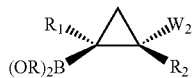

and its enantiomer,
and
a step of conversion of B(OR)$_2$ to —X making it possible to obtain

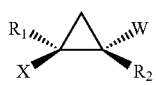

and its enantiomer from

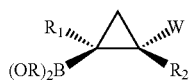

and its enantiomer,
said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$, or
a step of conversion of B(OR)$_2$ to —X making it possible to obtain

and its enantiomer from

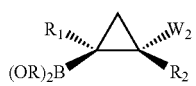

and its enantiomer,
said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$,
and
a step of conversion of W$_2$ to W, in particular the deprotection of the Z' group when W$_2$ represents —OZ' or of the Z and Z$_2$ groups when W$_2$ represents —NZZ$_2$, making it possible to obtain

and its enantiomer from

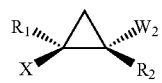

and its enantiomer,
or, when X' represents BF$_3$M, W representing —OH or —NH$_2$,
a step of conversion of W$_2$ to W, in particular the deprotection of the Z' group when W$_2$ represents —OZ' or of the Z and Z$_2$ groups when W$_2$ represents —NZZ$_2$, making it possible to obtain

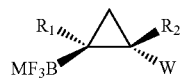

and its enantiomer from

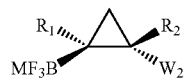

and its enantiomer.

According to an advantageous embodiment, the present invention relates to a process for the preparation of a compound corresponding to formula (I), in which W represents a functional group chosen from —OH, —OR$^a$, —OZ', —NH$_2$, —NHR$^a$, —NR$^a$R$^b$, —NHZ and —NZZ$_2$, in particular from —OH, —OR$^a$ and —OZ', in the form of a racemic cis compound of formula (I-2b):

and its enantiomer, (I-2b)
in which X and W are as defined previously, said process comprising:
a reaction of the Simmons-Smith type starting from a compound of the following formula:

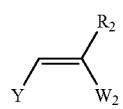

in which Y is as defined previously, W$_2$ representing a functional group chosen from —OR$^a$, —OZ', —NR$^a$R$^b$ and —NZZ$_2$, in particular from —OR$^a$ and —OZ', in order to obtain a compound of the following formula:

and its enantiomer,
in which Y and $W_2$ are as defined above, and
the treatment of a compound of the following formula:

and its enantiomer,
in which Y and $W_2$ are as defined above,
by:
  a strong base, in particular an alkyl lithium, more particularly n-butyllithium or sec-butyllithium, then
  a compound of formula X"—$B(OR)_2$, R being as defined above, X" representing H, an O-alkyl group comprising 1 to 14 carbon atoms or an O-aryl group, optionally substituted,
in order to obtain a compound of the following formula:

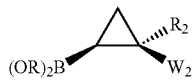

and its enantiomer,
in which R and W are as defined above,
or
the treatment of a compound of the following formula:

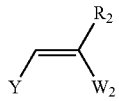

in which Y and $W_2$ are as defined above,
by:
  a strong base, in particular an alkyl lithium, more particularly n-butyllithium or sec-butyllithium, then
  a compound of formula X'—$B(OR)_2$, R being as defined above, X' representing H, an O-alkyl group comprising 1 to 14 carbon atoms or an O-aryl group, optionally substituted,
in order to obtain a compound of the following formula:

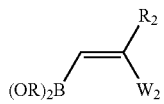

in which R and $W_2$ are as defined above, and
a reaction of the Simmons-Smith type starting from a compound of the following formula:

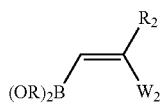

in which Y is as defined previously, $W_2$ representing a functional group chosen from —$OR^a$, —OZ', —$NR^aR^b$ and —$NZZ_2$,
in order to obtain a compound of the following formula:

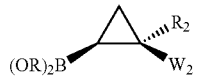

and its enantiomer,
in which R and $W_2$ are as defined above;
if W represents —OH or —$NH_2$, and/or X is different from $B(OR)_2$, said process also comprising the following steps:
  a step of conversion of $W_2$ to W, in particular the deprotection of the Z' group when $W_2$ represents —OZ' or of the Z and $Z_2$ groups when $W_2$ represents —$NZZ_2$, making it possible to obtain

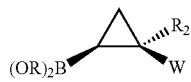

and its enantiomer from

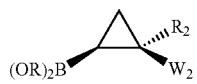

and its enantiomer,
and
a step of conversion of $B(OR)_2$ to —X making it possible to obtain

and its enantiomer from

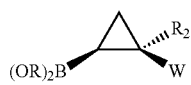

and its enantiomer,
said conversion step being in particular in the presence of $MHF_2$ when X represents $BF_3M$, or in particular a hydrolysis, more particularly in the presence of a mineral, organic base or in the presence of a Lewis acid, when X represents $B(OH)_2$,
or
a step of conversion of $B(OR)_2$ to —X making it possible to obtain

and its enantiomer from

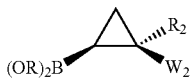

and its enantiomer,
said conversion step being in particular in the presence of MHF$_2$ when X represents BF$_3$M, or in particular a hydrolysis, more particularly in the presence of a mineral, organic base or in the presence of a Lewis acid, when X represents B(OH)$_2$, and
a step of conversion of W$_2$ to W, in particular the deprotection of the Z' group when W$_2$ represents —OZ' or of the Z and Z$_2$ groups when W$_2$ represents —NZZ$_2$, making it possible to obtain

and its enantiomer from

and its enantiomer.

The invention also relates to a compound corresponding to the following formula (I)

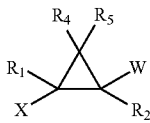

in which:
X represents a substituted boron atom chosen from the group comprising B(OH)$_2$, B(OR)$_2$, BF$_3$M, B(OR')$_3$M in which:
R is an alkyl group comprising 1 to 14 carbon atoms, an aryl group, optionally substituted, or is such that (OR)$_2$ forms a ring between the two oxygen atoms, (OR)$_2$ being in particular chosen from the group comprising the bivalent radicals deriving from diols, such as O—CH$_2$—CH$_2$—O, O—CH$_2$—CH$_2$—CH$_2$—O, O—CH$_2$—C(CH$_3$)$_2$—CH$_2$—O, O—C(CH$_3$)$_2$—CH$_2$—CH$_2$—C(CH$_3$)$_2$—O, O—CH(CH$_3$)—CH$_2$—CH$_2$—CH(CH$_3$)—O, O—CH(Ph)-CH(Ph)-O, O—CH(CH$_3$)—CH$_2$—C(CH$_3$)$_2$—O, O-o-Ph-O, O—CH$_2$—CH$_2$—NH—CH$_2$—CH$_2$—O, O—CH$_2$—CH$_2$—N(CH$_2$—CH$_2$—CH$_2$—CH$_3$)—CH$_2$—CH$_2$—O, O—CH(COOH)—CH(COOH)—O and its esters, and the bivalent radicals deriving from diacids, such as OCO—CH$_2$—N(CH$_3$)—CH$_2$—COO,
R' is an alkyl group comprising 1 to 14 carbon atoms or is such that:
(OR')$_3$ forms a ring between two of the oxygen atoms, (OR')$_3$ then being in the form OR'(OR)$_2$, where R' is an alkyl group comprising 1 to 14 carbon atoms and (OR)$_2$ is as defined above, or
(OR')$_3$ forms a bicycle between the three oxygen atoms, (OR')$_3$ being in particular chosen from the group comprising the trivalent radicals deriving from triols, such as H$_3$C—C—(CH$_2$—O)$_3$,
M represents the lithium Li$^+$ ion, the sodium Na$^+$ ion, the potassium K$^+$ ion, the caesium Cs$^+$ ion, the ammonium R$^c$R$^d$R$^e$R$^f$N$^+$ ion where R$^c$, R$^d$ R$^e$, R$^f$ are chosen from H or a saturated carbon-containing chain comprising in particular 1 to 6 carbon atoms chosen independently of one another,
and in particular X represents B(OH)$_2$, B(OR)$_2$ or BF$_3$K,
R$_1$, R$_4$ and R$_5$, identical or different, are chosen from the group constituted by:
1. H
2. the aryls comprising rings with 6 to 15 carbon atoms, optionally substituted;
3. the heterocycles or heteroaryls comprising rings with 2 to 15 carbon atoms, optionally substituted;
4. the linear or branched alkenyls comprising 1 to 12 carbon atoms, optionally substituted, or carbon rings comprising 3 to 12 carbon atoms and one or more C=C double bonds, optionally substituted;
5. the linear or branched alkynyls comprising 1 to 15 carbon atoms, optionally substituted;
6. the linear, cyclic or branched alkyl groups comprising 1 to 15 carbon atoms, optionally substituted;
R$_1$ and R$_4$, or R$_1$ and R$_5$ being able to form a ring with 5, 6, or 7 members optionally comprising a heteroatom chosen from oxygen, nitrogen and sulphur, said ring being able to be substituted;
R$_2$ is chosen from the group constituted by the groups being able to be represented by R$_1$, R$_4$ or R$_5$, as well as —COR$^a$, —COOR$^a$, —CONH$_2$, —CONHR$^a$, —CONR$^a$R$^b$, —CN and —NO$_2$,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;
R$^a$ and R$^b$ being able to be linked in order to form a ring, optionally substituted,
W represents a functional group chosen from —CHO, —COR$^a$, —COOH, —COOR$^a$, —CONH$_2$, —CONHR$^a$, —CONR$^a$R$^b$, —CH$_2$OH, —CH$_2$OR$^a$, —CHR$^b$OH, —CHR$^b$OR$^a$, —CR$^b$R$^{b'}$OH, —CR$^b$R$^{b'}$OR$^a$, —CH$_2$NH$_2$, —CH$_2$NHZ, —CHR$^a$NHZ, —OH, —OR$^a$, —OZ', —NH$_2$, —NHR$^a$, —NR$^a$R$^b$, —NHZ and —NZZ$_2$,
in which Z and Z$_2$ represent a protective group of an amine function, and Z' represents a protective group of an alcohol function, and
in which R$^a$, R$^b$ and R$^{b'}$, identical or different, represent linear, cyclic or branched, aromatic, or aromatic or non-aromatic heterocyclic alkyl, alkenyl, alkynyl groups comprising 1 to 15 carbon atoms, optionally substituted;
provided that:
when R$_1$, R$_2$, R$_4$ and R$_5$ represent H and B represents B(OH)$_2$, B(OR)$_2$, or B(OR')$_3$M, then
W is chosen from —COR$^a$, —CONH$_2$, —CONHR$^a$, —CONR$^a$R$^b$, —OH, —OR$^a$ and —OZ',
when R$_1$, R$_2$, R$_4$ and R$_5$ represent H and B represents BF$_3$M, then W is chosen from —COOH, —COOR$^a$, —CHO, —COR$^a$—CONH$_2$, —CONHR$^a$, —CONR$^a$R$^b$, —OH, —OR$^a$ and —OZ', when W represents CH₂OH, —CH₂ORᵃ, —CHRᵇOH, —CHRᵇORᵃ, —CRᵇRᵇ'OH, or —CRᵇRᵇ'ORᵃ, and B represents B(OH)₂, B(OR)₂, or B(OR')₃M, then:
R₁ does not represent H, or
R₂ and R₄ do not represent H, or
R₂ and R₅ do not represent H.
when W represents CH₂OH, —CH₂ORᵃ, —CHRᵇOH, —CHRᵇORᵃ, —CRᵇRᵇ'OH, or —CRᵇRᵇ'ORᵃ, and B represents BF₃M, then R₁ or R₂ do not represent H.
when W represents —COOH or —COORᵃ, and B represents B(OH)₂, B(OR)₂, or B(OR')₃M, then:
R₁ does not represent H, or
R₂ and R₄ do not represent H, or
R₂ and R₅ do not represent H.

According to an advantageous embodiment, the present invention relates to a compound in which W represents a functional group chosen from —CHO, —CORᵃ, —COOH, —COORᵃ, —CONH₂, —CONHRᵃ, —CONRᵃRᵇ, —CH₂OH, —CH₂ORᵃ, —CHRᵇOH, —CHRᵇORᵃ, —CRᵇRᵇ'OH, —CRᵇRᵇ'ORᵃ, —CH₂NH₂, —CH₂NHZ, —CHRᵃNHZ.

According to an advantageous embodiment, the present invention relates to a compound in which W represents a functional group chosen from —CHO, —CORᵃ, —COOH, —COORᵃ, —CONH₂, —CONHRᵃ, —CONRᵃRᵇ, —CH₂OH, —CH₂ORᵃ, —CHRᵇOH, —CHRᵇORᵃ, —CRᵇRᵇ'OH, —CRᵇRᵇ'ORᵃ.

According to an advantageous embodiment, the present invention relates to a compound in which W represents a functional group chosen from —CHO, —CORᵃ, —COOH, —COORᵃ, —CONH₂, —CONHRᵃ, —CONRᵃRᵇ.

According to an advantageous embodiment, the present invention relates to a compound in which W represents a functional group chosen from —CONH—SO₂-cyclopropyl, —CH₂—NH—CO—CH₂—CH₃ and the group of the following formula:

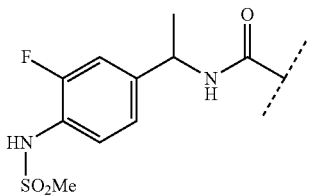

According to an advantageous embodiment, the present invention relates to a compound in which R₂ represents H.

According to an advantageous embodiment, the present invention relates to a compound in which R₂ is chosen from the group constituted by the —CORᵃ, —COORᵃ, —CONH₂, —CONHRᵃ, —CONRᵃRᵇ, —CN and —NO₂ groups,
in which Rᵃ and Rᵇ, identical or different, represent linear, cyclic or branched, aromatic, or aromatic or non-aromatic heterocyclic alkyl, alkenyl, alkynyl groups comprising 1 to 15 carbon atoms, optionally substituted;
Rᵃ and Rᵇ being able to be linked in order to form a ring, optionally substituted.

According to an advantageous embodiment, the present invention relates to a compound in which R₁, R₄ and R₅ represent H, an aryl, a heterocycle, a heteroaryl or an alkyl as defined previously.

According to an advantageous embodiment, the present invention relates to a compound in which R₁, R₂, R₄ and R₅ represent H.

According to an advantageous embodiment, the present invention relates to a compound in which W represents a functional group chosen from —OH, —ORᵃ, —OZ', —NH₂, —NHRᵃ, —NRᵃRᵇ, —NHZ and —NZZ₂, R₁, R₂, R₄ and R₅ representing in particular H.

According to an advantageous embodiment, the present invention relates to a compound in which R₄ and R₅ represent H.

According to an advantageous embodiment, the present invention relates to a compound in which R₁, R₄ and R₅ represent H.

According to an advantageous embodiment, the present invention relates to a compound in which R₂, R₄ and R₅ represent H.

According to an advantageous embodiment, the present invention relates to a compound in which R₁, R₂, R₄ and R₅ represent H.

According to an advantageous embodiment, the present invention relates to a compound in which R₁ and R₂ represent, independently of one another, H or a linear, cyclic or branched alkyl group comprising 1 to 15 carbon atoms, optionally substituted.

According to an advantageous embodiment, the present invention relates to a compound in which R₂ represents H or a linear, cyclic or branched alkyl group comprising 1 to 15 carbon atoms, optionally substituted.

According to an advantageous embodiment, the present invention relates to a compound corresponding to the following formula (I-A)

(I-A)

in which:
X represents a substituted boron atom chosen from the group comprising B(OH)₂, B(OR)₂, BF₃M, B(OR')₃M
in which:
R is an alkyl group comprising 1 to 14 carbon atoms, an aryl group, optionally substituted, or is such that (OR)₂ forms a ring between the two oxygen atoms, (OR)₂ being in particular chosen from the group comprising the bivalent radicals deriving from diols, such as O—CH₂—CH₂—O, O—CH₂—CH₂—CH₂—O, O—CH₂—C(CH₃)₂—CH₂—O, O—C(CH₃)₂—CH₂—CH₂—C(CH₃)₂—O, O—CH(CH₃)—CH₂—CH₂—CH(CH₃)—O, O—CH(Ph)-CH(Ph)-O, O—CH(CH₃)—CH₂—C(CH₃)₂—O, O-o-Ph-O, O—CH₂—CH₂—NH—CH₂—CH₂—O, O—CH₂—CH₂—N(CH₂—CH₂—CH₂—CH₃)—CH₂—CH₂—O, O—CH(COOH)—CH(COOH)—O and its esters, and the bivalent radicals deriving from diacids, such as OCO—CH₂—N(CH₃)—CH₂—COO,
R' is an alkyl group comprising 1 to 14 carbon atoms or is such that:
(OR')₃ forms a ring between two of the oxygen atoms, (OR')₃ then being in the form OR'(OR)₂, where R' is an alkyl group comprising 1 to 14 carbon atoms and (OR)₂ is as defined above, or
(OR')₃ forms a bicycle between the three oxygen atoms, (OR')₃ being in particular chosen from the group comprising the trivalent radicals deriving from triols, such as H₃C—C—(CH₂—O)₃, M represents the lithium Li$^+$ ion, the sodium Na$^+$ ion, the potassium K$^+$ ion, the caesium Cs$^+$ ion, the ammonium R$^c$R$^d$R$^e$R$^f$N$^+$ ion where R$^c$, R$^d$ R$^e$, R$^f$ are chosen from H or a saturated carbon-containing chain comprising in particular 1 to 6 carbon atoms chosen independently of one another, and in particular X represents B(OH)$_2$, B(OR)$_2$ or BF$_3$K, R$_1$ and R$_4$, identical or different, are chosen from the group constituted by:

1. H
2. the aryls comprising rings with 6 to 15 carbon atoms, optionally substituted;
3. the heterocycles or heteroaryls comprising rings with 2 to 15 carbon atoms, optionally substituted;
4. the linear or branched alkenyls comprising 1 to 12 carbon atoms, optionally substituted, or carbon rings comprising 3 to 12 carbon atoms and one or more C=C double bonds, optionally substituted;
5. the linear or branched alkynyls comprising 1 to 15 carbon atoms, optionally substituted;
6. the linear, cyclic or branched alkyl groups comprising 1 to 15 carbon atoms, optionally substituted;

at least one of the R$_1$ and R$_4$ groups representing H,

R$_2$ is chosen from the group constituted by the groups being able to be represented by R$_1$ or R$_4$, as well as —COR$^a$, —COOR$^a$, —CONH$_2$, —CONHR$^a$, —CONR$^a$R$^b$, —CN and —NO$_2$, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;

R$^a$ and R$^b$ being able to be linked in order to form a ring, optionally substituted, W represents a functional group chosen from —CHO, —COR$^a$, —COOH, —COOR$^a$, —CONH$_2$, —CONHR$^a$, —CONR$^a$R$^b$, —CONH—SO$_2$—R$^a$, —CH$_2$OH, —CH$_2$OR$^a$, —CHR$^b$OH, —CHR$^b$OR$^a$, —CR$^b$R$^{b'}$OH, —CR$^b$R$^{b'}$OR$^a$, —CH$_2$NH$_2$, —CH$_2$NHZ, —CHR$^a$NHZ, —CH$_2$—NH—COR$^a$, in which Z represents a protective group of an amine function, and in which R$^a$, R$^b$ and R$^{b'}$, identical or different, represent linear, cyclic or branched, aromatic, or aromatic or non-aromatic heterocyclic alkyl, alkenyl, alkynyl groups comprising 1 to 15 carbon atoms, optionally substituted;

provided that:

when R$_1$, R$_2$ and R$_4$ represent H and B represents B(OH)$_2$, B(OR)$_2$, or B(OR')$_3$M, then W is chosen from —COR$^a$, —CONH$_2$, —CONHR$^a$, —CONR$^a$R$^b$, when R$_1$, R$_2$ and R$_4$ represent H and B represents BF$_3$M, then W is chosen from —COOH, —COOR$^a$, —CHO, —COR$^a$—CONH$_2$, —CONHR$^a$, —CONR$^a$R$^b$, when W represents CH$_2$OH, —CH$_2$OR$^a$, —CHR$^b$OH, —CHR$^b$OR$^a$, —CR$^b$R$^{b'}$OH, or —CR$^b$R$^{b'}$OR$^a$, and B represents B(OH)$_2$, B(OR)$_2$, or B(OR')$_3$M, then:
R$_1$ does not represent H, or
R$_2$ and R$_4$ do not represent H, when W represents CH$_2$OH, —CH$_2$OR$^a$, —CHR$^b$OH, —CHR$^b$OR$^a$, —CR$^b$R$^{b'}$OH, or —CR$^b$R$^{b'}$OR$^a$, and B represents BF$_3$M, then R$_1$ or R$_2$ do not represent H.

when W represents —COOH or —COOR$^a$, and B represents B(OH)$_2$, B(OR)$_2$, or B(OR')$_3$M, then:
R$_1$ does not represent H, or
R$_2$ and R$_4$ do not represent H.

According to an advantageous embodiment, the present invention relates to a compound corresponding to the following formula (I-B)

(I-B)

in which:

M represents the lithium Li$^+$ ion, the sodium Na$^+$ ion, the potassium K$^+$ ion, the caesium Cs$^+$ ion, the ammonium R$^c$R$^d$R$^e$R$^f$N$^+$ ion where R$^c$, R$^d$ R$^e$, R$^f$ are chosen from H or a saturated carbon-containing chain comprising in particular 1 to 6 carbon atoms chosen independently of one another, BF$_3$M representing in particular BF$_3$K, R$_1$ and R$_4$, identical or different, are chosen from the group constituted by:

1. H
2. the aryls comprising rings with 6 to 15 carbon atoms, optionally substituted;
3. the heterocycles or heteroaryls comprising rings with 2 to 15 carbon atoms, optionally substituted;
4. the linear or branched alkenyls comprising 1 to 12 carbon atoms, optionally substituted, or carbon rings comprising 3 to 12 carbon atoms and one or more C=C double bonds, optionally substituted;
5. the linear or branched alkynyls comprising 1 to 15 carbon atoms, optionally substituted;
6. the linear, cyclic or branched alkyl groups comprising 1 to 15 carbon atoms, optionally substituted;

at least one of the R$_1$ and R$_4$ groups representing H,

R$_2$ is chosen from the group constituted by the groups being able to be represented by R$_1$ or R$_4$, as well as —COR$^a$, —COOR$^a$, —CONH$_2$, —CONHR$^a$, —CONR$^a$R$^b$, —CN and —NO$_2$, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;

R$^a$ and R$^b$ being able to be linked in order to form a ring, optionally substituted, W represents a functional group chosen from —CHO, —COR$^a$, —COOH, —COOR$^a$, —CONH$_2$, —CONHR$^a$, —CONR$^a$R$^b$, —CONH—SO$_2$—R$^a$, —CH$_2$OH, —CH$_2$OR$^a$, —CHR$^b$OH, —CHR$^b$OR$^a$, —CR$^b$R$^{b'}$OH, —CR$^b$R$^{b'}$OR$^a$, —CH$_2$NH$_2$, —CH$_2$NHZ, —CHR$^a$NHZ, —CH$_2$—NH—COR$^a$, in which Z represents a protective group of an amine function, and in which R$^a$, R$^b$ and R$^{b'}$, identical or different, represent linear, cyclic or branched, aromatic, or aromatic or non-aromatic heterocyclic alkyl, alkenyl, alkynyl groups comprising 1 to 15 carbon atoms, optionally substituted;

provided that:

when R$_1$, R$_2$ and R$_4$ represent H, then W is chosen from —COOH, —COOR$^a$, —CHO, —COR$^a$—CONH$_2$, —CONHR$^a$, —CONR$^a$R$^b$, when W represents CH$_2$OH, —CH$_2$OR$^a$, —CHR$^b$OH, —CHR$^b$OR$^a$, —CR$^b$R$^{b'}$OH, or —CR$^b$R$^{b'}$OR$^a$, then R$_1$ or R$_2$ do not represent H.

According to an advantageous embodiment, the present invention relates to a compound of formula (I-A) or (I-B) in which W represents a functional group chosen from —CHO, —COR$^a$, —COOH, —COOR$^a$, —CONH$_2$, —CONHR$^a$, —CONR$^a$R$^b$, —CONH—SO$_2$—R$^a$.

According to an advantageous embodiment, the present invention relates to a compound of formula (I-A) or (I-B) in which W represents a functional group chosen from —CHO, —COR$^a$, —COOH and —COOR$^a$, W representing in particular —COOR$^a$.

According to an advantageous embodiment, the present invention relates to a compound of formula (I-A) or (I-B) in which W represents a functional group chosen from —CONH—SO$_2$-cyclopropyl, —CH$_2$—NH—CO—CH$_2$—CH$_3$ and the group of the following formula:

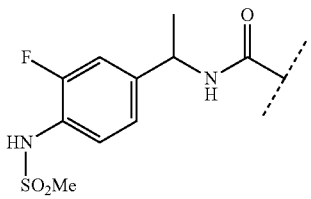

According to an advantageous embodiment, the present invention relates to a compound of formula (I-A) or (I-B) in which R$_2$ represents H.

According to an advantageous embodiment, the present invention relates to a compound of formula (I-A) or (I-B) in which R$_2$ is chosen from the group constituted by the —COR$^a$, —COOR$^a$, —CONH$_2$, —CONHR$^a$, —CONR$^a$R$^b$ and —NO$_2$ groups,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;
R$^a$ and R$^b$ being able to be linked in order to form a ring, optionally substituted.

According to an advantageous embodiment, the present invention relates to a compound of formula (I-A) or (I-B) in which R$_1$, R$_2$ and R$_4$ represent H.

According to an advantageous embodiment, the present invention relates to a compound of formula (I-A) or (I-B) in which R$_1$ represents H.

According to an advantageous embodiment, the present invention relates to a compound of formula (I-A) or (I-B) in which R$_1$ represents H and R$_4$ represents an aryl, a heterocycle, a heteroaryl or an alkyl as defined previously.

According to an advantageous embodiment, the present invention relates to a compound of formula (I-A) or (I-B) in which R$_4$ represents H.

According to an advantageous embodiment, the present invention relates to a compound of formula (I-A) or (I-B) in which R$_4$ represents H and R1 represents an aryl, a heterocycle, a heteroaryl or an alkyl as defined previously.

According to an advantageous embodiment, the present invention relates to a compound of formula (I-A) or (I-B) in which R$_1$ and R$_2$ represent H and R$_4$ represents an aryl, a heterocycle, a heteroaryl or an alkyl as defined previously.

According to an advantageous embodiment, the present invention relates to a compound of formula (I-A) or (I-B) in which R$_2$ and R$_4$ represent H and R$_1$ represents an aryl, a heterocycle, a heteroaryl or an alkyl as defined previously.

According to an advantageous embodiment, the present invention relates to a compound of formula (I-A) or (I-B) in which R$_1$ represents H, R$_4$ represents an aryl, a heterocycle, a heteroaryl or an alkyl as defined previously, and R$_2$ is chosen from the group constituted by the —COR$^a$, —COOR$^a$, —CONH$_2$, —CONHR$^a$, —CONR$^a$R$^b$ and —NO$_2$ groups,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;
R$^a$ and R$^b$ being able to be linked in order to form a ring, optionally substituted.

According to an advantageous embodiment, the present invention relates to a compound of formula (I-A) or (I-B) in which R$_4$ represents H, R$_1$ represents an aryl, a heterocycle, a heteroaryl or an alkyl as defined previously, and R$_2$ is chosen from the group constituted by the —COR$^a$, —COOR$^a$, —CONH$_2$, —CONHR$^a$, —CONR$^a$R$^b$ and —NO$_2$ groups,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;
R$^a$ and R$^b$ being able to be linked in order to form a ring, optionally substituted.

According to an advantageous embodiment, the present invention relates to a compound of formula (I-A) or (I-B) in which R$_1$ and R$_4$ represent H, and R$_2$ is chosen from the group constituted by the —COR$^a$, —COOR$^a$, —CONH$_2$, —CONHR$^a$, —CONR$^a$R$^b$ and —NO$_2$ groups,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;
R$^a$ and R$^b$ being able to be linked in order to form a ring, optionally substituted.

According to an advantageous embodiment, the present invention relates to a compound corresponding to the following formula (I-C)

(I-C)

in which:
X represents a substituted boron atom chosen from the group comprising B(OH)$_2$, B(OR)$_2$, BF$_3$M, B(OR')$_3$M in which:
R is an alkyl group comprising 1 to 14 carbon atoms, an aryl group, optionally substituted, or is such that (OR)$_2$ forms a ring between the two oxygen atoms, (OR)$_2$ being in particular chosen from the group comprising the bivalent radicals deriving from diols, such as O—CH$_2$—CH$_2$—O, O—CH$_2$—CH$_2$—CH$_2$—O, O—CH$_2$—C(CH$_3$)$_2$—CH$_2$—O, O—C(CH$_3$)$_2$—CH$_2$—CH$_2$—C(CH$_3$)$_2$—O, O—CH(CH$_3$)—CH$_2$—CH$_2$—CH(CH$_3$)—O, O—CH(Ph)-CH(Ph)-O, O—CH(CH$_3$)—CH$_2$—C(CH$_3$)$_2$—O, O-o-Ph-O, O—CH$_2$—CH$_2$—NH—CH$_2$—CH$_2$—O, O—CH$_2$—CH$_2$—N(CH$_2$—CH$_2$—CH$_2$—CH$_3$)—CH$_2$—CH$_2$—O, O—CH(COOH)—CH(COOH)—O and its esters, and the bivalent radicals deriving from diacids, such as OCO—CH$_2$—N(CH$_3$)—CH$_2$—COO, R' is an alkyl group comprising 1 to 14 carbon atoms or is such that:

(OR')$_3$ forms a ring between two of the oxygen atoms, (OR')$_3$ then being in the form OR'(OR)$_2$, where R' is an alkyl group comprising 1 to 14 carbon atoms and (OR)$_2$ is as defined above, or (OR')$_3$ forms a bicycle between the three oxygen atoms, (OR')$_3$ being in particular chosen from the group comprising the trivalent radicals deriving from triols, such as H$_3$C—C—(CH$_2$—O)$_3$, M represents the lithium Li$^+$ ion, the sodium Na$^+$ ion, the potassium K$^+$ ion, the caesium Cs$^+$ ion, the ammonium R$^c$R$^d$R$^e$R$^f$N$^+$ ion where R$^c$, R$^d$ R$^2$, R$^f$ are chosen from H or a saturated carbon-containing chain comprising in particular 1 to 6 carbon atoms chosen independently of one another, and in particular X represents B(OH)$_2$, B(OR)$_2$ or BF$_3$K, R$_1$ and R$_4$, identical or different, are chosen from the group constituted by:

1. H
2. the aryls comprising rings with 6 to 15 carbon atoms, optionally substituted;
3. the heterocycles or heteroaryls comprising rings with 2 to 15 carbon atoms, optionally substituted;
4. the linear or branched alkenyls comprising 1 to 12 carbon atoms, optionally substituted, or carbon rings comprising 3 to 12 carbon atoms and one or more C=C double bonds, optionally substituted;
5. the linear or branched alkynyls comprising 1 to 15 carbon atoms, optionally substituted;
6. the linear, cyclic or branched alkyl groups comprising 1 to 15 carbon atoms, optionally substituted;

at least one of the R$_1$ and R$_4$ groups representing H,

R$_2$ is chosen from the group constituted by H and the —COR$^a$, —COOR$^a$, —CONH$_2$, —CONHR$^a$, —CONR$^a$R$^b$ and —NO$_2$ groups, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;

R$^a$ and R$^b$ being able to be linked in order to form a ring, optionally substituted, W represents a functional group chosen from —CHO, —COR$^a$, —COOH, —COOR$^a$, —CONH$_2$, —CONHR$^a$, —CONR$^a$R$^b$, in which R$^a$, R$^b$ and R$^{b'}$, identical or different, represent linear, cyclic or branched, aromatic, or aromatic or non-aromatic heterocyclic alkyl, alkenyl, alkynyl groups comprising 1 to 15 carbon atoms, optionally substituted;

provided that:

when R$_1$, R$_2$ and R$_4$ represent H and B represents B(OH)$_2$, B(OR)$_2$, or B(OR')$_3$M, then W is chosen from —COR$^a$, —CONH$_2$, —CONHR$^a$, —CONR$^a$R$^b$, when W represents —COOH or —COOR$^a$, and B represents B(OH)$_2$, B(OR)$_2$, or B(OR')$_3$M, then:

R$_1$ does not represent H, or

R$_2$ and R$_4$ do not represent H.

According to an advantageous embodiment, the present invention relates to a compound corresponding to the following formula (I-D)

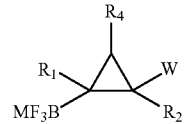

(I-D)

in which:

M represents the lithium Li$^+$ ion, the sodium Na$^+$ ion, the potassium K$^+$ ion, the caesium Cs$^+$ ion, the ammonium R$^c$R$^d$R$^e$R$^f$N$^+$ ion where R$^c$, R$^d$ R$^e$, R$^f$ are chosen from H or a saturated carbon-containing chain comprising in particular 1 to 6 carbon atoms chosen independently of one another, BF$_3$M representing in particular BF$_3$K, R$_1$ and R$_4$, identical or different, are chosen from the group constituted by:

1. H
2. the aryls comprising rings with 6 to 15 carbon atoms, optionally substituted;
3. the heterocycles or heteroaryls comprising rings with 2 to 15 carbon atoms, optionally substituted;
4. the linear or branched alkenyls comprising 1 to 12 carbon atoms, optionally substituted, or carbon rings comprising 3 to 12 carbon atoms and one or more C=C double bonds, optionally substituted;
5. the linear or branched alkynyls comprising 1 to 15 carbon atoms, optionally substituted;
6. the linear, cyclic or branched alkyl groups comprising 1 to 15 carbon atoms, optionally substituted;

at least one of the R$_1$ and R$_4$ groups representing H,

R$_2$ is chosen from the group constituted by H and the —COR$^a$, —COOR$^a$, —CONH$_2$, —CONHR$^a$, —CONR$^a$R$^b$ and —NO$_2$ groups, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;

R$^a$ and R$^b$ being able to be linked in order to form a ring, optionally substituted, W represents a functional group chosen from —CHO, —COR$^a$, —COOH, —COOR$^a$, —CONH$_2$, —CONHR$^a$, —CONR$^a$R$^b$, in which R$^a$, R$^b$ and R$^{b'}$, identical or different, represent linear, cyclic or branched, aromatic, or aromatic or non-aromatic heterocyclic alkyl, alkenyl, alkynyl groups comprising 1 to 15 carbon atoms, optionally substituted.

According to an advantageous embodiment, the present invention relates to a compound of formula (I-C) or (I-D) in which W represents a functional group chosen from —CHO, —COR$^a$, —COOH and —COOR$^a$, W representing in particular —COOR$^a$.

According to an advantageous embodiment, the present invention relates to a compound of formula (I-C) or (I-D) in which R$_2$ represents H.

According to an advantageous embodiment, the present invention relates to a process for the preparation of a compound of formula (I-C) or (I-D) in which R$_2$ is chosen from the group constituted by the —COOR$^a$, —CONH$_2$, —CONHR$^a$ and —CONR$^a$R$^b$ groups, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;

R$^a$ and R$^b$ being able to be linked in order to form a ring, optionally substituted.

According to an advantageous embodiment, the present invention relates to a compound of formula (I-C) or (I-D) in which $R_1$, $R_2$ and $R_4$ represent H.

According to an advantageous embodiment, the present invention relates to a compound of formula (I-C) or (I-D) in which $R_1$ represents H.

According to an advantageous embodiment, the present invention relates to a compound of formula (I-C) or (I-D) in which $R_1$ represents H and $R_4$ represents an aryl, a heterocycle, a heteroaryl or an alkyl as defined previously.

According to an advantageous embodiment, the present invention relates to a compound of formula (I-C) or (I-D) in which $R_4$ represents H.

According to an advantageous embodiment, the present invention relates to a compound of formula (I-C) or (I-D) in which $R_4$ represents H and $R_1$ represents an aryl, a heterocycle, a heteroaryl or an alkyl as defined previously.

According to an advantageous embodiment, the present invention relates to a compound of formula (I-C) or (I-D) in which $R_1$ and $R_2$ represent H and $R_4$ represents an aryl, a heterocycle, a heteroaryl or an alkyl as defined previously.

According to an advantageous embodiment, the present invention relates to a compound of formula (I-C) or (I-D) in which $R_2$ and $R_4$ represent H and $R_1$ represents an aryl, a heterocycle, a heteroaryl or an alkyl as defined previously.

According to an advantageous embodiment, the present invention relates to a compound of formula (I-C) or (I-D) in which $R_1$ represents H, $R_4$ represents an aryl, a heterocycle, a heteroaryl or an alkyl as defined previously, and $R_2$ is chosen from the group constituted by the —COR$^a$, —COOR$^a$, —CONH$_2$, —CONHR$^a$, —CONR$^a$R$^b$ and —NO$_2$ groups,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;
R$^a$ and R$^b$ being able to be linked in order to form a ring, optionally substituted.

According to an advantageous embodiment, the present invention relates to a compound of formula (I-C) or (I-D) in which $R_4$ represents H, $R_1$ represents an aryl, a heterocycle, a heteroaryl or an alkyl as defined previously, and $R_2$ is chosen from the group constituted by the —COR$^a$, —COOR$^a$, —CONH$_2$, —CONHR$^a$, —CONR$^a$R$^b$ and —NO$_2$ groups,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;
R$^a$ and R$^b$ being able to be linked in order to form a ring, optionally substituted.

According to an advantageous embodiment, the present invention relates to a compound of formula (I-C) or (I-D) in which $R_1$ and $R_4$ represent H, and $R_2$ is chosen from the group constituted by the —COR$^a$, —COOR$^a$, —CONH$_2$, —CONHR$^a$, —CONR$^a$R$^b$ and —NO$_2$ groups,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;
R$^a$ and R$^b$ being able to be linked in order to form a ring, optionally substituted.

According to an advantageous embodiment, the present invention relates to a compound chosen from the group constituted by the compounds of the following formula and their enantiomer:

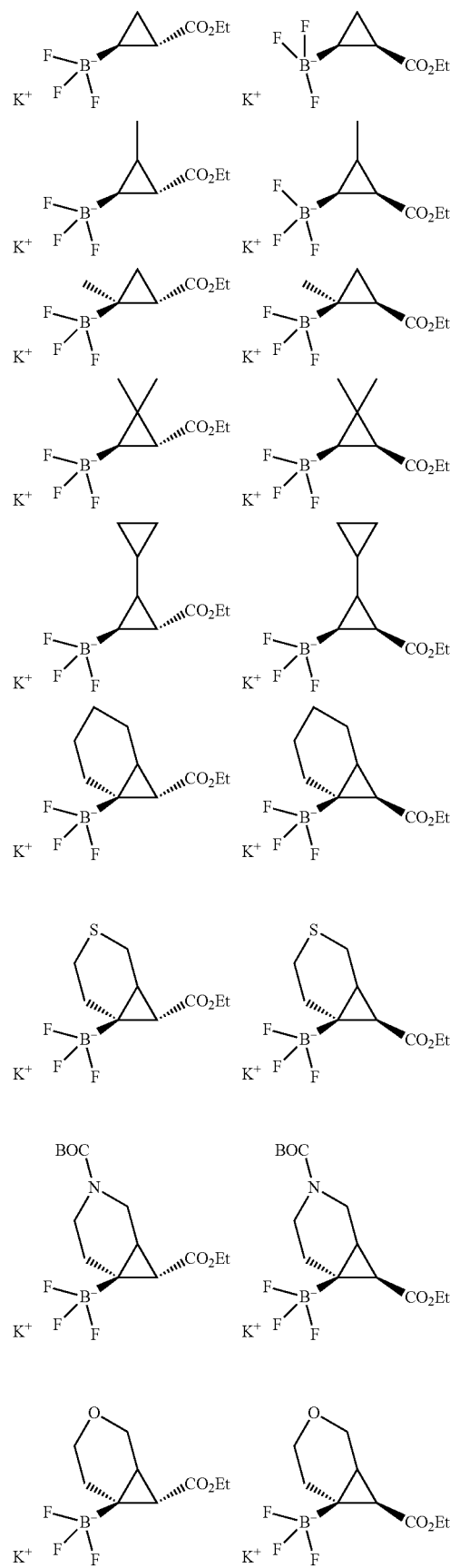

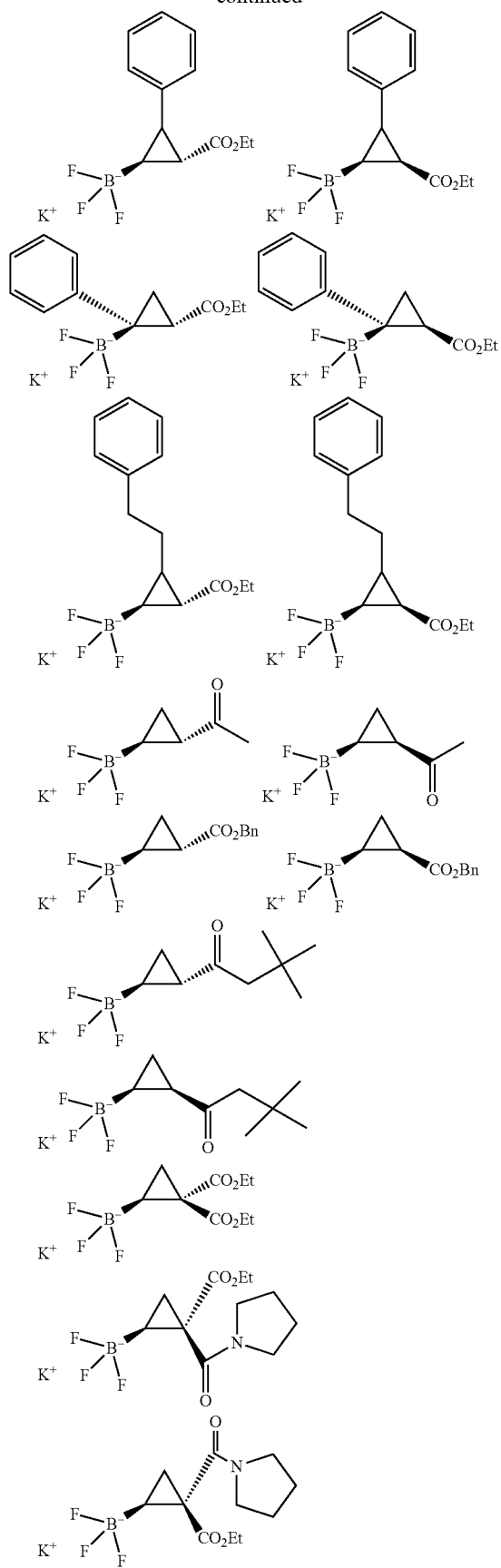
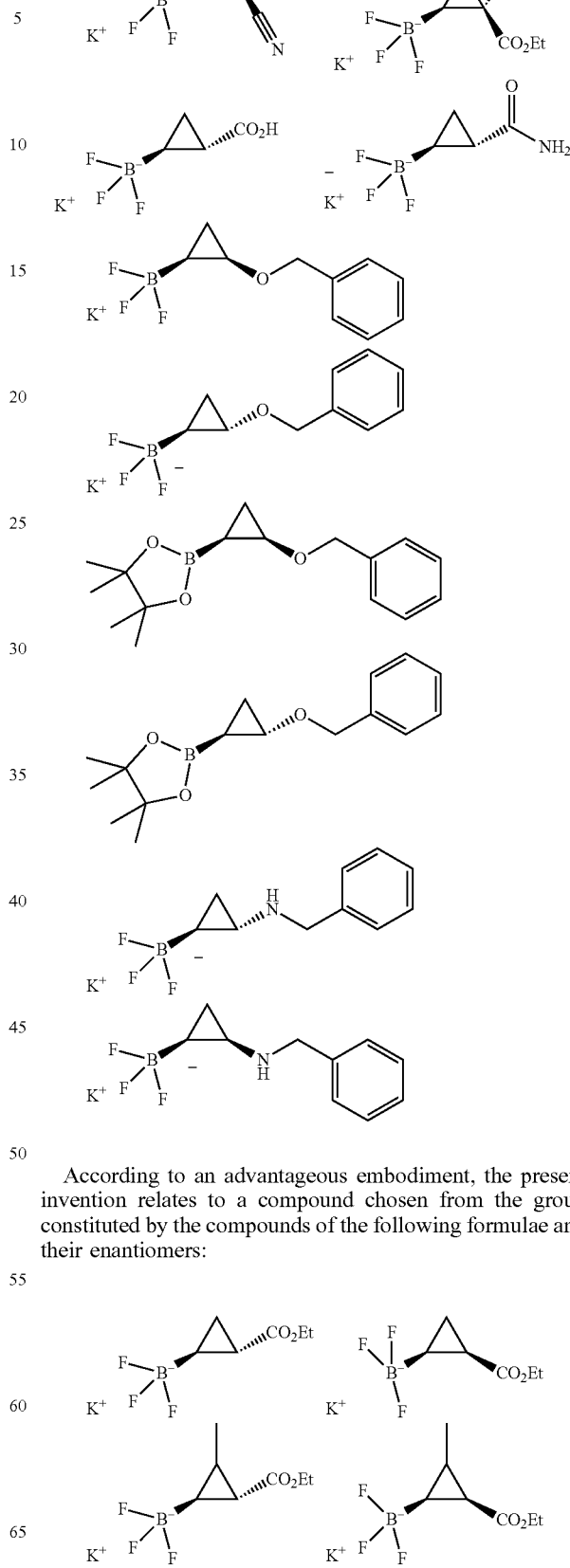
According to an advantageous embodiment, the present invention relates to a compound chosen from the group constituted by the compounds of the following formulae and their enantiomers:

-continued

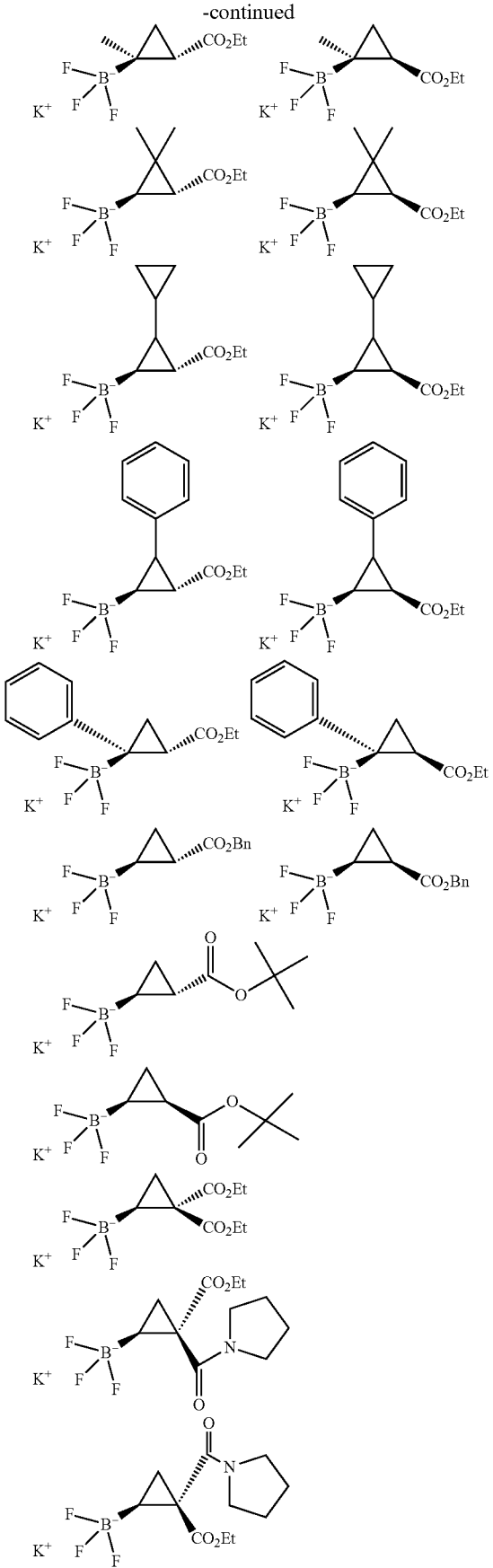

The invention also relates to the use of a compound of formula (I), for the preparation of compounds of the following formula (II):

(II)

in which:
$R_1$, $R_3$, $R_4$ and $R_5$, identical or different, are chosen from the group constituted by:
1. H, provided that $R_3$ does not represent H,
2. the aryls comprising rings with 6 to 15 carbon atoms, optionally substituted;
3. the heterocycles or heteroaryls comprising rings with 2 to 15 carbon atoms, optionally substituted;
4. the linear or branched alkenyls comprising 1 to 12 carbon atoms, optionally substituted, or carbon rings comprising 3 to 12 carbon atoms and one or more C=C double bonds, optionally substituted;
5. the linear or branched alkynyls comprising 1 to 15 carbon atoms, optionally substituted;
6. the linear, cyclic or branched alkyl groups comprising 1 to 15 carbon atoms, optionally substituted;
$R_1$ and $R_4$, or $R_1$ and $R_5$ being able to form a ring with 5, 6, or 7 members optionally comprising a heteroatom chosen from oxygen, nitrogen and sulphur, said ring being able to be substituted;
$R_2$ is chosen from the group constituted by the groups being able to be represented by $R_1$, $R_4$ or $R_5$, as well as —$COR^a$, —$COOR^a$, —$CONH_2$, —$CONHR^a$, —$CONR^aR^b$, —CN and —$NO_2$,
in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;
$R^a$ and $R^b$ being able to be linked in order to form a ring, optionally substituted,
W represents a functional group chosen from —CHO, —$COR^a$, —COOH, —$COOR^a$, —$CONH_2$, —$CONHR^a$, —$CONR^aR^b$, —$CH_2OH$, —$CH_2OR^a$, —$CHR^bOH$, —$CHR^bOR^a$, —$CR^bR^{b'}OH$, —$CR^bR^{b'}OR^a$, —$CH_2NH_2$, —$CH_2NHZ$, —$CHR^aNHZ$, —OH, —$OR^a$, —OZ', —$NH_2$, —$NHR^a$, —$NR^aR^b$, —NHZ and —$NZZ_2$,
in which Z represents a protective group of an amine function, Z' represents a protective group of an alcohol function, and
in which $R^a$, $R^b$ and $R^{b'}$, identical or different, represent linear, cyclic or branched, aromatic, or aromatic or non-aromatic heterocyclic alkyl, alkenyl, alkynyl groups comprising 1 to 15 carbon atoms, optionally substituted;
provided that:
when $R_1$, $R_2$, $R_4$ and $R_5$ represent H and B represents $B(OH)_2$, $B(OR)_2$, or $B(OR')_3M$, then W is chosen from —$COR^a$, —$CONH_2$, —$CONHR^a$, and —$CONR^aR^b$, when $R_1$, $R_2$, $R_4$ and $R_5$ represent H and B represents $BF_3M$, then W is chosen from —COOH, —COOR$^a$, —CHO, —COR$^a$—CONH$_2$, —CONHR$^a$, —CONR$^a$R$^b$, when W represents CH$_2$OH, —CH$_2$OR$^a$, —CHR$^b$OH, —CHR$^b$OR$^a$, —CR$^b$R$^b'$OH, or —CR$^b$R$^b'$OR$^a$, and B represents B(OH)$_2$, B(OR)$_2$, or B(OR')$_3$M, then:

$R_1$ does not represent H, or $R_2$ and $R_4$ do not represent H, or $R_2$ and $R_5$ do not represent H.

when W represents CH$_2$OH, —CH$_2$OR$^a$, —CHR$^b$OH, —CHR$^b$OR$^a$, —CR$^b$R$^b'$OH, or —CR$^b$R$^b'$OR$^a$, and B represents $BF_3M$, then $R_1$ or $R_2$ do not represent H.

when W represents —COOH or —COOR$^a$, and B represents B(OH)$_2$, B(OR)$_2$, or B(OR')$_3$M, then:

$R_1$ does not represent H, or $R_2$ and $R_4$ do not represent H, or $R_2$ and $R_5$ do not represent H, by reaction of said compound of formula (I) with a compound of the following formula (III):

$$R_3—X_2,$$

in which $R_3$ is as defined above, and $X_2$ is chosen from the group constituted by the halides, in particular iodine, bromine and chlorine, and triflate (OTf), in the presence of a catalyst containing a transition metal, and, optionally, a ligand.

According to an advantageous embodiment, the present invention relates to a use in which said transition metal is palladium (0) or palladium (II), said catalyst being in particular chosen from the group constituted by Pd(PPh$_3$)$_4$, Pd(OAc)$_2$, PdCl$_2$(dppf), PdCl$_2$ and PdCl$_2$(CN)$_2$.

According to an advantageous embodiment, the present invention relates to a use, said use being in the presence of a ligand chosen from the group constituted by PPh$_3$, P(tBu)$_3$, n-BuPAd$_2$, 1,2-bis(diphenylphosphine)propane (dpp), tricyclohexylphosphane (PCy$_3$), S-Phos and Xantphos.

According to an advantageous embodiment, the present invention relates to a use in which W represents a functional group chosen from —CHO, —COR$^a$, —COOH, —COOR$^a$, —CONH$_2$, —CONHR$^a$, —CONR$^a$R$^b$, —CH$_2$OH, —CH$_2$OR$^a$, —CHR$^b$OH, —CHR$^b$OR$^a$, —CR$^b$R$^b'$H, —CR$^b$R$^b'$OR$^a$, —CH$_2$NH$_2$, —CH$_2$NHZ, —CHR$^a$NHZ.

According to an advantageous embodiment, the present invention relates to a use in which W represents a functional group chosen from —CONH—SO$_2$-cyclopropyl, —CH$_2$—NH—CO—CH$_2$—CH$_3$, and the group of the following formula:

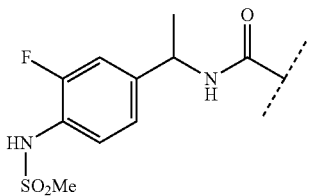

According to an advantageous embodiment, the present invention relates to a use in which $R_2$ represents H.

According to an advantageous embodiment, the present invention relates to a use in which $R_2$ is chosen from the group constituted by the groups —COR$^a$, —COOR$^a$, —CONH$_2$, —CONHR$^a$, —CONR$^a$R$^b$, —CN and —NO$_2$, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;

R$^a$ and R$^b$ being able to be linked in order to form a ring, optionally substituted.

According to an advantageous embodiment, the present invention relates to a use in which $R_1$, $R_4$ and $R_5$ represent H, an aryl, a heterocycle, a heteroaryl or an alkyl as defined previously.

According to an advantageous embodiment, the present invention relates to a use in which $R_1$, $R_2$, $R_4$ and $R_5$ represent H.

According to an advantageous embodiment, the present invention relates to a use in which W represents a functional group chosen from —OH, —OR$^a$, —OZ', —NH$_2$, —NHR$^a$, —NR$^a$R$^b$, —NHZ and —NZZ$_2$, $R_1$, $R_2$, $R_4$ and $R_5$ representing in particular H.

According to an advantageous embodiment, the present invention relates to a use in which $R_1$ and $R_2$ represent, independently of one another, H or a linear, cyclic or branched alkyl group comprising 1 to 15 carbon atoms, optionally substituted.

According to an advantageous embodiment, the present invention relates to a use in which $R_2$ represents H or a linear, cyclic or branched alkyl group comprising 1 to 15 carbon atoms, optionally substituted.

According to an advantageous embodiment, the present invention relates to the use of a compound of formula (I-A) as described previously, for the preparation of compounds of the following formula (II-A):

in which:

$R_1$, $R_3$ and $R_4$, identical or different, are chosen from the group constituted by:

1. H, provided that $R_3$ does not represent H,
2. the aryls comprising rings with 6 to 15 carbon atoms, optionally substituted;
3. the heterocycles or heteroaryls comprising rings with 2 to 15 carbon atoms, optionally substituted;
4. the linear or branched alkenyls comprising 1 to 12 carbon atoms, optionally substituted, or carbon rings comprising 3 to 12 carbon atoms and one or more C=C double bonds, optionally substituted;
5. the linear or branched alkynyls comprising 1 to 15 carbon atoms, optionally substituted;
6. the linear, cyclic or branched alkyl groups comprising 1 to 15 carbon atoms, optionally substituted;

at least one of the $R_1$ and $R_4$ groups representing H, $R_2$ is chosen from the group constituted by the groups being able to be represented by $R_1$, $R_4$ or $R_5$, as well as —COR$^a$, —COOR$^a$, —CONH$_2$, —CONHR$^a$, —CONR$^a$R$^b$, —CN and —NO$_2$, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted;

R$^a$ and R$^b$ being able to be linked in order to form a ring, optionally substituted, W represents a functional group chosen from —CHO, —COR$^a$, —COOH, —COOR$^a$, —CONH$_2$, —CONHR$^a$, —$CONR^aR^b$, —$CONH-SO_2-R^a$, —$CH_2OH$, —$CH_2OR^a$, —$CHR^bOH$, —$CHR^bOR^a$, —$CR^bR^{b'}OH$, —$CR^bR^{b'}OR^a$, —$CH_2NH_2$, —$CH_2NHZ$, —$CHR^aNHZ$, —$CH_2-NH-COR^a$, in which Z represents a protective group of an amine function, and in which $R^a$, $R^b$ and $R^{b'}$, identical or different, represent linear, cyclic or branched, aromatic, or aromatic or non-aromatic heterocyclic alkyl, alkenyl, alkynyl groups comprising 1 to 15 carbon atoms, optionally substituted;

provided that:
when $R_1$, $R_2$ and $R_4$ represent H and B represents $B(OH)_2$, $B(OR)_2$, or $B(OR')_3M$, then W is chosen from —$COR^a$, —$CONH_2$, —$CONHR^a$, —$CONR^aR^b$, when $R_1$, $R_2$ and $R_4$ represent H and B represents $BF_3M$, then W is chosen from —COOH, —$COOR^a$, —CHO, —$COR^a$—$CONH_2$, —$CONHR^a$, —$CONR^aR^b$, when W represents $CH_2OH$, —$CH_2OR^a$, —$CHR^bOH$, —$CHR^bOR^a$, —$CR^bR^{b'}OH$, or —$CR^bR^{b'}OR^a$, and B represents $B(OH)_2$, $B(OR)_2$, or $B(OR')_3M$, then:
$R_1$ does not represent H, or
$R_2$ and $R_4$ do not represent H, when W represents $CH_2OH$, —$CH_2OR^a$, —$CHR^bOH$, —$CHR^bOR^a$, —$CR^bR^{b'}OH$, or —$CR^bR^{b'}OR^a$, and B represents $BF_3M$, then $R_1$ or $R_2$ does not represent H.

when W represents —COOH or —$COOR^a$, and B represents $B(OH)_2$, $B(OR)_2$, or $B(OR')_3M$, then:
$R_1$ does not represent H, or
$R_2$ and $R_4$ do not represent H, by reaction of said compound of formula (I) with a compound of the following formula (III):

$$R_3-X_2,$$

in which $R_3$ is as defined above, and $X_2$ is chosen from the group constituted by the halides, in particular iodine, bromine and chlorine, and triflate (OTf), in the presence of a catalyst containing a transition metal, and, optionally, of a ligand.

According to an advantageous embodiment, the present invention relates to the use of a compound of formula (I-B) as described previously, for the preparation of compounds of the following formula (II-A):

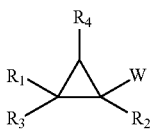

(II-A)

in which:
$R_1$, $R_3$ and $R_4$, identical or different, are chosen from the group constituted by:
1. H, provided that $R_3$ does not represent H,
2. the aryls comprising rings with 6 to 15 carbon atoms, optionally substituted;
3. the heterocycles or heteroaryls comprising rings with 2 to 15 carbon atoms, optionally substituted;
4. the linear or branched alkenyls comprising 1 to 12 carbon atoms, optionally substituted, or carbon rings comprising 3 to 12 carbon atoms and one or more C=C double bonds, optionally substituted;
5. the linear or branched alkynyls comprising 1 to 15 carbon atoms, optionally substituted;
6. the linear, cyclic or branched alkyl groups comprising 1 to 15 carbon atoms, optionally substituted;
at least one of the $R_1$ and $R_4$ groups representing H, $R_2$ is chosen from the group constituted by the groups being able to be represented by $R_1$, $R_4$ or $R_5$, as well as —$COR^a$, —$COOR^a$, —$CONH_2$, —$CONHR^a$, —$CONR^aR^b$, —CN and —$NO_2$, in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;

$R^a$ and $R^b$ being able to be linked in order to form a ring, optionally substituted, W represents a functional group chosen from —CHO, —$COR^a$, —COOH, —$COOR^a$, —$CONH_2$, —$CONHR^a$, —$CONR^aR^b$, —$CONH-SO_2-R^a$, —$CH_2OH$, —$CH_2OR^a$, —$CHR^bOH$, —$CHR^bOR^a$, —$CR^bR^{b'}OH$, —$CR^bR^{b'}OR^a$, —$CH_2NH_2$, —$CH_2NHZ$, —$CHR^aNHZ$, —$CH_2-NH-COR^a$, in which Z represents a protective group of an amine function, and in which $R^a$, $R^b$ and $R^{b'}$, identical or different, represent linear, cyclic or branched, aromatic, or aromatic or non-aromatic heterocyclic alkyl, alkenyl, alkynyl groups comprising 1 to 15 carbon atoms, optionally substituted;

provided that:
when $R_1$, $R_2$ and $R_4$ represent H and B represents $BF_3M$, then W is chosen from —COOH, —$COOR^a$, —CHO, —$COR^a$—$CONH_2$, —$CONHR^a$, —$CONR^aR^b$, when W represents $CH_2OH$, —$CH_2OR^a$, —$CHR^bOH$, —$CHR^bOR^a$, —$CR^bR^{b'}OH$, or —$CR^bR^{b'}OR^a$, and B represents $BF_3M$, then $R_1$ or $R_2$ do not represent H, by reaction of said compound of formula (I) with a compound of the following formula (III):

$$R_3-X_2,$$

in which $R_3$ is as defined above, and $X_2$ is chosen from the group constituted by the halides, in particular iodine, bromine and chlorine, and triflate (OTf), in the presence of a catalyst containing a transition metal, and, optionally, of a ligand.

According to an advantageous embodiment, the present invention relates to the use of a compound of formula (I-A) or (I-B) in which said transition metal is palladium (0) or palladium (II), said catalyst being in particular chosen from the group constituted by $Pd(PPh_3)_4$, $Pd(OAc)_2$, $PdCl_2(dppf)$, $PdCl_2$ and $PdCl_2(CN)_2$.

According to an advantageous embodiment, the present invention relates to the use of a compound of formula (I-A) or (I-B), said use being in the presence of a ligand chosen from the group constituted by $PPh_3$, $P(tBu)_3$, n-$BuPAd_2$, 1,2-bis(diphenylphosphine)propane (dpp), tricyclohexylphosphane ($PCy_3$), S-Phos and Xantphos.

According to an advantageous embodiment, the present invention relates to the use of a compound of formula (I-A) or (I-B) in which W represents a functional group chosen from —CHO, —$COR^a$, —COOH, —$COOR^a$, —$CH_2OH$, —$CH_2OR^a$, —$CHR^bOH$, —$CHR^bOR^a$, —$CR^bR^{b'}OH$ and —$CR^bR^{b'}OR^a$.

According to an advantageous embodiment, the present invention relates to the use of a compound of formula (I-A) or (I-B) in which W represents a functional group chosen from —CHO, —$COR^a$, —COOH and —$COOR^a$, W representing in particular —$COOR^a$.

According to an advantageous embodiment, the present invention relates to the use of a compound of formula (I-A) or (I-B) in which W represents a functional group chosen from —$CONH-SO_2$-cyclopropyl, —$CH_2-NH-CO-CH_2-CH_3$, and the group of the following formula:

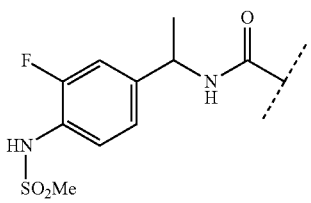

According to an advantageous embodiment, the present invention relates to the use of a compound of formula (I-A) or (I-B) in which $R_2$ represents H.

According to an advantageous embodiment, the present invention relates to the use of a compound of formula (I-A) or (I-B) in which $R_2$ is chosen from the group constituted by the —$COR^a$, —$COOR^a$, —$CONH_2$, —$CONHR^a$, —$CONR^aR^b$ and —$NO_2$ groups,
in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;
$R^a$ and $R^b$ being able to be linked in order to form a ring, optionally substituted.

According to an advantageous embodiment, the present invention relates to the use of a compound of formula (I-A) or (I-B) in which $R_1$, $R_2$ and $R_4$ represent H.

According to an advantageous embodiment, the present invention relates to the use of a compound of formula (I-A) or (I-B) in which $R_1$ represents H.

According to an advantageous embodiment, the present invention relates to the use of a compound of formula (I-A) or (I-B) in which $R_1$ represents H and $R_4$ represents an aryl, a heterocycle, a heteroaryl or an alkyl as defined previously.

According to an advantageous embodiment, the present invention relates to the use of a compound of formula (I-A) or (I-B) in which $R_4$ represents H.

According to an advantageous embodiment, the present invention relates to the use of a compound of formula (I-A) or (I-B) in which $R_4$ represents H and R1 represents an aryl, a heterocycle, a heteroaryl or an alkyl as defined previously.

According to an advantageous embodiment, the present invention relates to the use of a compound of formula (I-A) or (I-B) in which $R_1$ and $R_2$ represent H and $R_4$ represents an aryl, a heterocycle, a heteroaryl or an alkyl as defined previously.

According to an advantageous embodiment, the present invention relates to the use of a compound of formula (I-A) or (I-B) in which $R_2$ and $R_4$ represent H and $R_1$ represents an aryl, a heterocycle, a heteroaryl or an alkyl as defined previously.

According to an advantageous embodiment, the present invention relates to the use of a compound of formula (I-A) or (I-B) in which $R_1$ represents H, $R_4$ represents an aryl, a heterocycle, a heteroaryl or an alkyl as defined previously, and $R_2$ is chosen from the group constituted by the —$COR^a$, —$COOR^a$, —$CONH_2$, —$CONHR^a$, —$CONR^aR^b$ and —$NO_2$ groups,
in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;
$R^a$ and $R^b$ being able to be linked in order to form a ring, optionally substituted.

According to an advantageous embodiment, the present invention relates to the use of a compound of formula (I-A) or (I-B) in which $R_4$ represents H, $R_1$ represents an aryl, a heterocycle, a heteroaryl or an alkyl as defined previously, and $R_2$ is chosen from the group constituted by the —$COR^a$, —$COOR^a$, —$CONH_2$, —$CONHR^a$, —$CONR^aR^b$ and —$NO_2$ groups,
in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;
$R^a$ and $R^b$ being able to be linked in order to form a ring, optionally substituted.

According to an advantageous embodiment, the present invention relates to the use of a compound of formula (I-A) or (I-B) in which $R_1$ and $R_4$ represent H, and $R_2$ is chosen from the group constituted by the —$COR^a$, —$COOR^a$, —$CONH_2$, —$CONHR^a$, —$CONR^aR^b$ and —$NO_2$ groups,
in which $R^a$ and $R^b$, identical or different, represent linear, cyclic or branched, aromatic, or aromatic or non-aromatic heterocyclic alkyl, alkenyl, alkynyl groups comprising 1 to 15 carbon atoms, optionally substituted;
$R^a$ and $R^b$ being able to be linked in order to form a ring, optionally substituted.

According to an advantageous embodiment, the present invention relates to the use of a compound of formula (I-A) or (I-B), respectively of particular formula (I-C) or (I-D) as defined previously.

According to an advantageous embodiment, the present invention relates to a use in which $R_3$ represents a group chosen from:

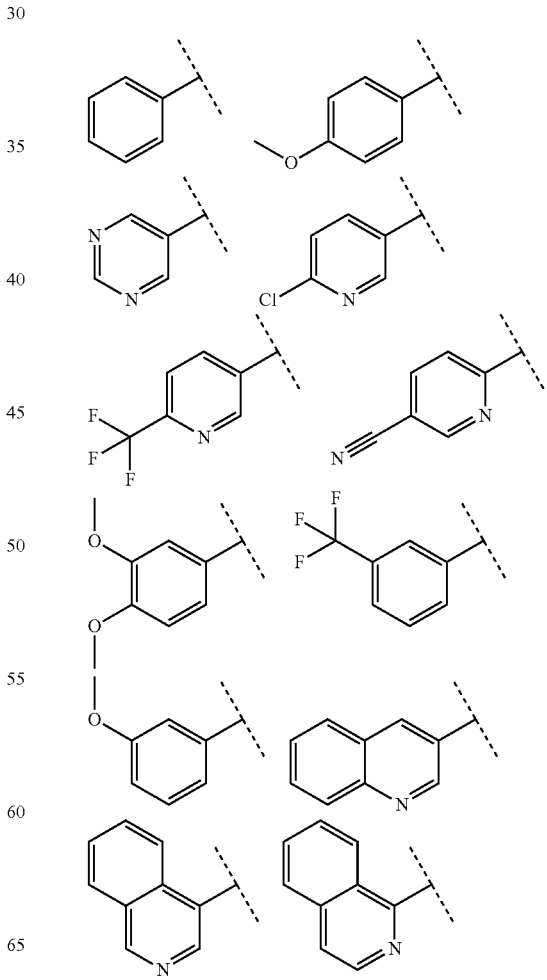

-continued
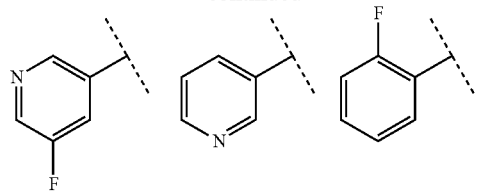
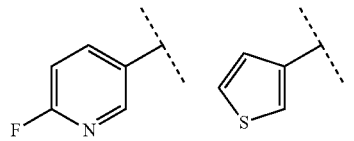
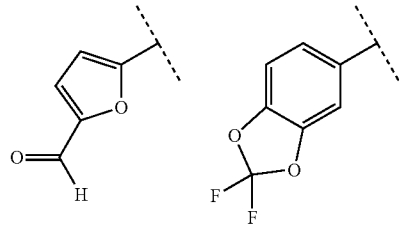
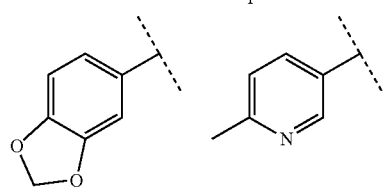
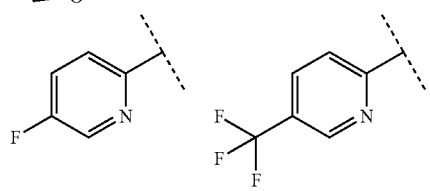
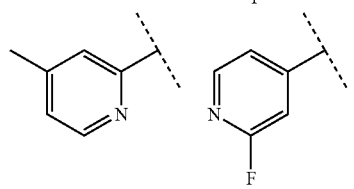
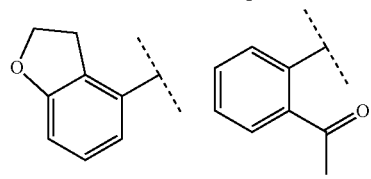
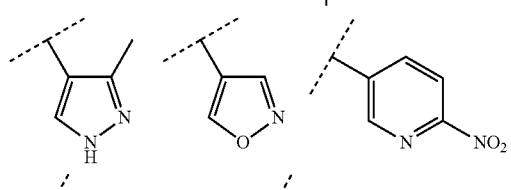
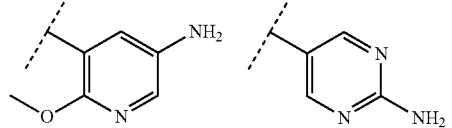
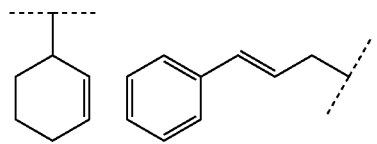
-continued
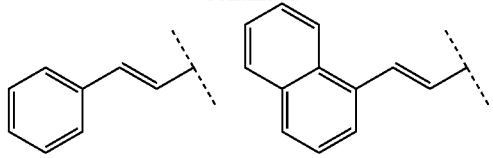
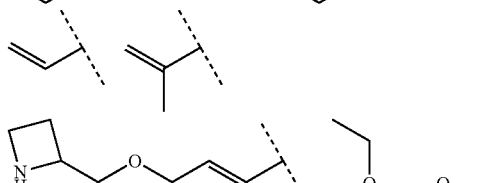
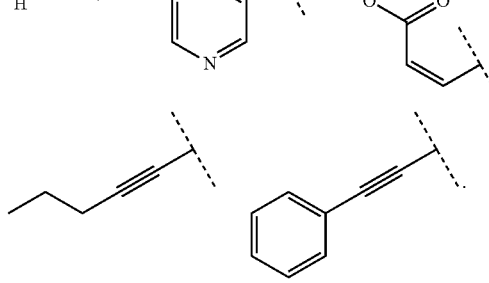
According to an advantageous embodiment, the present invention relates to a use in which $R_3$ represents a group chosen from:
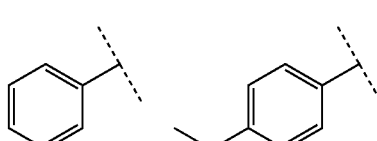
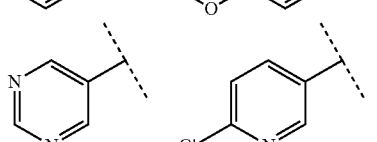
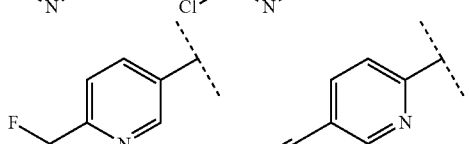
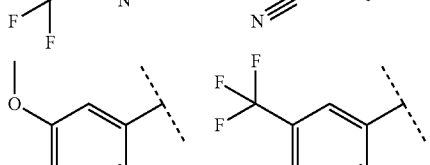
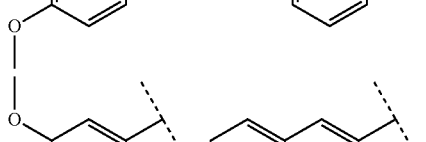
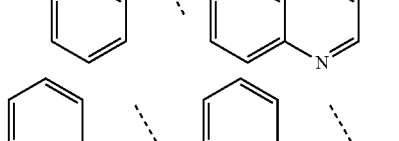
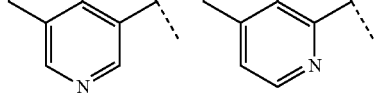

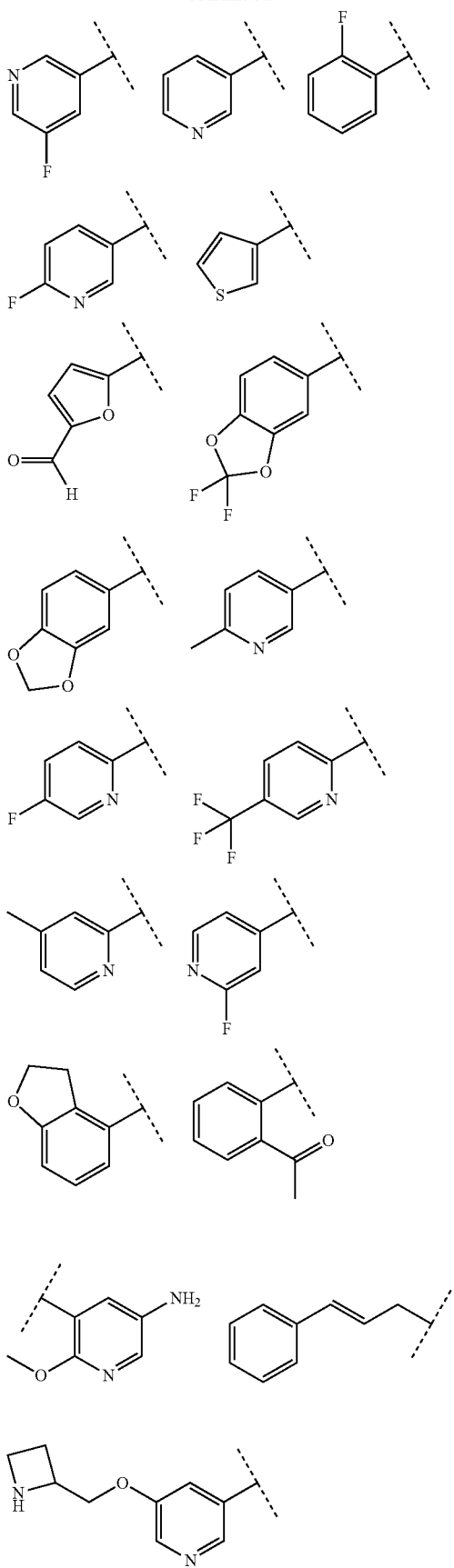
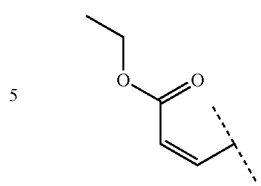
According to an advantageous embodiment, the present invention relates to the use of a compound chosen from the group constituted by the compounds of the following formulae and their enantiomers:
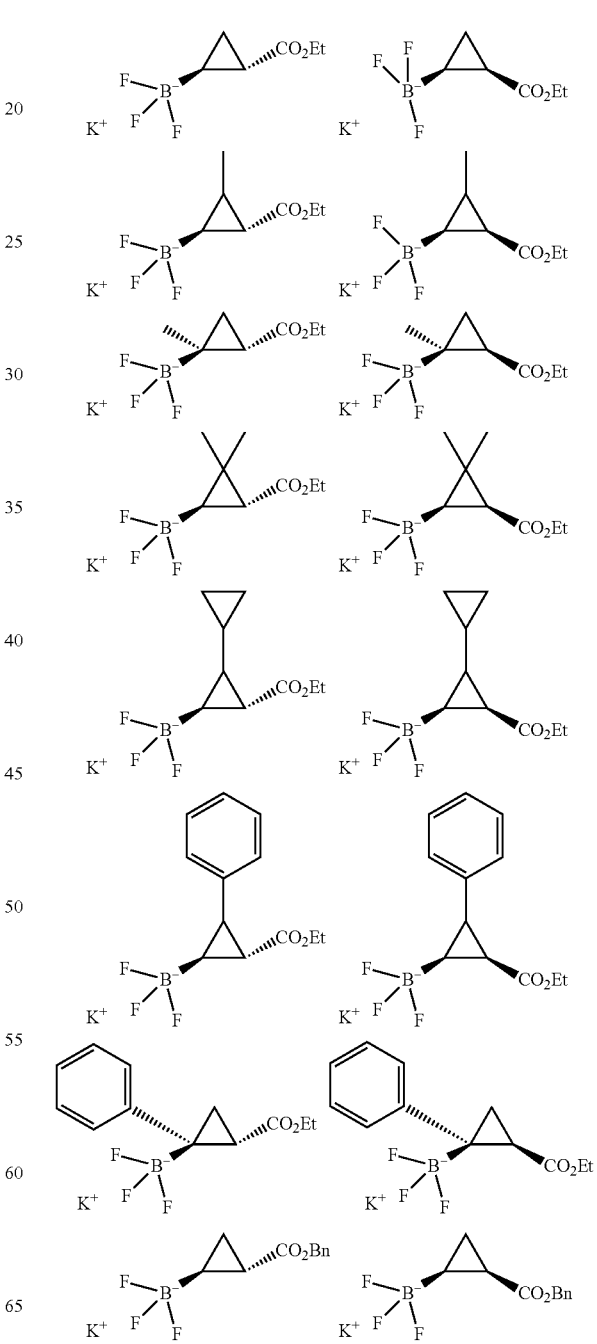

-continued

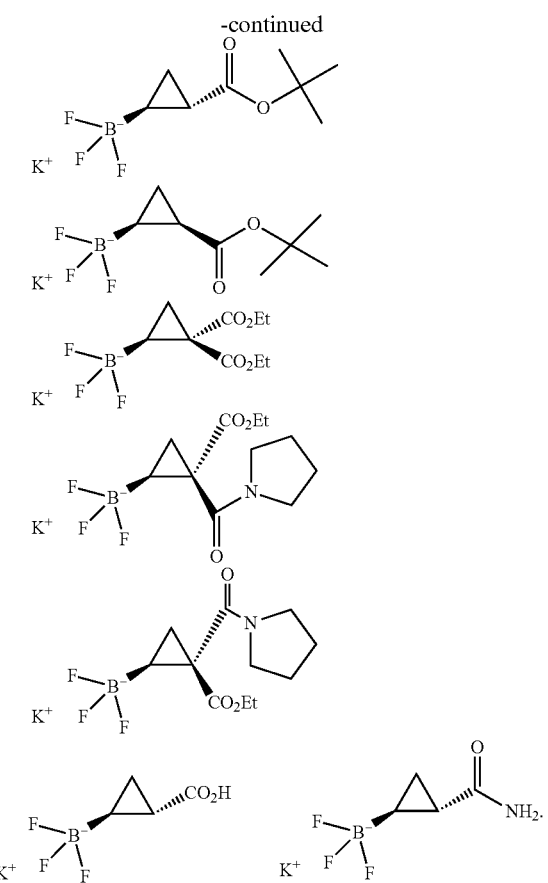

The following examples illustrate the invention.

EXAMPLES

Example 1

Synthesis of potassium
[2-ethoxycarbonylcyclopropyl]-trifluoroborate

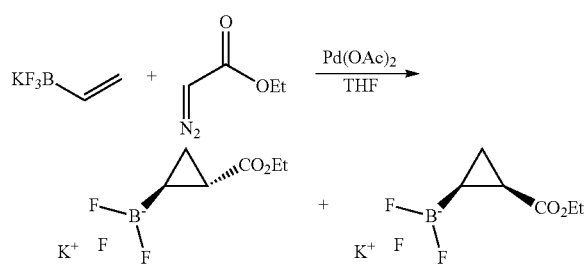

Potassium vinyl trifluoroborate (888 g, 6.63 mole) is solubilized in THF (9 L). Palladium acetate (14.88 g, 66 mmol) is added. The mixture is heated to 35° C. and a solution of diazo ethyl acetate (902 ml, 7.72 mole) in THF (1 L) is added dropwise over 3 hours 40 (exothermicity). The mixture is stirred for an additional 30 minutes. Heptane is added to the solution. The suspension thus obtained is stirred for 30 minutes, then filtered. The solid is crystallized from 9 L of acetone at −18° C. The solid is filtered and dried in order to produce the expected cis product (335 g, 1.52 mole, 23%). The filtrate is washed with bone black, filtered and concentrated to dryness. The product is crystallized from 10 L of ethanol in order to produce the expected trans product (903 g, 4.1 mmol, 62%).

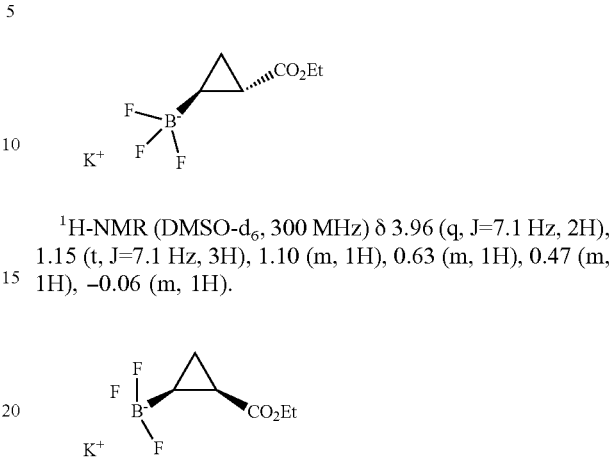

$^1$H-NMR (DMSO-$d_6$, 300 MHz) δ 3.96 (q, J=7.1 Hz, 2H), 1.15 (t, J=7.1 Hz, 3H), 1.10 (m, 1H), 0.63 (m, 1H), 0.47 (m, 1H), −0.06 (m, 1H).

$^1$H-NMR (DMSO-$d_6$, 300 MHz) δ 3.90 (q, J=7.0 Hz, 2H), 1.25 (m, 1H), 1.12 (t, J=7.0 Hz, 3H), 0.75 (m, 1H), 0.54 (m, 1H), −0.15 (m, 1H).

Example 2

Synthesis of substituted potassium
[2-ethoxycarbonylcyclopropyl]-trifluoroborates

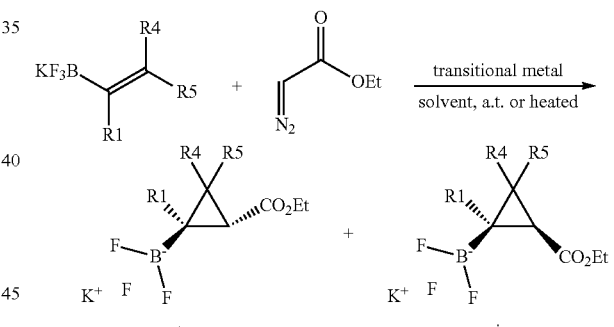

General Procedure:
Method A:
Palladium acetate (0.01-0.2 eq.) is added under nitrogen to a solution of potassium alkenyltrifluoroborate (1 eq.) in tetrahydrofuran. The mixture is heated to 35-70° C. and a solution of diazo ethyl acetate (1.2 to 5 eq.) in tetrahydrofuran is added very slowly dropwise. The reaction medium is stirred at this temperature for 1 to 10 h until conversion is complete. Heptane is added to the solution. The suspension thus obtained is stirred for 30 minutes, then filtered. When the cis derivative sufficiently abundant in the crude reaction medium, it can be crystallized from acetone at low temperature (−20° C.). As regards the trans compound it is crystallized from an acetonitrile/diethyl ether mixture.
Method B:
Copper acetoacetate (0.2 eq.) is added under nitrogen to a solution of potassium alkenyltrifluoroborate (1 eq.) in a toluene/dioxane mixture 1/1. The mixture is heated to 35-70° C. and a solution of diazo ethyl acetate (1.2 to 5 eq.)

in toluene is added very slowly dropwise. The reaction medium is stirred at this temperature for 1 to 10 h until conversion is complete. After returning to ambient temperature, heptane is added to the solution. The suspension thus obtained is stirred for 30 minutes, then filtered. When the cis derivative is sufficiently abundant in the crude reaction medium, it can be crystallized from acetone at low temperature (−20° C.). As regards the trans compound, it is crystallized from an acetonitrile/diethyl ether mixture or methanol.

Synthesis of potassium [2-ethoxycarbonyl-3-methyl-cyclopropyl]-trifluoroborate

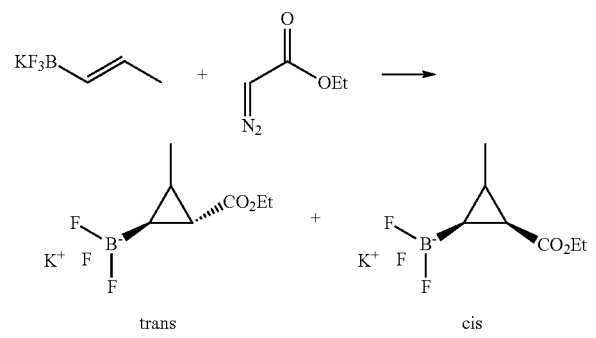

The product is obtained according to the general procedure.

$^1$H-NMR (DMSO-d$_6$, 300 MHz) (trans compound): δ 3.87 (q, J=7.1 Hz, 2H), 1.3-1.0 (m, 2H), 1.09 (t, J=7.1 Hz, 3H), 0.95 (d, J=7.9 Hz, 3H), −0.30 (m, 1H).

$^1$H-NMR (DMSO-d$_6$, 300 MHz) (cis compound): δ 3.96 (q, J=7.05 Hz, 2H), 1.3-1.0 (m, 2H), 1.15 (t, J=7.05 Hz, 3H), 0.90 (d, J=5.3 Hz, 3H), −0.16 (m, 1H).

Synthesis of potassium [2-ethoxycarbonyl-1-methyl-cyclopropyl]-trifluoroborate

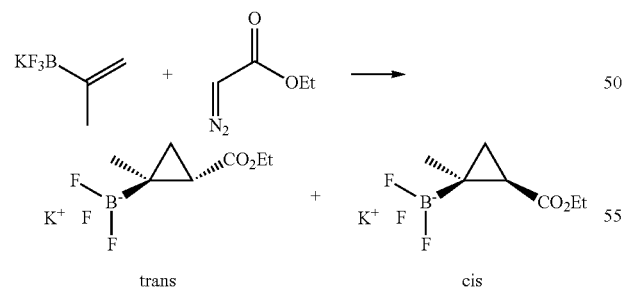

The product is obtained according to the general procedure.

$^1$H-NMR (DMSO-d$_6$, 300 MHz) (trans compound): δ 3.9 (m, 2H), 1.28 (dd, J=4.7 Hz, J=7.1 Hz, 1H), 1.14 (t, J=7.1 Hz, 3H), 0.87 (s, 3H), 0.63 (dd, J=1.9 Hz, J=7.1 Hz, 1H), 0.45 (m, 1H).

No visible cis compound.

Synthesis of potassium [2-ethoxycarbonyl-3-cyclopropyl-cyclopropyl]-trifluoroborate

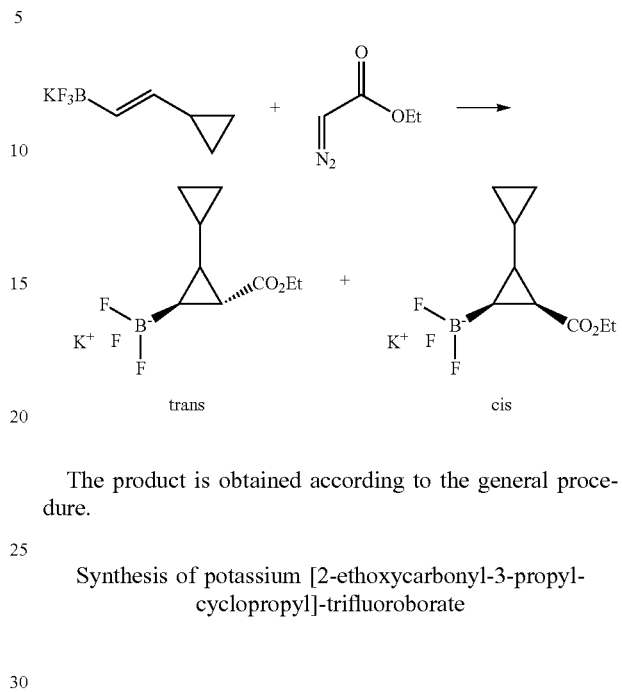

The product is obtained according to the general procedure.

Synthesis of potassium [2-ethoxycarbonyl-3-propyl-cyclopropyl]-trifluoroborate

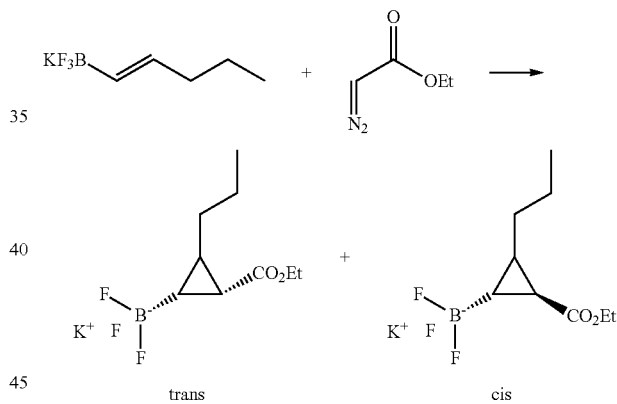

$^1$H-NMR (DMSO-d$_6$, 300 MHz) (trans compound): δ 3.95 (q, J=6.6 Hz, 2H), 1.5-1.0 (m, 9H), 0.83 (t, J=6.6 Hz, 3H), −0.11 (m, 1H).

$^1$H-NMR (DMSO-d$_6$, 300 MHz) (cis compound): δ 3.88 (q, J=7.1 Hz, 2H), 1.5-1.0 (m, 9H), 0.86 (d, J=7.1 Hz, 3H), −0.26 (m, 1H).

Synthesis of potassium [2-ethoxycarbonyl-3-phenyl-cyclopropyl]-trifluoroborate

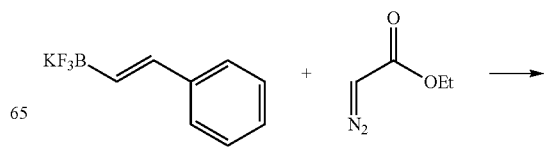

-continued

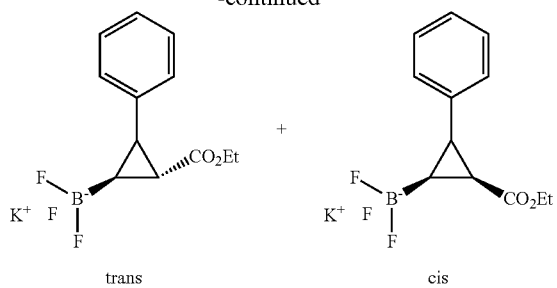

trans    cis

The product is obtained according to the general procedure.

$^1$H-NMR (DMSO-$d_6$, 300 MHz) (trans compound): δ 7.20-7.0 (m, 5H), 3.73 (m, 2H), 2.18 (t, J=8.6 Hz, 1H), 1.56 (dd, J=8.4 Hz, J=6.6 Hz, 1H), 0.92 (t, J=8.8 Hz, 3H), 0.71 (m, 1H).

$^1$H-NMR (DMSO-$d_6$, 300 MHz) (cis compound): δ 7.20-7.0 (m, 5H), 3.94 (q, J=6.4 Hz, 2H), 2.29 (m, 1H), 1.59 (m, 1H), 1.09 (t, J=6.4 Hz, 3H), 0.37 (m, 1H).

Synthesis of potassium [2-ethoxycarbonyl-1-phenyl-cyclopropyl]-trifluoroborate

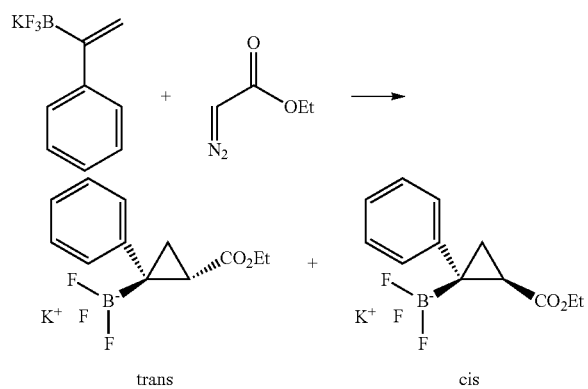

trans    cis

The product is obtained according to the general procedure.

MS (ES-, MeOH): 257.2 [M]-

Example 3

Synthesis of Potassium Cyclopropyltrifluoroborates Substituted in Position 2

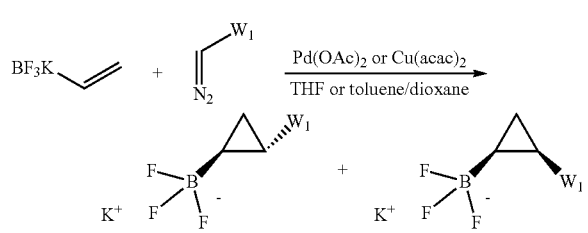

General Method:

Catalyst Pd(OAc)$_2$ or Cu(acac)$_2$ (0.02-0.2 eq.) is added to a solution of potassium vinyltrifluoroborate (1 eq) in THF or a toluene/dioxane mixture. The reaction medium is heated to 40-70° C. then the diazo derivative (2-5 eq.) is added slowly dropwise. The medium is stirred at this temperature for 1-10 h until conversion is complete. After returning to ambient temperature, heptane is added to the solution. The suspension thus obtained is stirred for 30 minutes, then filtered. When the cis derivative is sufficiently abundant in the crude reaction medium, it can be crystallized from acetone at low temperature (-20° C.). As regards the trans compound, it is crystallized from an acetonitrile/diethyl ether mixture or methanol.

Synthesis of potassium [2-benzyloxycarbonylcyclopropyl]-trifluoroborate

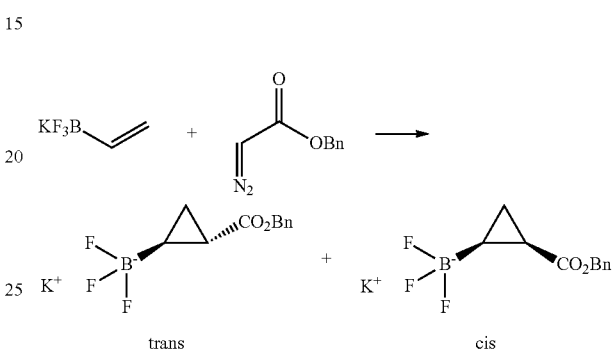

trans    cis

The product is obtained according to the general procedure.

$^1$H-NMR (DMSO-$d_6$, 300 MHz) (trans compound) δ 7.41-7.25 (m, 5H), 5.0 (d, J=1.8 Hz, 2H), 1.16 (m, 1H), 0.69 (dm, J=9.7 Hz, 1H), 0.53 (td, J=7.3 Hz, J=1.8 Hz, 1H), 0.00 (m, 1H).

$^1$H-NMR (DMSO-$d_6$, 300 MHz) (cis compound) δ 7.41-7.25 (m, 5H), 4.94 (d, J=12.1 Hz, 2H), 1.34 (m, 1H), 0.82 (m, 1H), 0.22 (tm, J=7.9 Hz, 1H), -0.08 (m, 1H).

Synthesis of potassium [2-tert-butoxycarbonylcyclopropyl]-trifluoroborate

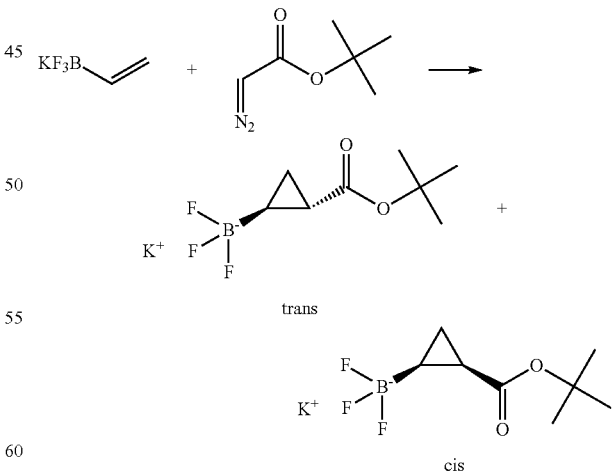

trans cis

The product is obtained according to the general procedure.

$^1$H-NMR (DMSO-$d_6$, 300 MHz) (trans compound) δ 1.36 (s, 9H), 1.01 (m, 1H), 0.54 (dm, J=9.9 Hz, 1H), 0.40 (tm, J=6.6 Hz, 1H), -0.11 (m, 1H).

¹H-NMR (DMSO-d₆, 300 MHz) (cis compound) δ 1.33 (s, 9H), 1.15 (m, 1H), 0.68 (m, 1H), 0.47 (m, 1H), −0.21 (m, 1H).

Synthesis of potassium [2,2-bis(ethoxycarbonyl)cyclopropyl]-trifluoroborate

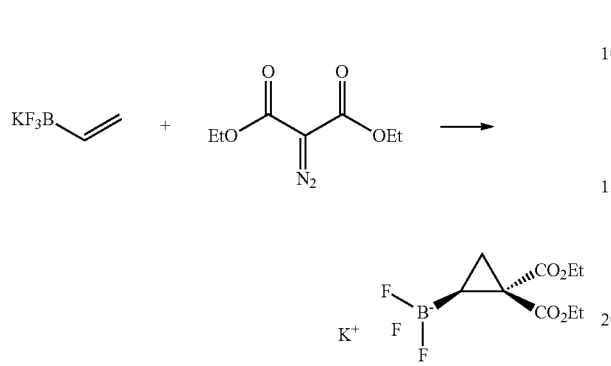

The product is obtained according to the general procedure.

¹H-NMR (DMSO-d₆, 300 MHz) δ 4.2 (q, 2H, J=7.1 Hz), 3.99 (q, 2H, J=8 Hz), 1.22 (t, 3H, J=8 Hz), 1.13 (t, 3H, J=7.1 Hz), 1.02 (dd, 1H, J=9.5 Hz, J=1.7 Hz), 0.83 (dm, H, J=10.3 Hz), 0.54 (m, 1H).

Synthesis of potassium [2-ethoxycarbonyl-2-(pyrrolidine-1-carbonyl)cyclopropyl]-trifluoroborate

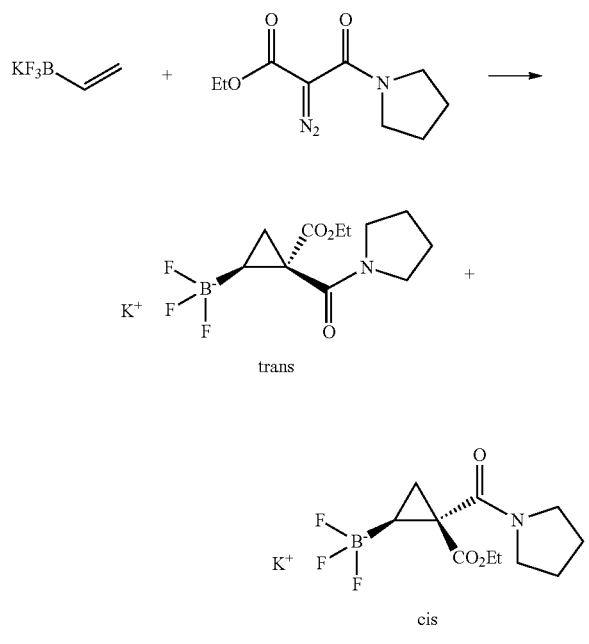

The product is obtained according to the general procedure.

¹H-NMR (DMSO-d₆, 300 MHz) cis/trans mixture δ 3.97 (m, 4H), 3.27-3.49 (m, 8H), 0.98-1.24 (m, 12H), 1.09 (t, 3H, J=8.5 Hz), 0.77 (m, 2H), 0.58 (m, 1H), 0.39 (m, 1H).

Example 4

Synthesis of (trans)-2-(4,4,5,5-tetramethyl-1,3,2-dioxaborolan-2-yl)cyclopropanecarboxylic acid

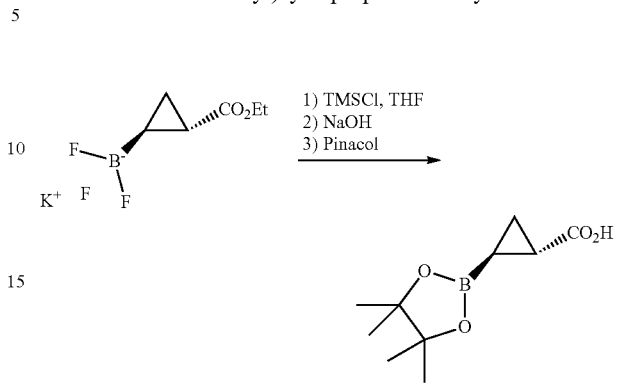

The potassium trifluoroborate derivative (Example 1, 15 g, 68.2 mmol) is solubilized in THF (150 ml). Trimethylsilane chloride (18.2 g, 143.2 mmol) is added dropwise. The medium is stirred at ambient temperature for 30 minutes. The reaction medium is poured into 600 ml of water. The THF is concentrated with a rotary evaporator and a molar solution of sodium hydroxide is added until a basic pH is reached (approximately 50 ml). The medium is stirred at ambient temperature overnight. NaOH in pellets (2 g) and a solution of sodium hydroxide (6N) are added and the medium is stirred overnight. The medium is concentrated to dryness, taken up in 700 ml of toluene and pinacol (8.46 g, 71.6 mmol) is added. The medium is filtered on Celite and concentrated to dryness. The amorphous oil is triturated in pentane (50 ml) in order to obtain a white solid (2.85 g, 13.4 mmol). The filtrate is placed in the freezer in order to produce a second batch of product (5.8 g, 27.4 mmol, overall yield 60%). ¹H-NMR (DMSO-d₆, 300 MHz) δ 12.25 (bs, 1H), 1.51 (m, 1H), 1.17 (s, 12H), 1.04 (m, 1H), 0.84 (m, 1H), 0.30 (m, 1H).

Example 5

Synthesis of potassium [(trans)-2-methylcyclopropyl]trifluoroborate

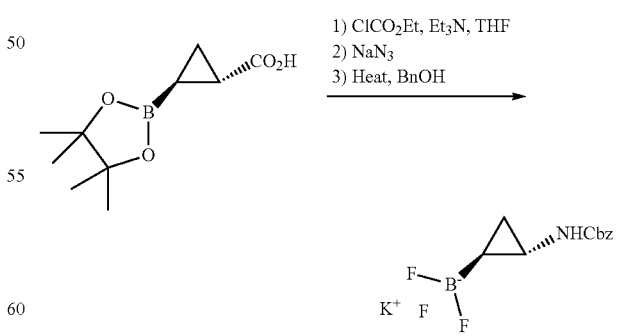

Carboxylic acid (Example 4, 8.65 g, 40.8 mmol) is solubilized in THF (216 ml). The medium is cooled down to 0° C. and triethylamine is added (8.5 ml, 61.2 mmol). Then ethylchloroformate (6.64 g, 61.2 mmol) is added dropwise. The medium is stirred at ambient temperature for 1 hour, cooled down to 0° C. and a solution of sodium azide (132.6 g, 2.04 mole) in water (325 ml) is added dropwise. The medium is stirred at ambient temperature overnight. Water (200 ml) is added and the expected product is extracted twice with isopropyl ether. The organic phase is dried over magnesium sulphate and filtered. Toluene (50 ml) and benzyl alcohol (4.3 ml) are added and the medium is heated to 105° C. The THF and isopropyl ether are distilled off from the medium. After being left overnight at 105° C., the medium is concentrated to dryness. The crude reaction medium is purified twice by chromatography on silica gel which does not allow removal of the excess benzyl alcohol. The product (6.48 g) is then put back in a water (16.2 ml)/methanol (78 ml) mixture and $KHF_2$ (11.17 g) is added and the medium is stirred at ambient temperature overnight. The suspension is concentrated to dryness and the solid is triturated in acetonitrile to 90° C. for 4 hours. The filtrate is concentrated in order to produce a white solid. $^1$H-NMR (DMSO-$d_6$, 300 MHz) δ 7.33 (m, 5H), 6.99 (bd, 0.8H), 6.7 (bs, 0.2H), 4.96 (s, 2H), 2.16 (m, 1H), 0.12 (m, 1H), 0.0 (m, 1H), −0.52 (m, 1H).

Example 6

Synthesis of potassium [(trans)-2-carboxycyclopropyl]-trifluoroborate

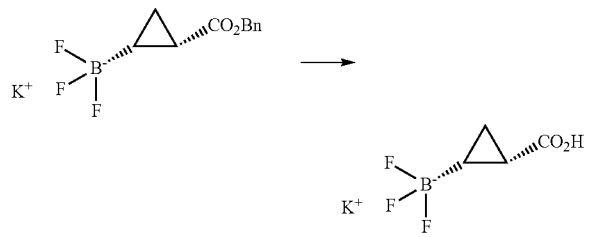

Palladium on carbon (0.2 mmol, 0.2 eq.) is added under an inert atmosphere to a solution of ester (Example 3, 1 mmol) in 5 ml of methanol. The reaction medium is placed under a hydrogen atmosphere (1 atm) for 5 hours, filtered on frit then concentrated to dryness in order to produce the expected carboxylic acid.
$^1$H-NMR (DMSO-$d_6$, 300 MHz) (trans compound) δ 1.12 (m, 1H), 0.68 (d, J=10.0 Hz, 1H), 0.52 (t, J=7.3 Hz, 1H), 0.00 (m, 1H).

Example 10

Synthesis of [(trans)-2-ethoxycarbonylcyclopropyl]boronic acid

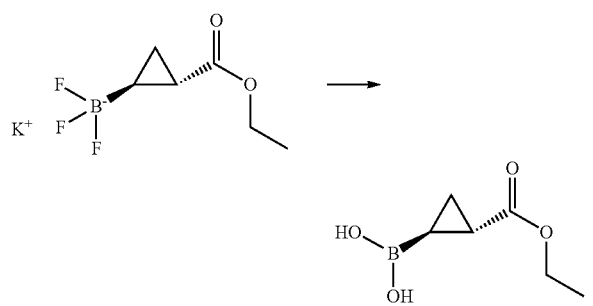

Silica gel (1 eq.) is added to a solution of potassium trifluoroborate derivative (Example 1, 1 eq.) in water. The reaction medium is stirred at ambient or high temperature for 4 h then filtered on frit. The aqueous phase is extracted 3 times with ethyl acetate. The combined organic phases are washed with salt water, dried over magnesium sulphate and concentrated to dryness in order to produce the expected boronic acid derivative.
$^1$H-NMR (DMSO-$d_6$, 300 MHz) (trans compound) δ 4.03 (t, J=7.4 Hz, 2H), 1.58 (m, 1H), 1.17 (t, J=7.4 Hz, 3H), 0.97 (m, 1H), 0.87 (td, J=7.5 Hz, J=2.7 Hz, 1H), 0.30 (m, 1H).

Example 11

Synthesis of [(trans)-2-ethoxycarbonylcyclopropyl]boronic acid MIDA ester

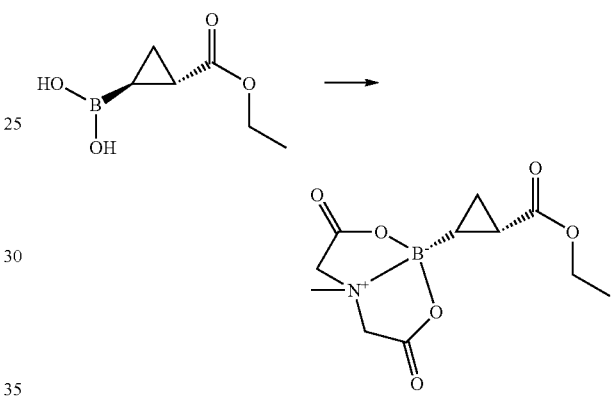

N-methyliminodiacetic acid (1 eq.) is added to a solution of boronic acid derivative (Example 10, 1 eq.) in a toluene/DMSO mixture. The reaction medium is heated under reflux with a Dean-Stark apparatus until the starting product has completely disappeared. After returning to ambient temperature, the medium is hydrolyzed by the addition of water and extracted 3 times with a THF/$Et_2$O mixture 2/1. The organic phases are dried over magnesium sulphate, filtered on frit and concentrated to dryness in order to produce a crude reaction medium. Purification by chromatography on silica (eluent: Heptane/AcOEt) produces the expected derivative.
$^1$H-NMR (DMSO-$d_6$, 300 MHz) (trans compound) δ 4.21 (dd, J=16.9 Hz, J=4.7 Hz, 2H), 4.03 (m, 4H), 2.95 (s, 3H), 1.37 (m, 1H), 1.16 (t, J=7.1 Hz, 3H), 0.96 (m, 1H), 0.68 (td, J=7.6 Hz, J=3.1 Hz, 1H), 0.42 (m, 1H).

Example 13

Synthesis of Vinyloxymethylbenzene

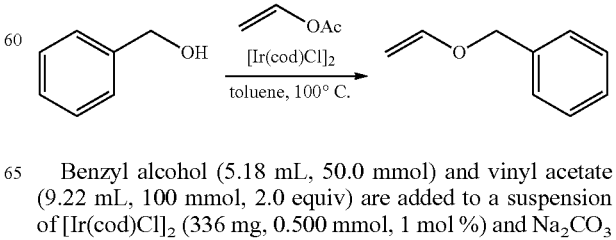

Benzyl alcohol (5.18 mL, 50.0 mmol) and vinyl acetate (9.22 mL, 100 mmol, 2.0 equiv) are added to a suspension of [Ir(cod)Cl]$_2$ (336 mg, 0.500 mmol, 1 mol %) and Na$_2$CO$_3$ (3.18 g, 30.0 mmol, 0.6 equiv) in toluene (50 mL). After stirring for 2 hours at 100° C., the mixture obtained is cooled down to ambient temperature and filtered on Celite. The filtrate is concentrated under reduced pressure and the residue purified by flash chromatography on silica gel (petroleum ether/EtOAc: 98/2) in order to produce a yellow oil (5.15 g, 77%).

$^1$H-NMR (CDCl$_3$, 400 MHz) δ 7.39-7.29 (m, 5H), 6.57 (dd, J=14.3 Hz and J=6.8 Hz, 1H), 4.76 (s, 2H), 4.30 (dd, J=14.3 Hz and J=2.0 Hz, 1H), 4.08 (dd, J=6.8 Hz and J=2.0 Hz, 1H).

Example 14

Synthesis of 2-[(E)-2-benzyloxy)ethenyl]-4,4,5,5-tetramethyl-1,3,2-dioxaborolane (2)

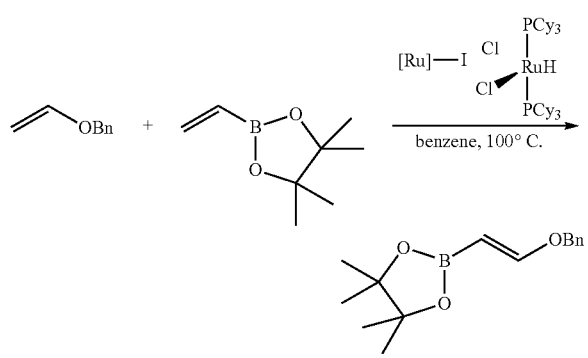

4,4,5,5-tetramethyl-2-vinyl-1,3,2-dioxaborolane (84.8 µL, 0.500 mmol) and the ruthenium catalyst [Ru]-1 (prepared by reaction of Grubbs I catalyst with 1-propanol and Et$_3$N in toluene at 75° C. for 16 h, according to Dinger, M. B.; Mol, J. C. *Organometallics* 2003, 22, 1089-1095) (3.63 mg, 5.00 µmol, 1 mol %) are added to a solution of benzyl vinyl ether (Example 13, 201 mg, 1.50 mmol, 3.0 equiv) in benzene (5.0 mL) After stirring for 24 hours at 100° C., the mixture obtained is cooled down to ambient temperature, concentrated under reduced pressure and the residue purified by flash chromatography on silica gel (petroleum ether/EtOAc: 90/10) in order to produce a yellow oil.

IR 1632, 1607, 1367, 1309, 1124, 1104, 970, 851, 814, 736, 696, 656 cm$^{-1}$; $^1$H-NMR (CDCl$_3$, 400 MHz) δ 7.36-7.29 (m, 5H), 7.15 (d, J=14.4 Hz, 1H), 4.83 (s, 2H), 4.56 (d, J=14.3 Hz, 1H), 1.26 (s, 12H); $^{13}$C-NMR (100 MHz, CDCl$_3$) δ 162.7 (d), 136.4 (s), 128.5 (d), 128.0 (d), 127.6 (d), 82.7 (s, 2C), 70.6 (t), 24.7 (q, 4C); EI-MS m/z (relative intensity) 260 (M$^{+\cdot}$, 0.3), 160 (2), 133 (M-Bpin$^+$, 2), 117 (2), 116 (13), 92 (11), 91 (100), 85 (3), 84 (6), 83 (8), 69 (2), 65 (8), 59 (2), 57 (2), 55 (2). HRMS calcd for C$_{15}$H$_{21}$BO$_3$Na (M+Na$^+$): 283.14760. Found: 283.14798.

Example 15

Synthesis of (2R*)-2-(benzyloxy)-1,1-dibromocyclopropane

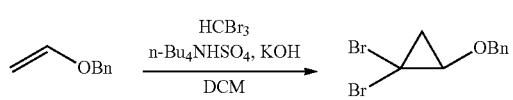

Potash (24.8 g, 442 mmol, 14.4 equivalents), tetrabutylammonium sulphate (3.13 g, 9.21 mmol, 0.3 equivalents) then tribromomethane (24.7 mL, 282 mmol, 9.2 equivalents) are added successively to a solution of vinyl benzoate (Example 13, 4.12 g, 30.7 mmol) in dichloromethane (250 mL) at 0° C. After stirring for 2 hours at ambient temperature, the reaction medium is filtered on celite, rinsed with dichloromethane, then 400 ml of water is added to the filtrate. The phases are separated and the aqueous phase is extracted with diethyl ether. The combined organic phases are dried over magnesium sulphate, filtered then evaporated to dryness under reduced pressure. The crude reaction medium is purified by chromatography on silica gel (Eluent: petroleum ether/AcOEt: 98/2) in order to produce 8.73 g (93%) of Compound 4 in the form of an orange oil.

$^1$H NMR (400 MHz, CDCl$_3$) δ 7.44-7.31 (m, 5H), 4.90 (d, AB syst, J=11.2 Hz, 1H), 4.68 (d, AB syst, J=11.2 Hz, 1H), 3.63 (dd, J=8.1 Hz and J=5.0 Hz, 1H), 1.87 (dd, J=8.9 Hz and J=8.2 Hz, 1H), 1.75 (dd, J=8.9 Hz and J=5.0 Hz, 1H); $^{13}$C NMR (100 MHz, CDCl$_3$) δ 136.4 (s), 128.6 (d, 2C), 128.4 (d, 2C), 128.3 (d), 73.4 (t), 62.9 (d), 29.8 (t), 26.8 (s).

Example 16

Synthesis of ((trans)-1-(benzyloxy)-2-bromocyclopropane

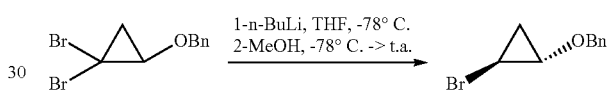

n-Butyllithium (860 µL, 2.5 M in hexane, 2.14 mmol, 1.2 equivalents) is added dropwise to a solution of dibromocyclopropane (Example 15, 546 mg, 1.78 mmol) in THF (10 mL) at –78° C. After stirring for 10 minutes at –78° C., 4 ml of methanol is added. The reaction medium is stirred for 15 minutes then left to return to ambient temperature. After stirring for 30 minutes at this temperature, water (10 mL) and diethyl ether (10 mL) are added, then the aqueous phase is extracted with diethyl ether. The combined organic phases are dried over magnesium sulphate, filtered then evaporated to dryness under reduced pressure. The crude reaction medium is purified by chromatography on silica gel (petroleum ether/AcOEt: 98/2) in order to produce 334 mg (82%) of compound 6 in the form of a yellow oil.

$^1$H NMR (400 MHz, CDCl$_3$) δ 7.39-7.30 (m, 5H), 4.61 (d, AB syst, J=11.7 Hz, 1H), 4.57 (d, AB syst, J=11.7 Hz, 1H), 3.56 (ddd, J=7.4 Hz, J=3.9 Hz and J=1.7 Hz, 1H), 2.93 (ddd, J=8.9 Hz, J=5.0 Hz and J=1.7 Hz, 1H), 1.38 (ddd, J=8.9 Hz, J=7.8 Hz and J=3.9 Hz, 1H), 1.09 (ddd, apparent td, J=7.5 Hz and J=5.0 Hz, 1H); $^{13}$C NMR (100 MHz, CDCl$_3$) δ 137.1 (s), 128.5 (d, 2C), 128.1 (d, 2C), 128.0 (d), 73.0 (t), 59.9 (d), 17.8 (d), 17.7 (t)

Example 17

Synthesis of 2-[(trans)-2-(benzyloxy)cyclopropyl]-4,4,5,5-tetramethyl-1,3,2-dioxaborolane

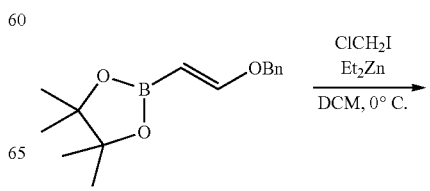

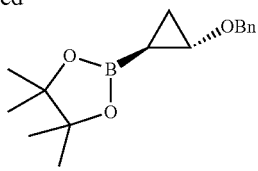

Starting from Example 14: Diethylzinc (450 µL, 1 M in hexane, 0.448 mmol, 2.0 equivalents) then chloroiodomethane (65.3 µL, 0.896 mmol, 4.0 equivalents) are added to a solution of vinyl ether (Example 14, 58.3 mg, 0.224 mmol) in dichloromethane (2.5 mL) at 0° C. After 1.5 hours at 0° C., the reaction is hydrolyzed by the addition of a saturated aqueous solution of ammonium chloride (10 mL) then the aqueous phase is extracted with dichloromethane (10 mL). The combined organic phases are dried over magnesium sulphate, filtered then evaporated to dryness under reduced pressure. The residue is purified by chromatography on silica gel (Eluent: petroleum ether/AcOEt: 90/10) in order to produce 39.7 mg (65%) of Compound 3 in the form of a colourless oil.

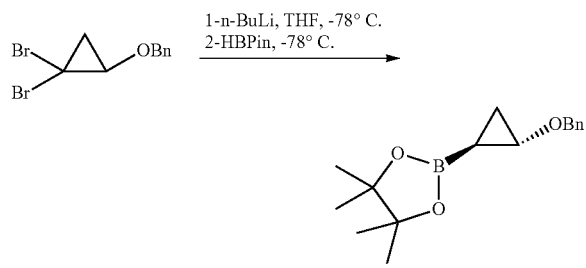

Starting from Example 15: n-Butyllithium (144 µL, 2.5 M in hexane, 0.360 mmol, 1.2 equivalents) is added to a solution of dibromocyclopropane (Example 15, 91.8 mg, 0.300 mmol) in THF (3.0 mL) at −78° C. After 15 minutes at −78° C., pinacolborane (600 µL, 1 M in THF, 2.0 equivalents) is added and the reaction mixture is heated at 50° C. for 16 hours. The reaction is then cooled down to ambient temperature then hydrolyzed by the addition of a saturated aqueous solution of ammonium chloride. The aqueous phase is extracted with diethyl ether then the combined organic phases are dried over magnesium sulphate, filtered and evaporated to dryness under reduced pressure. The residue is purified by chromatography on silica gel (Eluent: petroleum ether/AcOEt: 90/10) in order to produce Compound 3 in the form of a pale yellow oil.

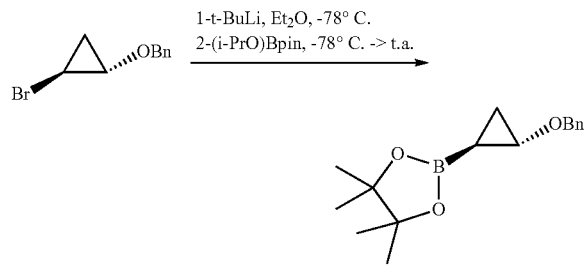

Starting from Example 16: t-Butyllithium (23.3 mL, 1.7 M in hexane, 39.6 mmol, 2.0 equivalents) is added to a solution of bromocyclopropane (Example 16, 4.50 g, 19.8 mmol) in diethyl ether (120 mL) at −78° C. After 30 minutes at this temperature, pinacol isopropoxyboronate (12.1 mL, 59.4 mmol, 3.0 equivalents) is added dropwise then the reaction medium is left to slowly return to ambient temperature for 2 hours. After 30 minutes at this temperature, the medium is hydrolyzed by the addition of a saturated aqueous solution of ammonium chloride (150 mL), the phases are separated then the aqueous phase is extracted with diethyl ether. The combined organic phases are dried over magnesium sulphate, filtered then evaporated to dryness under reduced pressure. The residue is purified by chromatography on silica gel (Eluent: petroleum ether/AcOEt: 90/10) in order to produce 4.51 g (83%) of Compound 3 in the form of a yellow oil.

IR 1435, 1411, 1380, 1371, 1317, 1199, 1142, 1089, 1067, 854, 735, 697, 700 cm$^{-1}$; $^1$H NMR (400 MHz, CDCl$_3$) δ 7.34-7.25 (m, 5H), 4.57 (d, AB syst, J=11.5 Hz, 1H), 4.51 (d, AB syst, J=11.5 Hz, 1H), 3.46 (ddd, apparent dt, J=5.9 Hz and J=3.3 Hz, 1H), 1.21 (s, 6H), 1.20 (s, 6H), 0.99 (ddd, J=11.3 Hz, J=4.6 Hz and J=3.3 Hz, 1H), 0.73 (ddd, J=7.5 Hz, J=5.9 Hz and J=4.6 Hz, 1H), 0.19 (ddd, J=11.3 Hz, J=7.5 Hz and J=3.3 Hz, 1H); $^{13}$C NMR (100 MHz, CDCl$_3$) δ 137.8 (s), 128.3 (d, 2C), 128.1 (d, 2C), 127.6 (d), 83.0 (s, 2C), 73.1 (t), 58.1 (d), 24.64 (q, 2C), 24.59 (q, 2C), 11.7 (t); EI-MS m/z (relative intensity) 183 (M-Bn$^+$, 5), 174 (2), 145 (2), 144 (3), 131 (2), 130 (8), 129 (4), 104 (3), 101 (3), 92 (11), 91 (100), 85 (3), 84 (7), 83 (10), 79 (2), 69 (2), 67 (2), 65 (7), 59 (2), 57 (2), 55 (5). HRMS calculated for C$_{16}$H$_{23}$BO$_3$Na (M+Na$^+$): 297.16325. Found: 297.16352.

Example 18

Synthesis of potassium ((trans)-2-(benzyloxy)cyclopropyltrifluoroborate

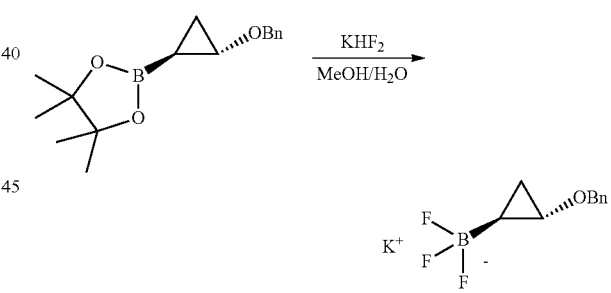

Potassium difluoride (8.93 g, 114 mmol, 7.0 equivalents) then water (14 mL) are added successively to a solution of dioxaborolane (Example 17, 4.48 g, 16.3 mmol) in methanol (70 mL) at ambient temperature. After vigorous stirring for 3 hours at ambient temperature, the reaction medium is concentrated under reduced pressure. 100 ml of acetonitrile is added to the medium followed by evaporating to dryness. This operation is carried out several times until the water is completely removed. The pasty residue is suspended in acetonitrile (50 mL) then filtered on cotton in order to remove the excess KHF$_2$. The filtrate is evaporated under reduced pressure in order to produce a solid which is washed with diethyl ether. After filtration, 3.44 g (83%) of Compound 8 is obtained in the form of a white solid.

IR 1440, 1364, 1299, 1210, 1090, 1035, 930, 909, 871, 794, 724, 693 cm$^{-1}$; $^1$H NMR (400 MHz, D$_6$-acetone) δ 7.37-7.30 (m, 4H), 7.28-7.23 (m, 1H), 4.51 (s, 2H), 3.20

(ddd, J=5.3 Hz, J=3.5 Hz and J=2.3 Hz, 1H), 0.35 (m, 1H), 0.25 (ddd, J=7.5 Hz, J=5.3 Hz and J=3.6 Hz, 1H), −0.16 (ddd, apparent m, 1H); $^{13}$C NMR (100 MHz, D$_6$-acetone) δ 140.3 (s), 128.4 (d, 2C), 127.9 (d, 2C), 127.3 (d), 72.5 (t), 58.4 (d, $J^2_{13C-B}$=3.3 Hz), 8.6 (t, $J^2_{13C-B}$=3.3 Hz), mp>172° C. (dec.).

Example 20

Synthesis of benzyl (2,2,2-tribromoethyl) ether

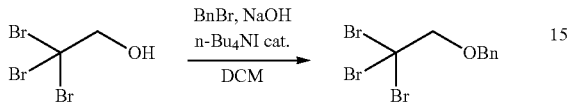

Benzyl bromide (8.41 mL, 70.7 mmol, 2.0 equivalents), tetrabutylammonium iodide (653 mg, 1.77 mmol, 5 mol %) then 25 ml of an aqueous solution of soda (2.12 g, 53.0 mmol, 1.5 equivalents) are added to a solution of 2,2,2-tribromoethanol (10.0 g, 35.3 mmol) in dichloromethane (25 mL) at 0° C. After stirring for 3 hours at ambient temperature, the phases are separated and the aqueous phase is extracted with dichloromethane. The combined organic phases are dried over magnesium sulphate, filtered then evaporated to dryness under reduced pressure. The residue is purified by chromatography on silica gel (Eluent: petroleum ether/AcOEt: 98/2 to 95/5) in order to produce 12.1 g (92%) of Compound 9 in the form of a white solid with a low melting point.

IR 1453, 1401, 1348, 1111, 1077, 991, 973, 913, 755, 726, 696, 629, 602 cm$^{-1}$; $^1$H NMR (400 MHz, CDCl$_3$) δ 7.45-7.31 (m, 5H), 4.90 (s, 2H), 4.24 (s, 2H); $^{13}$C NMR (100 MHz, CDCl$_3$) δ 136.9 (s), 128.6 (d, 2C), 128.2 (d), 127.8 (d, 2C), 84.8 (t), 74.0 (t), 40.2 (s); EI-MS m/z (relative intensity) 376 (0.3), 374 (0.8), 372 (0.8) and 372 (0.3) (M$^{+\bullet}$), 265 (2), 263 (4) and 261 (2) (M-OBn$^+$), 121 (7), 107 (2), 106 (2), 105 (4), 92 (10), 91 (100), 90 (2), 89 (2), 79 (7), 78 (3), 77 (8), 65 (10), 63 (2), 51 (5), 50 (2).

Example 21

Synthesis of (Z)-2-benzyloxy-1-bromoethylne

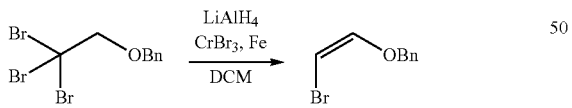

Lithium aluminium hydride (61.1 mg, 1.61 mmol, 0.6 equivalents) is added to a suspension of anhydrous chromium tribromide (prepared by drying under vacuum at 90° C. a finely divided powder of hexahydrated chromium tribromide) (948 mg, 3.22 mmol, 1.2 equivalents) and iron powder (599 mg, 10.7 mmol, 4.0 equivalents) in THF (40 mL) at 0° C. After stirring for 30 minutes at ambient temperature, 2,2,2-tribromoethyl ether (Example 20, 1.00 g, 2.68 mmol) is added in one portion. The reaction medium is stirred for 2.5 hours before being filtered on a pad of silica gel then rinsed with diethyl ether. 200 ml of water is added to the filtrate, the phases are separated and the aqueous phase is extracted with diethyl ether. The combined organic phases are dried over magnesium sulphate, filtered then evaporated to dryness under reduced pressure. The residue is purified by chromatography on silica gel (Eluent: petroleum ether/AcOEt: 96/4) in order to produce 487 mg (85%) of Compound 10 in the form of a pale yellow oil.

$^1$H NMR (400 MHz, CDCl$_3$) δ 7.41-7.31 (m, 5H), 6.65 (d, J=4.2 Hz, 1H), 5.16 (d, J=4.2 Hz, 1H), 4.97 (s, 2H); $^{13}$C NMR (100 MHz, CDCl$_3$) δ 147.0 (d), 136.4 (s), 128.6 (d, 2C), 128.3 (d), 127.4 (d, 2C), 83.3 (d), 74.4 (t)

Example 22

Synthesis of (cis)-1-(benzyloxy)-2-bromocyclopropane

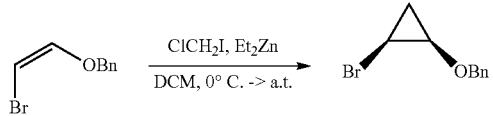 [SMILES: Br/C=C\OCc1ccccc1 ; Br[C@H]1C[C@H]1OCc1ccccc1]

Diethylzinc (4.51 mL, 1 M in hexane, 4.51 mmol, 2.0 equivalents) then chloroiodomethane (677 μL, 9.01 mmol, 4.0 equivalents) are added dropwise to a solution of vinyl ether (Example 21, 480 mg, 2.25 mmol) in dichloromethane (15 mL) at 0° C. After stirring for 9 hours at ambient temperature, an additional quantity of diethylzinc (4.51 mL, 1 M in hexane, 4.51 mmol, 2.0 equivalents) and chloroiodomethane (677 μL, 9.01 mmol, 4.0 equivalents) are added and the reaction medium is stirred for an additional 15 hours. The medium is hydrolyzed by the addition, at 0° C., of a saturated aqueous solution of ammonium chloride (15 mL), the phases are separated and the aqueous phase is extracted with dichloromethane. The combined organic phases are dried over magnesium sulphate, filtered then evaporated to dryness under reduced pressure. The residue is purified by chromatography on silica gel (Eluent: petroleum ether/AcOEt: 95/5 to 90/10) in order to produce the expected compound in the form of a pale yellow oil.

IR 1454, 1347, 1259, 1207, 1140, 1093, 1047, 1029, 973, 804, 780, 735, 696 cm$^{-1}$; $^1$H NMR (400 MHz, CDCl$_3$) δ 7.43-7.28 (m, 5H), 4.79 (d, AB syst, J=11.3 Hz, 1H), 4.59 (d, AB syst, J=11.3 Hz, 1H), 3.27 (ddd, apparent dt, J=7.3 Hz and J=4.8 Hz, 1H), 2.88 (ddd, apparent dt, J=8.3 Hz and J=5.2 Hz, 1H), 1.30 (ddd, apparent q, J=7.8 Hz, 1H), 1.07 (ddd, J=7.8 Hz, J=5.4 Hz and J=4.5 Hz, 1H); $^{13}$C NMR (100 MHz, CDCl$_3$) δ 137.3 (s), 128.4 (d, 2C), 128.1 (d, 2C), 127.9 (d), 72.9 (t), 53.7 (d), 20.5 (d), 16.0 (t); EI-MS m/z (relative intensity) 147 (M-Br$^+$, 2), 117 (4), 92 (8), 91 (100), 89 (3), 77 (2), 65 (13), 63 (2), 51 (3).

Example 23

Synthesis of 2-[(cis)-2-(benzyloxy)cyclopropyl]-4,4,5,5-tetramethyl-1,3,2-dioxaborolane

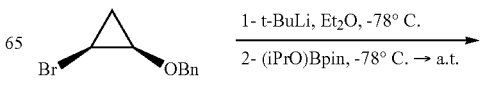

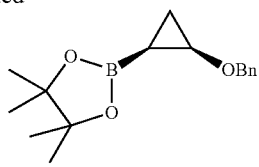

tert-Butyllithium (1.82 mL, 1.7 M in hexane, 3.09 mmol, 2.0 equivalents) is added dropwise to a solution of bromocyclopropane (Example 22, 351 mg, 1.55 mmol) in diethyl ether (10 mL) at −78° C. After stirring for 30 minutes at this temperature, pinacol isopropoxyborate (946 µL, 4.64 mmol, 3.0 equivalents) is added dropwise and the reaction medium is left to return slowly to ambient temperature over 2 hours. After stirring for 30 minutes at this temperature, the medium is hydrolyzed by the addition of a saturated aqueous solution of ammonium chloride (20 mL). The phases are separated and the aqueous phase is extracted with diethyl ether. The combined organic phases are dried over magnesium sulphate, filtered then evaporated to dryness under reduced pressure. The residue is purified by chromatography on silica gel (Eluent: petroleum ether/AcOEt: 90/10) in order to produce 254 mg (60%) of expected compound in the form of a pale yellow oil.

IR 1435, 1404, 1350, 1319, 1213, 1143, 1046, 1027, 951, 863, 851, 735, 697, 670, 611 cm-[1]; $^1$H NMR (400 MHz, CDCl$_3$) δ 7.39-7.24 (m, 5H), 4.57 (d, AB syst, J=11.7 Hz, 1H), 4.46 (d, AB syst, J=11.7 Hz, 1H), 3.60 (ddd, J=6.8 Hz, J=6.1 Hz and J=3.6 Hz, 1H), 1.25 (s, 6H), 1.23 (s, 6H), 1.05 (ddd, J=8.1 Hz, J=4.7 Hz and J=3.6 Hz, 1H), 0.84 (ddd, J=10.3 Hz, J=6.1 Hz and J=4.8 Hz, 1H), 0.05 (ddd, J=10.3 Hz, J=8.1 Hz and J=6.8 Hz, 1H); $^{13}$C NMR (100 MHz, CDCl$_3$) δ 138.2 (s), 128.1 (d, 2C), 127.8 (d, 2C), 127.4 (d), 83.1 (s, 2C), 72.9 (t), 58.2 (d), 24.8 (q, 2C), 24.7 (q, 2C), 11.3 (t); EI-MS m/z (relative intensity) 183 (M-Bn$^+$, 5), 174 (2), 144 (3), 130 (8), 129 (5), 125 (4), 104 (3), 101 (3), 92 (11), 91 (100), 85 (4), 84 (8), 83 (10), 81 (6), 79 (4), 65 (8), 57 (3), 55 (7). HRMS calculated for $C_{16}H_{23}O_3BNa$ (M+Na$^+$): 297.16325. Found: 297.16348.

Example 24

Synthesis of potassium ((cis)-2-(benzyloxy)cyclopropyltrifluoroborate

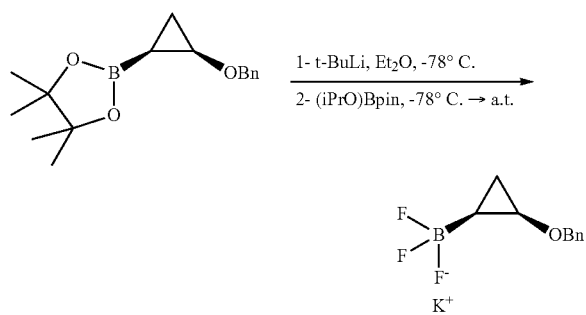

Potassium difluoride (499 g, 6.38 mmol, 7.0 equivalents) then water (1.0 mL) are added to a solution of dioxaborolane (Example 23, 250 mg, 0.912 mmol) in methanol (5 mL) at ambient temperature. After vigorous stirring for 3 hours at ambient temperature, the reaction medium is concentrated under reduced pressure. 10 ml of acetonitrile is added to the medium followed by evaporating to dryness. This operation is carried out several times until the water is completely removed. The pasty residue is suspended in acetonitrile (10 mL) then filtered on cotton in order to remove the excess KHF$_2$. The filtrate is evaporated under reduced pressure in order to produce a solid which is washed with diethyl ether. After filtration, 129 mg (56%) of compound is obtained in the form of a white solid.

IR 1356, 1338, 1207, 1098, 1029, 1010, 951, 934, 922, 905, 851, 779, 741, 698, 642 cm-[1]; $^1$H NMR (400 MHz, D$_6$-DMSO) δ 7.35-7.28 (m, 4H), 7.26-7.21 (m, 1H), 4.59 (d, AB syst, J=11.6 Hz, 1H), 4.37 (d, AB syst, J=11.6 Hz, 1H), 3.16 (m, 1H), 0.28-0.19 (m, 2H), −0.65 (m, 1H); $^{13}$C NMR (100 MHz, D$_6$-DMSO) δ 140.7 (s), 128.8 (d, 2C), 128.7 (d, 2C), 127.7 (d), 72.4 (t), 58.6 (d), 8.8 (t), mp=180° C.

Example 26

Suzuki-Miyaura Couplings on Potassium Trans Cyclopropyltrifluoroborates Bearing COOEt

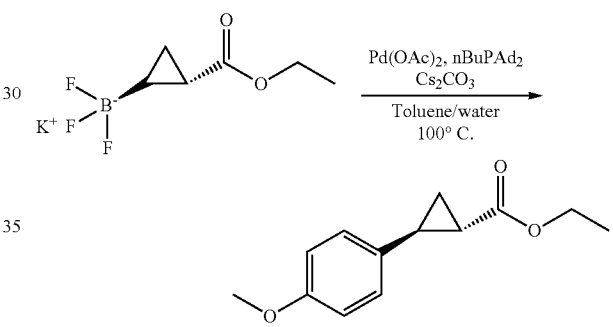

(trans)-2-(4-Methoxy-phenyl)-cyclopropyl acetic acid ethyl ester

The potassium trifluoroborate reagent (Example 1, 2.5 g, 11.4 mmol) is solubilized in a mixture of toluene (62.5 ml) and water (6.25 ml). 4-bromo-anisole (2.1 ml, 17 mmol), palladium acetate (51 mg, 0.23 mmol) and n-butyl-di-adamantylphosphine (122 mg, 0.34 mmol) are added. Nitrogen is bubbled through the medium for 10 minutes. Caesium carbonate (10 g, 30.7 mmol) is added and the mixture is heated under nitrogen at 100° C. overnight. Water is added and the expected product is extracted 3 times with ethyl acetate. The combined organic phases are dried over magnesium sulphate, filtered and concentrated in order to produce 5.4 g of a brown solid. The expected product is purified by chromatography on silica gel (heptane/ethyl acetate gradient). The expected product is obtained in the form of an orange solid (1.25 g, 5.7 mmol, yield 50%). $^1$H-NMR (CDCl$_3$, 300 MHz) δ 7.03 (d, J=8.6 Hz, 2H), 6.82 (d, J=8.7 Hz, 2H), 4.16 (q, J=7.1 Hz, 2H), 3.78 (s, 3H), 2.47 (m, 1H), 1.81 (m, 1H), 1.55 (m, 1H), 1.25 (m, 4H); LC/MS>99%, m/z (M+H)$^+$=221.4.

All the other products are obtained following the same procedure.

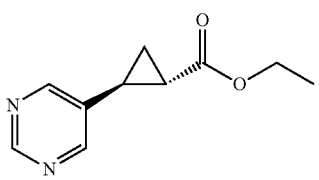

(trans)-2-Pyrimidin-5-yl-cyclopropanecarboxylic acid ethyl ester

¹H-NMR (CDCl₃, 300 MHz) δ 9.08 (s, 1H), 8.52 (s, 1H), 4.19 (q, J=7.1 Hz, 2H), 2.48 (m, 1H), 1.98 (m, 1H), 1.70 (m, 1H), 1.37 (m, 1H), 1.29 (t, J=7.1 Hz, 3H); LC/MS>99%, m/z (M+H)⁺=193.3.

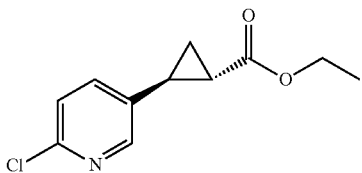

(trans)-2-(6-Chloropyridin-3-yl)-cyclopropanecarboxylic acid ethyl ester

¹H-NMR (CDCl₃, 300 MHz) δ 8.21 (d, J=2.5 Hz, 1H), 7.32 (dd, J=2.5 Hz, J=8.2 Hz, 1H), 7.23 (d, J=8.2 Hz, 1H), 4.18 (q, J=7.1 Hz, 2H), 2.50 (m, 1H), 1.90 (m, 1H), 1.65 (m, 1H), 1.28 (m, 4H); LC/MS>98%, m/z (M+H)⁺=226.3.

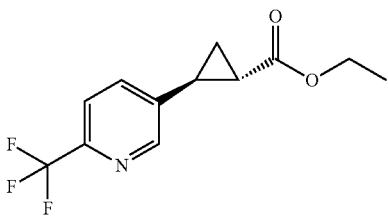 [SMILES: CCOC(=O)[C@H]1C[C@@H]1c1ccc(C(F)(F)F)nc1]

(trans)-2-(6-Trifluoromethyl-pyridin-3-yl)-cyclopropanecarboxylic acid ethyl ester ¹H-NMR (CDCl₃, 300 MHz) δ 8.54 (d, J=1.8 Hz, 1H), 7.60 (d, J=8.1 Hz, 1H), 7.50 (dd, J=1.8 Hz, J=8.1 Hz, 1H), 4.19 (q, J=7.1 Hz, 2H), 2.59 (m, 1H), 1.98 (m, 1H), 1.73 (m, 1H), 1.37 (m, 1H), 1.29 (t, J=7.1 Hz, 3H); LC/MS>99%, m/z (M+H)⁺=260.2.

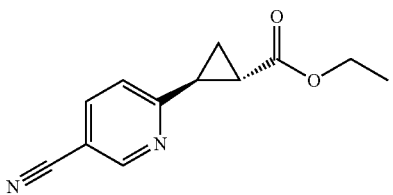 [SMILES: CCOC(=O)[C@H]1C[C@@H]1c1ccc(C#N)cn1]

(trans)-2-(5-Cyano-pyridin-2-yl)-cyclopropanecarboxylic acid ethyl ester

¹H-NMR (CDCl₃, 300 MHz) δ 8.70 (dd, J=0.8 Hz, J=2.2 Hz, 1H), 7.82 (dd, J=2.2 Hz, J=8.1 Hz, 1H), 7.37 (dd, J=0.8 Hz, J=8.1 Hz, 1H), 4.17 (q, J=7.1 Hz, 2H), 2.61 (m, 1H), 2.33 (m, 1H), 1.68 (m, 2H), 1.28 (t, J=7.1 Hz, 3H); LC/MS>98%, m/z (M+H)⁺=217.3.

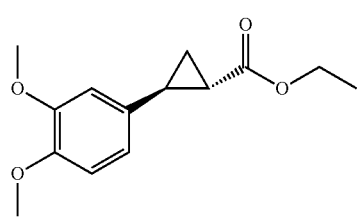 [SMILES: CCOC(=O)[C@H]1C[C@@H]1c1ccc(OC)c(OC)c1]

(trans)-2-(3,4-Dimethoxyphenyl)-cyclopropanecarboxylic acid ethyl ester

¹H-NMR (CDCl₃, 300 MHz) δ 6.77 (d, J=8.7 Hz, 1H), 6.64 (m, 2H), 4.17 (q, J=7.1 Hz, 2H), 3.87 (s, 3H), 3.85 (s, 3H), 2.49 (m, 1H), 1.83 (m, 1H), 1.55 (m, 1H), 1.28 (m, 4H); LC/MS>99%, m/z (M+H)⁺=251.3.

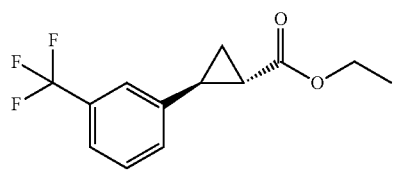 [SMILES: CCOC(=O)[C@H]1C[C@@H]1c1cccc(C(F)(F)F)c1]

(trans)-2-(3-Trifluoromethyl-phenyl)-cyclopropanecarboxylic acid ethyl ester

¹H-NMR (CDCl₃, 300 MHz) δ 7.37 (m, 4H), 4.18 (q, J=7.1 Hz, 2H), 2.57 (m, 1H), 1.93 (m, 1H), 1.65 (m, 1H), 1.34 (m, 1H), 1.28 (t, J=7.1 Hz, 3H); LC/MS>99%, m/z (M+H)⁺=259.3.

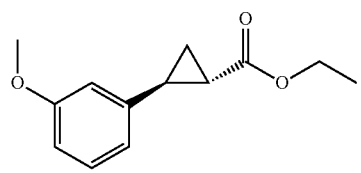 [SMILES: CCOC(=O)[C@H]1C[C@@H]1c1cccc(OC)c1]

(trans)-2-(3-Methoxyphenyl)-cyclopropanecarboxylic acid ethyl ester

¹H-NMR (CDCl₃, 300 MHz) δ 7.19 (dd, J=7.9 Hz, 1H), 6.76 (ddd, J=8.2 Hz, J=2.6 Hz, J=0.9 Hz, 1H), 6.69 (m, 1H), 6.64 (dd, J=2.6 Hz, 1H), 4.17 (q, J=7.1 Hz, 2H), 3.79 (s, 3H), 2.49 (m, 1H), 1.90 (m, 1H), 1.59 (m, 1H), 1.29 (m, 4H); LC/MS>99%, m/z (M+H)⁺=291.2.

113

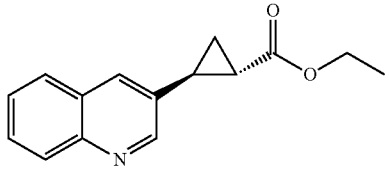 [SMILES: CCOC(=O)[C@H]1C[C@@H]1c1cnc2ccccc2c1]

(trans)-2-Quinolin-3-yl-cyclopropanecarboxylic acid ethyl ester $^1$H-NMR (CDCl$_3$, 300 MHz) δ 8.75 (d, J=2.1 Hz, 1H), 8.06 (d, J=8.4 Hz, 1H), 7.77 (d, J=2.1 Hz, 2H), 7.73 (d, J=8.4 Hz, 1H), 7.65 (ddd, J=7.7 Hz, J=7.7 Hz, J=1.4 Hz, 1H), 7.51 (ddd, J=7.7 Hz, J=7.7 Hz, J=1.4 Hz, 1H), 4.19 (t, J=7.1 Hz, 2H), 2.70 (m, 1H), 2.03 (m, 1H), 1.72 (m, 1H), 1.45 (m, 1H), 1.30 (t, J=7.1 Hz, 3H); LC/MS>99%, m/z (M+H)$^+$=242.3.

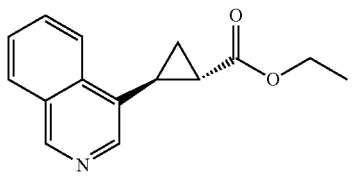 [SMILES: CCOC(=O)[C@H]1C[C@@H]1c1cncc2ccccc12]

(trans)-2-Isoquinolin-4-yl-cyclopropanecarboxylic acid ethyl ester $^1$H-NMR (CDCl$_3$, 300 MHz) δ 9.17 (bs, 1H), 8.33 (bs, 1H), 8.16 (d, J=8.4 Hz, 1H), 8.0 (m, 1H), 7.79 (ddd, J=7.7 Hz, J=7.7 Hz, J=1.4 Hz, 1H), 7.66 (ddd, J=7.7 Hz, J=7.7 Hz, J=1.4 Hz, 1H), 4.27 (q, J=7.1 Hz, 2H), 2.91 (m, 1H), 197 (m, 1H), 1.73 (m, 1H), 1.48 (m, 1H), 1.34 (t, J=7.1 Hz, 3H); LC/MS>99%, m/z (M+H)$^+$=242.3.

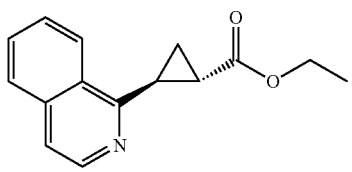 [SMILES: CCOC(=O)[C@H]1C[C@@H]1c1nccc2ccccc12]

(trans)-2-Isoquinolin-1-yl-cyclopropanecarboxylic acid ethyl ester $^1$H-NMR (CDCl$_3$, 300 MHz) δ 8.75 (m, 2H), 7.82 (m, 1H), 7.66 (m, 2H), 7.49 (d, J=5.7 Hz, 1H), 4.21 (q, J=7.2 Hz, 2H), 3.33 (m, 1H), 2.44 (m, 1H), 1.82 (m, 1H), 1.73 (m, 1H), 1.30 (t, J=7.2 Hz, 3H); LC/MS>99%, m/z (M+H)$^+$=242.3.

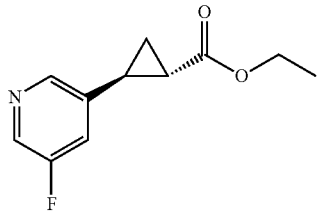

114

(trans)-2-(5-Fluoropyridin-3-yl)-cyclopropanecarboxylic acid ethyl ester $^1$H-NMR (CDCl$_3$, 300 MHz) δ 8.31 (d, J=2.6 Hz, 1H), 8.27 (bt, 1H), 7.05 (ddd, J=9.4 Hz, J=2.2 Hz, J=2.2 Hz, 1H), 4.17 (q, J=7.1 Hz, 2H), 2.52 (m, 1H), 1.93 (m, 1H), 1.67 (m, 1H), 1.32 (m, 1H), 1.28 (t, J=1.7 Hz, 3H); LC/MS>99%, m/z (M+H)$^+$=210.3.

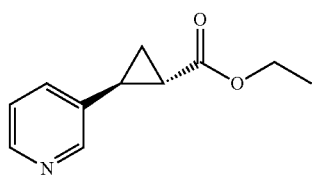

(trans)-2-Pyridin-3-yl-cyclopropanecarboxylic acid ethyl ester $^1$H-NMR (CDCl$_3$, 300 MHz) δ 8.45 (m, 2H), 7.37 (ddd, J=7.9 Hz, J=3.4 Hz, J=3.4 Hz, 1H), 7.23 (d, J=7.9 Hz, 1H), 4.18 (q, J=7.1 Hz, 2H), 2.52 (m, 1H), 1.93 (m, 1H), 1.65 (m, 1H), 1.32 (m, 1H), 1.29 (t, J=7.1 Hz, 3H); LC/MS>99%, m/z (M+H)$^+$=192.2.

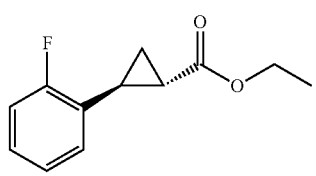

(trans)-2-(2-Fluorophenyl)-cyclopropanecarboxylic acid ethyl ester $^1$H-NMR (CDCl$_3$, 300 MHz) δ 7.18 (m, 1H), 7.00 (m, 3H), 4.18 (q, J=7.0 Hz, 2H), 2.66 (m, 1H), 1.94 (m, 1H), 1.60 (m, 1H), 1.35 (m, 1H), 1.29 (t, J=7.0 Hz, 3H); LC/MS>99%, m/z (M+H)$^+$=209.3.

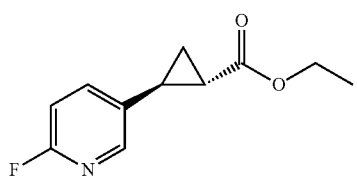

(trans)-2-(6-Fluoropyridin-3-yl)-cyclopropanecarboxylic acid ethyl ester $^1$H-NMR (CDCl$_3$, 300 MHz) δ 8.01 (m, 1H), 7.44 (ddd, J=8.9 Hz, J=2.5 Hz, J=2.5 Hz, 1H), 6.83 (dd, J=8.9 Hz, J=2.5 Hz, 1H), 4.16 (q, J=7.1 Hz, 2H), 2.45 (m, 1H), 1.86 (m, 1H), 1.61 (m, 1H), 1.26 (m, 4H); LC/MS>99%, m/z (M+H)$^+$=210.3.

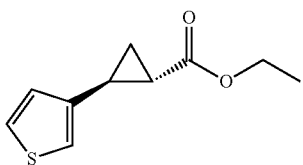

(trans)-2-Thiophen-3-yl-cyclopropanecarboxylic acid ethyl ester $^1$H-NMR (CDCl$_3$, 300 MHz) δ 7.26 (dd, J=5.0 Hz, J=3.0 Hz, 1H), 6.97 (m, 1H), 6.84 (dd, J=5.0 Hz, J=3.0 Hz, 1H), 4.17 (q, J=7.1 Hz, 2H), 2.55 (m, 1H), 1.87 (m, 1H), 1.57 (m, 1H), 1.29 (m, 4H); LC/MS>99%, m/z (M+H)$^+$=197.1.

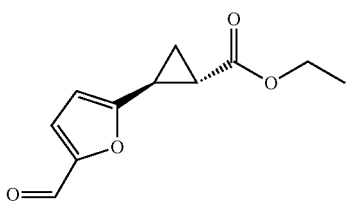

(trans)-2-(5-Formyl-furan-2-yl)-cyclopropanecarboxylic acid ethyl ester $^1$H-NMR (CDCl$_3$, 300 MHz) δ 9.49 (s, 1H), 7.16 (d, J=3.6 Hz, 1H), 6.32 (d, J=3.6 Hz, 1H), 4.17 (q, J=7.2 Hz, 2H), 2.58 (m, 1H), 2.18 (m, 1H), 1.59 (m, 2H), 1.28 (t, J=7.2 Hz, 3H); LC/MS>99%, m/z (M+H)$^+$=209.2.

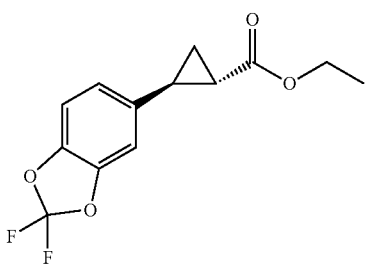 [SMILES: CCOC(=O)[C@H]1C[C@@H]1c1ccc2c(c1)OC(F)(F)O2]

(trans)-2-(2,2-Difluoro-benzo[1,3]dioxol-5-yl)-cyclopropanecarboxylic acid ethyl ester $^1$H-NMR (CDCl$_3$, 300 MHz) δ 6.95 (d, J=8.3 Hz, 1H), 6.80 (dd, J=8.3 Hz, J=1.7 Hz, 1H), 6.84 (d, J=1.7 Hz, 1H), 4.17 (q, J=7.1 Hz, 2H), 2.51 (m, 1H), 1.84 (m, 1H), 1.60 (m, 1H), 1.27 (m, 4H); LC/MS>99%, m/z (M+H)$^+$=271.2.

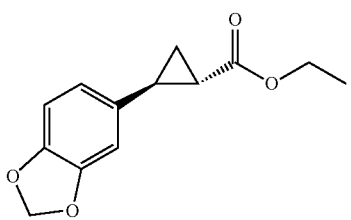 [SMILES: CCOC(=O)[C@H]1C[C@@H]1c1ccc2c(c1)OCO2]

(trans)-2-Benzo[1,3]dioxol-5-yl-cyclopropanecarboxylic acid ethyl ester $^1$H-NMR (CDCl$_3$, 300 MHz) δ 6.71 (d, J=7.98 Hz, 1H), 6.60 (ddd, J=7.9 Hz, J=1.8 Hz, J=0.42 Hz, 1H), 6.56 (d, J=1.8 Hz, 1H), 4.16 (q, J=7.1 Hz, 2H), 2.45 (m, 1H), 1.80 (m, 1H), 1.53 (m, 1H), 1.24 (m, 4H); LC/MS>99%, m/z

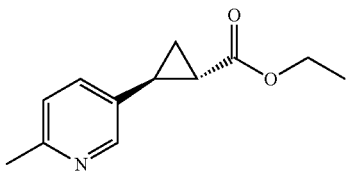

(trans)-2-(6-Methylpyridin-3-yl)-cyclopropanecarboxylic acid ethyl ester $^1$H-NMR (CDCl$_3$, 300 MHz) δ 8.34 (d, J=2.3 Hz, 1H), 7.25 (dd, J=8.2 Hz, J=2.3 Hz, 1H), 7.07 (d, J=8.2 Hz, 1H), 4.17 (q, J=7.1 Hz, 2H), 2.50 (m, 1H), 1.89 (m, 1H), 1.62 (m, 1H), 1.30 (m, 4H); LC/MS>99%, m/z (M+H)$^+$=206.3

(trans)-2-(5-Fluoropyridin-2-yl)-cyclopropanecarboxylic acid ethyl ester $^1$H-NMR (CDCl$_3$, 300 MHz) δ 8.30 (d, J=2.7 Hz, 1H), 7.27 (m, 2H), 4.17 (q, J=7.1 Hz, 2H), 2.58 (m, 1H), 2.2 (m, 1H), 1.60 (m, 1H), 1.28 (m, 4H); LC/MS>99%, m/z (M+H)$^+$=210.3

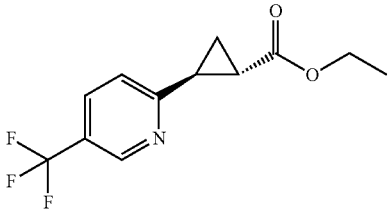 [SMILES: CCOC(=O)[C@H]1C[C@@H]1c1ccc(C(F)(F)F)cn1]

(trans)-2-(5-Trifluoromethyl-pyridin-2-yl)-cyclopropanecarboxylic acid ethyl ester $^1$H-NMR (CDCl$_3$, 300 MHz) δ 8.68 (s, 1H), 7.78 (dd, J=8.2 Hz, J=1.8 Hz, 1H), 7.35 (d, J=8.2 Hz, 1H), 4.16 (q, J=7.2 Hz, 2H), 2.62 (m, 1H), 2.30 (m, 1H), 1.65 (m, 2H), 1.27 (t, J=7.2 Hz, 3H); LC/MS>99%, m/z (M+H)$^+$=260.3

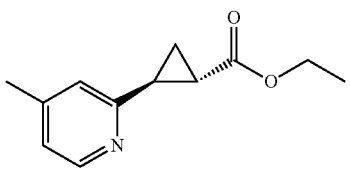

(trans)-2-(4-Methylpyridin-2-yl)-cyclopropanecarboxylic acid ethyl ester $^1$H-NMR (CDCl$_3$, 300 MHz) δ 8.31 (d, J=5.0 Hz, 1H), 7.07 (d, J=0.7 Hz, 1H), 6.93 (dd, J=5.0 Hz, J=0.7 Hz, 1H), 4.18 (q, J=7.2 Hz, 2H), 2.55 (m, 1H), 2.23 (m, 1H), 1.6 (m, 2H), 1.29 (t, 7.2 Hz, 3H); LC/MS>99%, m/z (M+H)$^+$=206.3

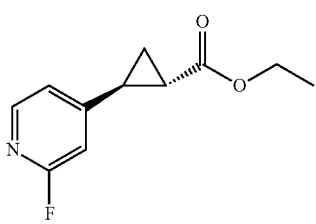

(trans)-2-(2-Fluoropyridin-4-yl)-cyclopropanecarboxylic acid ethyl ester $^1$H-NMR (CDCl$_3$, 300 MHz) δ 8.11 (d, J=5.3 Hz, 1H), 6.89 (dt, J=5.3 Hz, J=1.6 Hz, 1H), 6.64 (s, 1H), 4.19 (q, J=7.1 Hz, 2H), 2.52 (m, 1H), 2.02 (m, 1H), 1.72 (m, 1H), 1.39 (m, 1H), 1.35 (t, J=7.1 Hz, 3H); LC/MS>99%, m/z (M+H)$^+$=210.3

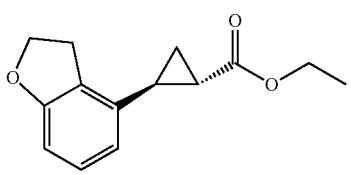 [SMILES: CCOC(=O)[C@H]1C[C@@H]1c1cccc2c1CCO2]

(trans)-2-(2,3-Dihydro-benzofuran-4-yl)-cyclopropanecarboxylic acid ethyl ester $^1$H-NMR (CDCl$_3$, 300 MHz) δ 7.04 (dd, J=7.8 Hz, 1H), 6.65 (d, J=7.1 Hz, 1H), 6.40 (d, J=7.8 Hz, 1H), 4.60 (t, J=8.7 Hz, 2H), 4.18 (q, 7.1 Hz, 2H), 3.24 (d, J=7.8 Hz, 2H), 2.42 (m, 1H), 1.90 (m, 1H), 1.58 (m, 1H), 1.30 (m, 4H).

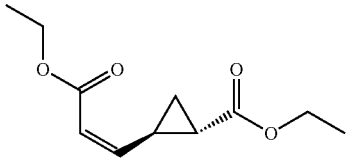

Ethyl-(trans)-2-[(Z)-3-ethoxy-3-oxo-prop-1-enyl]cyclopropanecarboxylate $^1$H-NMR (CDCl$_3$, 300 MHz) δ 5.77 (dm, J=11.4 Hz, 1H), 5.44 (dd, J=11.4 Hz, J=10.8 Hz, 1H), 4.19 (q, J=7.0 Hz, 2H), 4.13 (q, J=7.0 Hz, 2H), 3.40 (m, 1H), 1.74 (m, 1H), 1.59 (m, 1H), 1.29 (t, J=7.0 Hz, 3H), 1.26 (t, J=7.0 Hz, 3H), 1.03 (m, 1H).

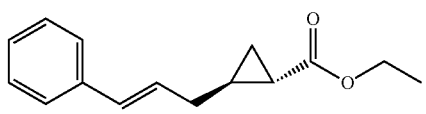 [SMILES: CCOC(=O)[C@H]1C[C@@H]1C/C=C/c1ccccc1]

Ethyl-(trans)-2-[(E)-cinnamyl]cyclopropanecarboxylate $^1$H-NMR (CDCl$_3$, 300 MHz) δ 7.4-7.12 (m, 5H), 6.40 (d, J=15.9 Hz, 1H), 6.17 (dt, J=15.9 Hz, J=6.9 Hz, 1H), 4.09 (q, J=7.0 Hz, 2H), 2.21 (m, 2H), 1.43 (m, 2H), 1.23 (t, J=7.0 Hz, 3H), 1.20 (m, 1H), 0.77 (m, 1H).

Example 27

Suzuki-Miyaura Couplings on Potassium Trans Cyclopropyltrifluoroborates Bearing —CH$_2$—NHZ The following products are obtained according to the procedure presented in Example 26, starting from the potassium trifluoroborate reagent described in Example 9.

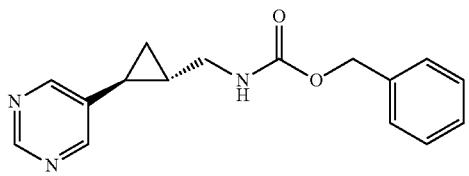 [SMILES: O=C(NC[C@H]1C[C@@H]1c1cncnc1)OCc1ccccc1]

((trans)-2-Pyrimidin-5-yl-cyclopropylmethyl)-carbamic acid benzyl ester $^1$H-NMR (CDCl$_3$, 300 MHz) δ 9.04 (s, 1H); 8.46 (s, 2H); 7.35 (m, 5H); 5.13 (s, 2H); 5.02 (bs, 1H); 3.29 (m, 2H); 1.87 (m, 1H); 1.42 (m, 1H); 1.08 (m, 2H).

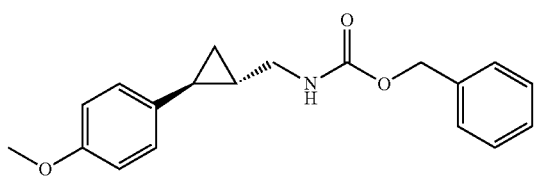 [SMILES: COc1ccc([C@H]2C[C@@H]2CNC(=O)OCc2ccccc2)cc1]

[(trans)-2-(4-Methoxy-phenyl)-cyclopropylmethyl]-carbamic acid benzyl ester $^1$H-NMR (CDCl$_3$, 300 MHz) δ 7.34 (m, 5H); 6.97 (d, J=8.5 Hz, 2H); 6.80 (d, J=8.5 Hz, 2H); 5.11 (s, 2H); 4.93 (bs, 1H); 3.78 (s 3H); 3.22 (m, 2H); 1.77 (m, 1H); 1.24 (m, 1H); 0.87 (m, 2H).

119

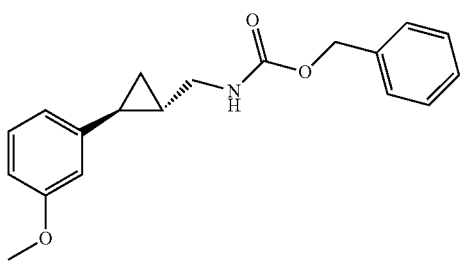 [SMILES: COc1cccc([C@H]2C[C@@H]2CNC(=O)OCc2ccccc2)c1]

(trans)-2-(3-Methoxy-phenyl)-cyclopropylmethyl]-carbamic acid benzyl ester

¹H-NMR (CDCl₃, 300 MHz) δ 7.37 (m, 5H); 7.18 (dd, J=7.9 Hz, J=7.9 Hz, 1H); 6.72 (dd, J=2.5 Hz, J=8.2 Hz, 1H); 6.65 (d, J=8.2 Hz, 1H); 6.60 (m, 1H); 5.12 (s, 2H; 4.92 (s, 1H); 3.80 (s, 3H); 3.25 (m, 2H; 1.80 (m, 1H); 1.34 (m, 1H; 0.95 (m, 2H).

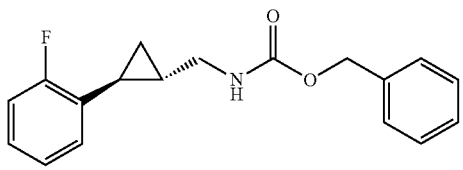 [SMILES: O=C(NC[C@H]1C[C@@H]1c1ccccc1F)OCc1ccccc1]

[(trans)-2-(2-Fluoro-phenyl)-cyclopropylmethyl]-carbamic acid benzyl ester

¹H-NMR (CDCl₃, 300 MHz) δ 7.36 (m, 5H); 7.16 (m, 1H); 7.03 (m, 2H); 6.92 (dd, J=7.0 Hz, J=7.0 Hz, 1H); 5.13 (s, 2H); 5.01 (bs, 1H); 3.43 (m, 1H); 3.14 (m, 1H); 1.98 (m, 1H); 1.31 (m, 1H); 0.98 (m, 2H).

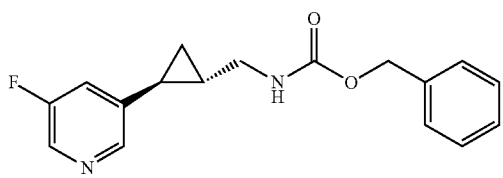 [SMILES: O=C(NC[C@H]1C[C@@H]1c1cncc(F)c1)OCc1ccccc1]

[(trans)-2-(5-Fluoro-pyridin-3-yl)-cyclopropylmethyl]-carbamic acid benzyl ester*

¹H-NMR (CDCl₃, 300 MHz) δ 8.25 (d, J=2.6 Hz, 1H); 8.21 (s, 1H); 7.34 (m, 5H); 6.96 (d, J=9.4 Hz, 1H); 5.11 (s, 2H); 5.00 (bs, 1H); 3.25 (m, 2H); 1.87 (m, 1H); 1.35 (m, 1H); 1.00 (m, 2H).

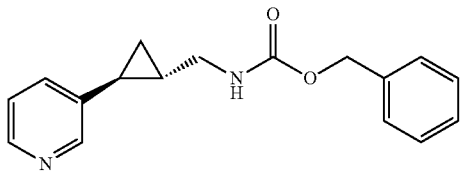 [SMILES: O=C(NC[C@H]1C[C@@H]1c1cccnc1)OCc1ccccc1]

120

((trans)-2-Pyridin-3-yl-cyclopropylmethyl)-carbamic acid benzyl ester

¹H-NMR (CDCl₃, 300 MHz) δ 8.40 (m, 2H); 7.34 (m, 6H); 7.21 (m, 1H); 5.10 (s, 2H); 4.96 (bs, 1H); 3.26 (m, 2H); 1.85 (m, 1H); 1.34 (m, 1H); 1.00 (m, 2H).

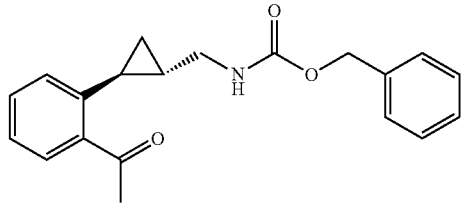 [SMILES: CC(=O)c1ccccc1[C@H]1C[C@@H]1CNC(=O)OCc1ccccc1]

[(trans)-2-(2-Acetyl-phenyl)-cyclopropylmethyl]-carbamic acid benzyl ester

¹H-NMR (CDCl₃, 300 MHz) δ 7.68 (dd, J=1.2 Hz, J=7.6 Hz, 1H); 7.34 (m, 7H); 7.08 (d, J=7.6 Hz, 1H); 5.13 (s, 2H); 3.79 (m, 1H); 2.76 (m, 1H); 2.63 (s, 3H); 2.26 (m, 1H); 1.10 (m, 2H); 0.85 (m, 1H).

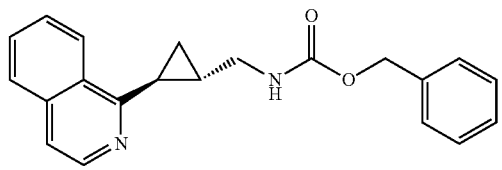 [SMILES: O=C(NC[C@H]1C[C@@H]1c1nccc2ccccc12)OCc1ccccc1]

((trans)-2-Isoquinolin-1-yl-cyclopropylmethyl)-carbamic acid benzyl ester

¹H-NMR (CDCl₃, 300 MHz) δ 8.39 (d, J=8.3 Hz, 1H); 8.35 (d, J=5.7 Hz, 1H); 7.82 (d, J=7.5 Hz, 1H); 7.65 (m, 2H); 7.46 (dd, J=0.6 Hz; J=5.7 Hz, 1H); 7.34 (m, 5H); 5.13 (s, 2H); 5.01 (bs, 1H); 3.43 (m, 2H); 2.75 (m, 1H); 1.84 (m, 1H); 1.55 (m, 1H); 1.12 (m, 1H).

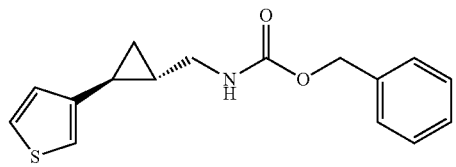 [SMILES: O=C(NC[C@H]1C[C@@H]1c1ccsc1)OCc1ccccc1]

((trans)-2-Thiophen-3-yl-cyclopropylmethyl)-carbamic acid benzyl ester

¹H-NMR (CDCl₃, 300 MHz) δ 7.34 (m, 5H); 7.21 (dd, J=3.0 Hz, J=4.9 Hz, 1H); 6.85 (s, 1H); 6.78 (d, J=4.9 Hz, 1H); 5.11 (s, 2H); 4.90 (bs, 1H); 3.22 (m, 2H); 1.85 (m, 1H); 1.28 (m, 1H); 0.87 (m, 2H).

Example 28

Suzuki-Miyaura Couplings on Potassium Trans Cyclopropyltrifluoroborates Bearing —OBn

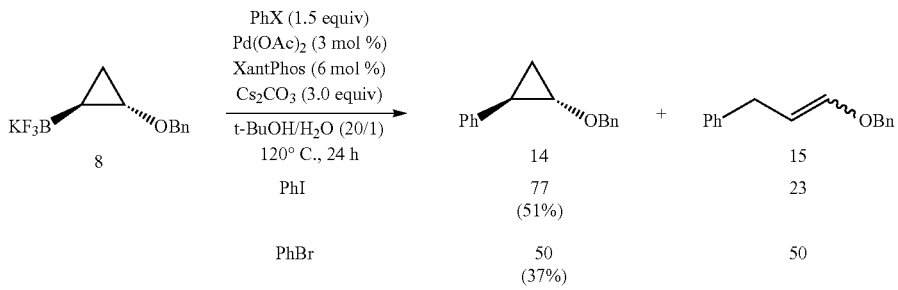

| | 14 | 15 |
|---|---|---|
| PhI | 77 (51%) | 23 |
| PhBr | 50 (37%) | 50 |

Suzuki-Miyaura Coupling Between Compound 8 and Iodobenzene:

Palladium diacetate (1.3 mg, 5.9 μmol, 3 mol %), Xant-Phos (6.8 mg, 12 μmol, 6 mol %), caesium carbonate (192 mg, 0.590 mmol, 3.0 equivalents), potassium cyclopropyl-trifluoroborate 8 (50.0 mg, 0.197 mmol), tert-butanol (1.0 mL), water (50 μL) and finally iodobenzene (33 μL, 0.30 mmol, 1.5 equivalents) are successively added into a sealed tube, under an inert atmosphere. The tube is then closed (Teflon stopper) then immersed in an oil bath pre-heated to 120° C. After stirring for 24 hours at this temperature, the reaction medium is cooled down to ambient temperature then filtered on a celite pad (rinsing with AcOEt) and evaporated to dryness under reduced pressure. Purification by chromatography on silica gel (Eluent: petroleum ether/AcOEt: 95/5) produces a mixture of Compound 14 and enol ether 15 in a ratio of 77/23. The separation of this mixture can be obtained by preparative TLC on a silica plate (Eluent: petroleum ether/AcOEt: 95/5) in order to produce 22.5 mg (51%) of Compound 14 in the form of a colourless oil.

Suzuki-Miyaura Coupling Between Compound 8 and Bromobenzene:

Palladium diacetate (1.3 mg, 5.9 μmol, 3 mol %), Xant-Phos (6.8 mg, 12 μmol, 6 mol %), caesium carbonate (192 mg, 0.590 mmol, 3.0 equivalents), potassium cyclopropyl-trifluoroborate 8 (50.0 mg, 0.197 mmol), tert-butanol (1.0 mL), water (50 μL) and finally bromobenzene (31.1 μL, 0.295 mmol, 1.5 equivalents) are successively added into a sealed tube, under an inert atmosphere. The tube is then closed (Teflon stopper) then immersed in an oil bath pre-heated to 120° C. After stirring for 24 hours at this temperature, the reaction medium is cooled down to ambient temperature then filtered on a celite pad (rinsing with AcOEt) and evaporated to dryness under reduced pressure. Purification by chromatography on silica gel (Eluent: petroleum ether/AcOEt: 95/5) produces a mixture of cyclopropene 14 and enol ether 15 in a ratio of 50/50. Separation of this mixture can be obtained by preparative TLC on a silica plate (Eluent: petroleum ether/AcOEt: 95/5) in order to produce 16.4 mg (37%) of Compound 14 in the form of a colourless oil.

[(1R*,2S*)-2-(Benzyloxy)cyclopropyl]benzene (14)

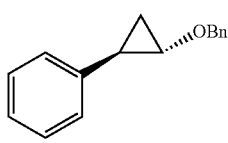 [SMILES: c1ccc(CO[C@H]2C[C@@H]2c2ccccc2)cc1]

IR 1604, 1496, 1454, 1366, 1260, 1208, 1146, 1092, 1071, 1024, 910, 870, 735, 695, 613 cm$^{-1}$; $^1$H NMR (400 MHz, CDCl$_3$) δ 7.35-7.22 (m, 7H), 7.18-7.13 (m, 1H), 7.01-6.98 (m, 2H), 4.63 (d, AB syst, J=11.7 Hz, 1H), 4.60 (d, AB syst, J=11.7 Hz, 1H), 3.44 (ddd, J=6.5 Hz, J=3.6 Hz and J=2.6 Hz, 1H), 2.15 (ddd, J=10.2 Hz, J=6.4 Hz and J=2.6 Hz, 1H), 1.34 (ddd, J=10.2 Hz, J=6.1 Hz and J=3.6 Hz, 1H), 1.05 (ddd, apparent q, J=6.4 Hz, 1H); $^{13}$C NMR (100 MHz, CDCl$_3$) δ 141.1 (s), 137.8 (s), 128.4 (d, 2C), 128.3 (d, 2C), 128.0 (d, 2C), 127.8 (d), 125.9 (d, 2C), 125.7 (d), 73.0 (t), 61.7 (d), 23.9 (d), 16.0 (t); EI-MS m/z (relative intensity) 224 (Mt$^{+\cdot}$, 0.1), 181 (3), 180 (21), 133 (M-Bn$^+$, 17), 115 (3), 106 (9), 105 (100), 104 (7), 103 (10), 92 (10), 91 (87), 89 (3), 79 (15), 78 (6), 77 (15), 65 (17), 63 (4), 51 (7). HRMS calculated for C$_{16}$H$_{16}$ONa (M+Na$^+$): 247.10934. Found: 247.10901.

[3-(Benzyloxy)prop-2-en-1-yl]benzene (15)

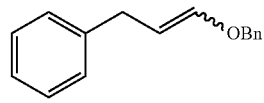 [SMILES: C(=COCc1ccccc1)Cc1ccccc1]

$^1$H NMR (400 MHz, CDCl$_3$) (Z)-isomer δ 7.39-7.14 (m, 10H), 6.14 (dt, J=6.2 Hz and J=1.2 Hz, 1H), 4.84 (s, 2H), 4.62 (td, J=7.5 Hz and J=6.2 Hz, 1H, H$_2$), 3.48 (br d, J=7.5 Hz, 2H, H$_7$); (E)-isomer δ 7.39-7.14 (m, 10H, H$_{Ar}$), 6.44 (dt, J=12.6 Hz and J=1.2 Hz, 1H, H$_3$), 5.04 (dt, J=12.6 Hz and J=7.4 Hz, 1H, H$_2$), 4.74 (s, 2H, H$_4$), 3.27 (br d, J=7.1 Hz, 2H, H$_7$); $^{13}$C NMR (100 MHz, CDCl$_3$) (Z)-isomer δ 145.1 (d, C$_3$), 141.6 (s, C$_5$ or C$_9$), 137.6 (s, C$_9$ or C$_5$), 128.5 (d), 128.4 (d) and 128.3 (d) (6 C$_{Ar}$), 127.6 (d, 2C, C$_{Ar}$), 125.7 (d, 2C, C$_{Ar}$), 106.4 (d, C$_2$), 73.7 (t, C$_4$), 30.3 (t, C$_7$); (E)-isomer δ 146.9 (d, C$_3$), 141.5 (s, C$_5$ or C$_9$), 137.1 (s, C$_9$ or C$_5$), 128.5 (d), 128.4 (d), 128.3 (d) (6 C$_{Ar}$), 127.9 (d, 2C, C$_{Ar}$), 125.9 (d, 2C, C$_{Ar}$), 103.8 (d, C$_2$), 71.1 (t, C$_4$), 34.1 (t, C$_7$).

Example 29

Suzuki-Miyaura Couplings on Potassium Cis Cyclopropyltrifluoroborates Bearing COOEt

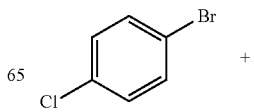

-continued

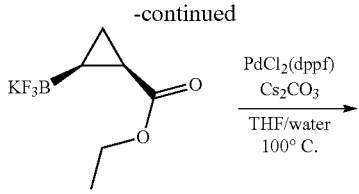

(cis)-2-(4-chlorophenyl)cyclopropyl acetic acid ethyl ester

4-Bromochlorobenzene (8.7 g, 45.5 mmol), palladium-diphenylphosphinoferrocene (832 mg, 1.14 mmol) and caesium carbonate (22.2 g, 68.2 mmol) are added successively to a solution of potassium cis trifluoroborate (5.0 g, 22.7 mmol) in a mixture of THF (20 ml) and water (20 ml). The reaction medium purged with nitrogen is heated at 100° C. for 48 hours. The insoluble part is filtered on Clarcel®, then washed with water and ethyl acetate. The phases are separated and the aqueous phase is extracted 3 times with ethyl acetate. The organic phases are dried over magnesium sulphate, filtered, concentrated to dryness in order to produce 5.55 g of a brown oil. Purification by chromatography on silica gel (Eluent: Heptane/AcOEt gradient) produces the expected compound in the form of a brown oil.

$^1$H-NMR (CDCl$_3$, 300 MHz) δ 7.23 (m, 4H), 3.92 (q, J=7.5 Hz, 2H), 2.54 (q, J=9.0 Hz, 1H), 2.10 (m, 1H), 1.69 (m, 1H), 1.33 (m, 1H), 1.04 (t, J=7.5 Hz, 3H)

All the other products are obtained following the same procedure.

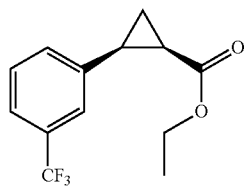 [SMILES: CCOC(=O)[C@@H]1C[C@@H]1c1cccc(C(F)(F)F)c1]

(cis)-2-(3-trifluoromethylphenyl)cyclopropanecarboxylic acid ethyl ester $^1$H-NMR (CDCl$_3$, 300 MHz) δ 7.38 (m, 4H), 3.81 (qd, J$_1$=7.3 Hz, J$_2$=1.1 Hz, 2H), 2.53 (q, J=8.4 Hz, 1H), 2.06 (m, 1H), 1.66 (m, 1H), 1.32 (m, 1H), 0.91 (t, J=7.3 Hz, 3H); LC/MS>90%, m/z (M+H)$^+$=259.3

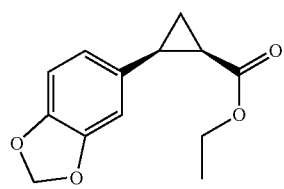 [SMILES: CCOC(=O)[C@@H]1C[C@@H]1c1ccc2c(c1)OCO2]

(cis)-2-(1,3-benzodioxol-5-yl)cyclopropanecarboxylic acid ethyl ester $^1$H-NMR (acetone-d6, 300 MHz) δ 6.65 (m, 3H), 5.84 (s, 2H), 3.78 (q, J=6.8 Hz, 2H), 2.45 (q, J=8.2 Hz, 1H), 1.45 (m, 1H), 1.21 (m, 1H), 0.92 (t, J=6.8 Hz, 3H); LC/MS>98%, m/z (M+H)$^+$=235.3

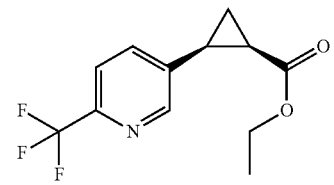

(cis)-2-(6-Trifluoromethyl-pyridin-3-yl)cyclopropanecarboxylic acid ethyl ester $^1$H-NMR (acetone-d6, 300 MHz) δ 8.54 (s, 1H), 7.8 (dm, J=9.4 Hz, 1H), 7.62 (d, J=9.4 Hz, 1H), 3.75 (m, 2H), 2.64 (q, J=8.6 Hz, 1H), 2.14 (m, 1H), 1.62 (m, 1H), 1.41 (m, 1H), 0.86 (t, J=7.7 Hz, 3H); LC/MS>96%, m/z (M+H)$^+$=260.3

Example 30

Suzuki-Miyaura Couplings on Potassium Cis Cyclopropyltrifluoroborates Bearing —OBn

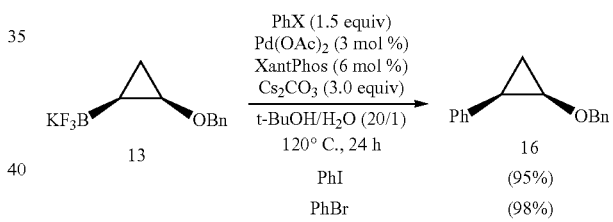

Suzuki-Miyaura Coupling Between Compound 13 and Iodobenzene:

Palladium diacetate (1.3 mg, 5.9 μmol, 3 mol %), Xant-Phos (6.8 mg, 12 μmol, 6 mol %), caesium carbonate (192 mg, 0.590 mmol, 3.0 equivalents), potassium cyclopropyltrifluoroborate 13 (50.0 mg, 0.197 mmol), tert-Butanol (1.0 mL), water (50 μL) and finally iodobenzene (33 μL, 0.30 mmol, 1.5 equivalents) are successively added, under an inert atmosphere, into a sealed tube. The tube is then closed (Teflon stopper) then immersed in an oil bath pre-heated to 120° C. After stirring for 24 hours at this temperature, the reaction medium is cooled down to ambient temperature then filtered on a celite pad (rinsing with AcOEt) and evaporated to dryness under reduced pressure. Purification by chromatography on silica gel (Eluent: petroleum ether/AcOEt: 97/3 then 96/4) produces 42.0 mg (95%) of Compound 16 in the form of a colourless oil.

Suzuki-Miyaura Coupling Between Compound 13 and Bromobenzene:

Palladium diacetate (1.3 mg, 5.9 μmol, 3 mol %), Xant-Phos (6.8 mg, 12 μmol, 6 mol %), caesium carbonate (192 mg, 0.590 mmol, 3.0 equivalents), potassium cyclopropyltrifluoroborate 13 (50.0 mg, 0.197 mmol), tert-Butanol (1.0 mL), water (50 μL) and finally bromobenzene (31.1 μL, 0.295 mmol, 1.5 equivalents) are successively added, under an inert atmosphere, into a sealed tube. The tube is then closed (Teflon stopper) then immersed in an oil bath preheated to 120° C. After stirring for 24 hours at this temperature, the reaction medium is cooled down to ambient temperature then filtered on a celite pad (rinsing with AcOEt) and evaporated to dryness under reduced pressure. Purification by chromatography on silica gel (Eluent: petroleum ether/AcOEt: 97/3 then 96/4) produces 43.3 mg (98%) of Compound 16 in the form of a colourless oil.

[(1R*,2R*)-2-(Benzyloxy)cyclopropyl]benzene

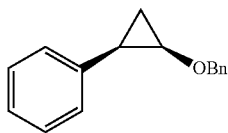 [SMILES: c1ccc(CO[C@@H]2C[C@@H]2c2ccccc2)cc1]

IR 1603, 1497, 1454, 1345, 1222, 1182, 1083, 1047, 1027, 938, 766, 733, 694, 642 cm$^{-1}$; $^1$H NMR (400 MHz, CDCl$_3$) δ 7.32-7.18 (m, 8H, H$_{Ar}$), 7.10-7.07 (m, 2H, H$_{10}$), 4.27 (d, AB syst, J=11.2 Hz, 1H, H$_4$), 4.16 (d, AB syst, J=11.2 Hz, 1H, H$_4$·), 3.59 (ddd, apparent td, J=6.4 Hz and J=3.9 Hz, 1H, H$_3$), 2.02 (ddd, J=9.5 Hz, J=7.2 Hz and J=6.3 Hz, 1H, H$_2$), 1.23-1.14 (m, 2H, H$_1$); $^{13}$C NMR (100 MHz, CDCl$_3$) δ 137.7 (s, C$_5$ or C$_9$), 137.5 (s, C$_9$ or C$_5$), 128.21 (d, 2C), 128.16 (d, 2C), 127.93 (d, 2C), 127.88 (d, 2C) (8 C$_{Ar}$), 127.6 (d, C$_8$), 125.6 (d, C$_{10}$), 72.7 (t, C$_4$), 58.4 (d, C$_3$), 22.8 (d, C$_2$), 12.9 (t, CO; EI-MS m/z (relative intensity) 224 (M$^{+\cdot}$, 0.1), 181 (4), 180 (23), 133 (M-Bn$^+$, 16), 115 (3), 106 (9), 105 (100), 104 (7), 103 (11), 92 (10), 91 (85), 89 (3), 79 (15), 78 (6), 77 (16), 65 (17), 63 (4), 51 (7). HRMS calculated for C$_{16}$H$_{16}$ONa (M+Na$^+$): 247.10934. Found: 247.10930.

Example 31

Synthesis of (+/−)-tasimelteon

Route 1:

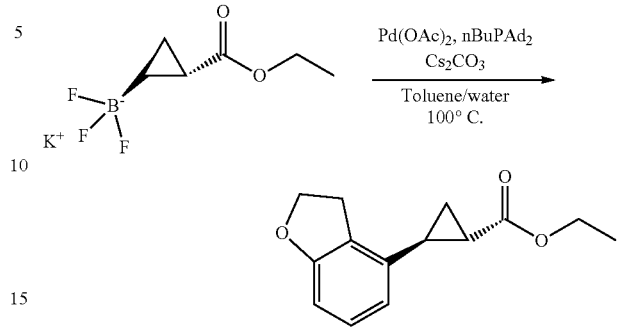

4-bromo-2,3-dihydrobenzofurane (1 g, 5.03 mmol), palladium diacetate (23 mg, 0.10 mmol) and n-butyldi-adamantylphosphine (54 mg, 0.15 mmol) are added successively to a solution of potassium trifluoroborate (Example 1, 2.21 g, 10.05 mmol) in a mixture of toluene (55 ml) and water (5.5 ml). The medium is purged with nitrogen for 10 minutes. Caesium carbonate (4.4 g, 13.56 mmol) is added and the reaction mixture is heated at 100° C. overnight. After hydrolysis with water, the aqueous phase is extracted 3 times with ethyl acetate. The combined organic phases are dried over magnesium sulphate, filtered and concentrated to dryness in order to produce 1.4 g of a brown oil. Purification by chromatography on silica gel (heptane/ethyl acetate gradient) produces 910 mg (78%) of expected compound in the form of a yellow oil.

$^1$H-NMR (CDCl$_3$, 300 MHz) δ 7.04 (dd, J=7.8 Hz, 1H), 6.65 (d, J=8.1 Hz, 1H), 6.40 (d, J=7.8 Hz, 1H), 4.60 (t, J=8.7 Hz, 2H), 4.18 (q, 7.1 Hz, 2H), 3.24 (t, J=8.7 Hz, 2H), 2.42 (m, 1H), 1.90 (m, 1H), 1.58 (m, 1H), 1.30 (m, 4H). $^{13}$C-NMR (CDCl$_3$, 300 MHz): 174.0, 160.2, 137.1, 128.7, 127.0, 116.5, 107.9, 71.5, 61.2, 29.0, 24.4, 23.3, 16.6, 14.7

LCUV>99%.

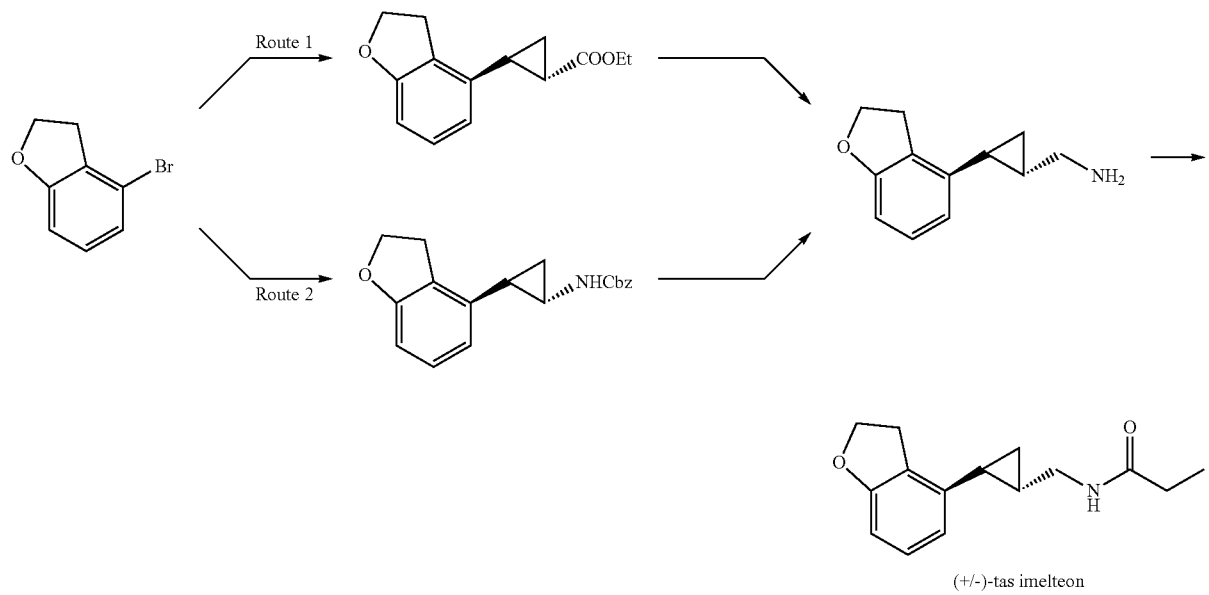

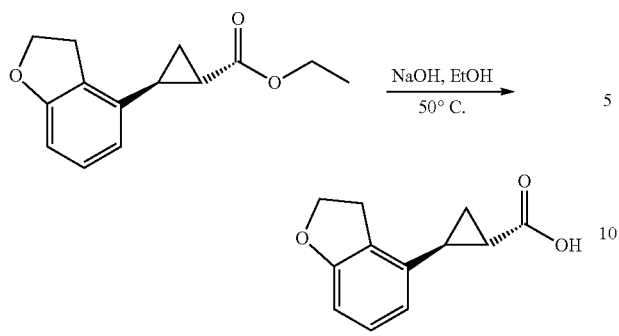

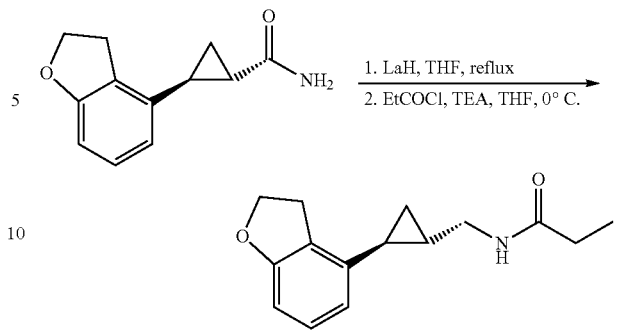

A solution of ethyl ester (800 mg, 3.4 mmol) in a 2 N aqueous soda mixture (8.6 ml, 17.3 mmol) and ethanol (4 ml) is heated at 50° C. for 2 h. 1 N hydrochloric acid is then added, then the aqueous phase is extracted 3 times with ethyl acetate. The combined organic phases are washed with water then with salt water, dried over magnesium sulphate, filtered and concentrated to dryness in order to produce 680 mg of a beige solid (98%).

mp=146° C.

$^1$H-NMR (CDCl$_3$, 300 MHz) δ 7.04 (dd, J=7.8 Hz, 1H), 6.65 (d, J=7.8 Hz, 1H), 6.41 (d, J=7.8 Hz, 1H), 4.60 (t, J=8.7 Hz, 2H), 3.25 (t, J=8.7 Hz, 2H), 2.49 (m, 1H), 1.89 (m, 1H), 1.62 (m, 1H), 1.40 (m, 1H).

$^{13}$C-NMR (CDCl$_3$, 300 MHz) 180.1, 160.3, 136.5, 128.8, 127.1, 116.8, 108.2, 77.5, 29.0, 25.3, 23.0, 17.0

LC/MS>99%, m/z [M+H]$^+$=205.2.

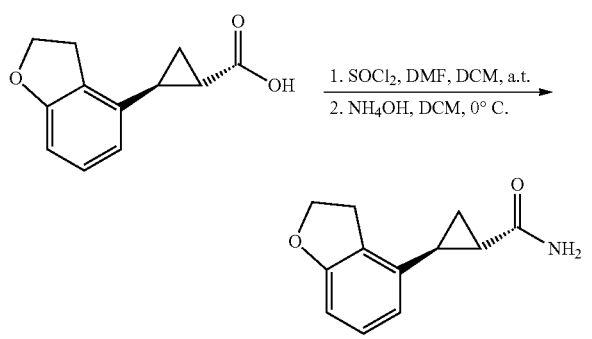

Dimethylformamide (100 μl) and thionyl chloride (500 μl, 6.8 mmol) are added to a solution of carboxylic acid (680 mg, 3.3 mmol) in 6.8 ml of dichloromethane at ambient temperature. After 2 hours, the reaction mixture is concentrated to dryness, then taken up in 3.4 ml of dichloromethane. The medium is cooled down to 0° C. in an ice/water bath, then ammonia (13.6 ml) is added slowly. The observed suspension is stirred overnight at ambient temperature. Isopropyl ether is added, the solid is filtered then washed two times with isopropyl ether in order to produce 565 mg (83%) of expected compound in the form of a white solid.

mp=194° C.

$^1$H-NMR (CDCl$_3$, 300 MHz) δ 7.05 (dd, J=7.8 Hz, 1H), 6.68 (d, J=7.8 Hz, 1H), 6.38 (d, J=7.8 Hz, 1H), 5.72 (s, 1H), 5.58 (s, 1H), 4.60 (t, J=8.7 Hz, 2H), 3.26 (m, 2H), 2.44 (m, 1H), 1.83 (m, 1H), 1.63 (m, 1H), 1.30 (m, 1H). $^{13}$C-NMR (CDCl$_3$, 300 MHz) 174.9, 160.2, 137.5, 128.7, 127.0, 115.9, 107.9, 77.6, 29.0, 25.0, 23.8, 16.2

LC/MS>99%, m/z [M+H]$^+$=204.2.

The amide (300 mg, 1.48 mmol) is added by portions to a suspension of LAH (196 mg, 5.17 mmol) in tetrahydrofuran (3 ml) at ambient temperature and under an inert atmosphere, then the medium is heated at reflux for 3 hours and at ambient temperature overnight. Water (200 μl), 6 N aqueous soda (200 μl), then again water (6000 are added to the medium at 0° C. The suspension obtained is filtered on celite and the filtrate is evaporated to dryness. The yellow oil obtained is taken up in 6 ml of tetrahydrofuran, then triethylamine (1 ml, 7.38 mmol) is added to the mixture. Propionyl chloride (410 mg, 4.43 mmol) is added dropwise to the mixture cooled down to 0° C. The medium is stirred for 1 h at 0° C. then for 2 h at ambient temperature. Water and dichloromethane are added, then the phases are separated. The aqueous phase is extracted 3 times with dichloromethane. The combined organic phases are washed with water, with salt water, then dried over magnesium sulphate, filtered and concentrated to dryness in order to produce a yellow oil purified by chromatography on silica gel (heptane/ethyl acetate gradient). The expected product is obtained in the form of a yellow oil.

$^1$H-NMR (CDCl$_3$, 300 MHz) δ 7.04 (dd, J=7.8 Hz, 1H), 6.63 (d, J=7.8 Hz, 1H), 6.35 (d, J=7.8 Hz, 1H), 5.64 (s, 1H), 4.61 (t, J=8.7 Hz, 2H), 3.29 (m, 4H), 2.24 (q, J=7.5 Hz, 2H), 1.75 (m, 1H), 1.25 (m, 1H), 1.17 (t, J=7.5 Hz, 3H), 0.96 (m, 2H).

$^{13}$C-NMR (CDCl$_3$, 300 MHz) 174.2, 160.0, 139.3, 128.6, 126.4, 116.0, 107.2, 71.5, 44.0, 30.2, 29.0, 22.1, 20.1, 13.9, 10.3.

LC/MS>97%, m/z [M+H]$^+$=246.2.

Route 2:

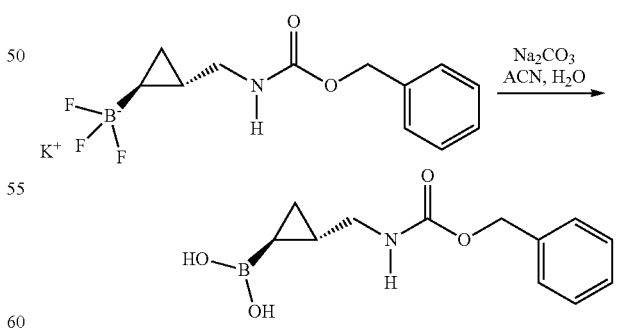

Sodium carbonate (373 mg, 3.52 mmol) is added to a solution of potassium trifluoroborate (Example 9, 730 mg, 2.35 mmol) in an acetonitrile (23.4 ml)/water (11.7 ml) mixture. The medium is stirred for 1 h at ambient temperature. A saturated aqueous solution of ammonium chloride is added until a pH close to 6 is obtained then the medium is extracted 4 times with isopropyl ether. The organic phases are washed with water then dried over magnesium sulphate, filtered and concentrated to dryness in order to produce a white solid (530 mg, yield 91%).

$^1$H-NMR (MeOD, 300 MHz) δ 7.33 (m, 5H), 5.06 (s, 2H), 3.02 (m, 2H), 1.12 (m, 1H), 0.63 (m, 1H), 0.48 (m, 1H), −0.17 (m, 1H).

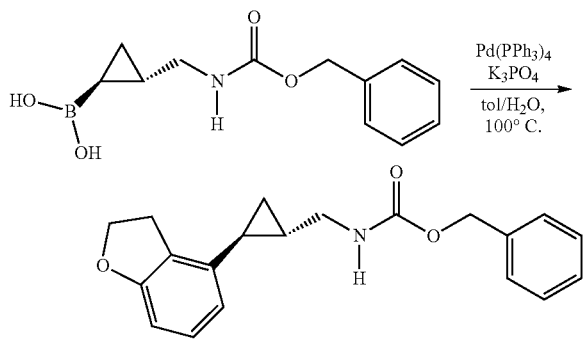

Boronic acid (530 mg, 2.13 mmol) is solubilized in a mixture of toluene (10.6 ml) and water (2.6 ml). Brominated dihydrobenzofuran (848 mg, 4.26 mmol) and palladium-tetrakis (123 mg, 0.11 mmol) are added. The medium is stirred whilst under vacuum, then under nitrogen 3 times. Potassium phosphate (1.4 g, 6.39 mmol) is added, then the medium is heated at 100° C. overnight under nitrogen. Water is added and the expected product is extracted 3 times with ethyl acetate. The combined organic phases are washed with water then with salt water, and they are dried over magnesium sulphate, filtered and concentrated in order to produce 1.2 g of a brown oil. The expected product is purified by chromatography on silica gel (heptane/ethyl acetate gradient) and it is obtained in the form of a yellow oil (413 mg, yield 60%). $^1$H-NMR (CDCl3, 300 MHz) δ 7.29 (m, 5H), 6.94 (dd, J=8.1 Hz, 1H), 6.54 (d, J=7.8 Hz, 1H), 6.26 (d, J=7.8 Hz, 1H), 5.08 (s, 2H), 4.85 (s, 1H), 4.48 (t, J=8.7 Hz, 2H), 3.16 (m, 4H), 1.66 (m, 1H), 1.23 (m, 1H), 0.90 (m, 1H), 0.81 (m, 1H).

$^{13}$C-NMR (CDCl$_3$, 300 MHz) 160.0, 156.8, 139.2, 136.9, 129.0, 128.6, 126.5, 116.2, 107.2, 71.4, 67.1, 45.6, 29.0, 22.5, 19.9, 13.5.

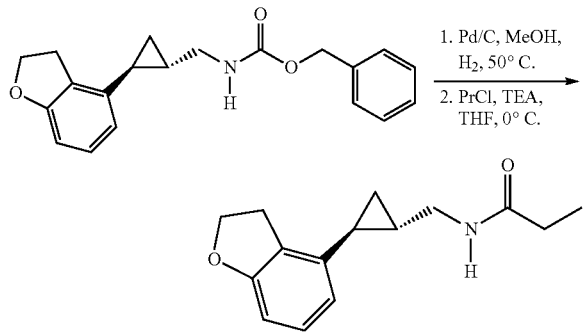

Palladium on carbon (38 mg) is added to a solution of carbamate (380 mg, 1.17 mmol) in methanol (7.6 ml), degassed 3 times by vacuum/nitrogen purges. The medium is again purged 3 times with nitrogen then placed under a hydrogen atmosphere. The mixture is heated at 50° C. overnight under hydrogen. The suspension obtained is filtered on celite then the filtrate is evaporated to dryness. The yellow oil obtained is taken up in 5 ml of tetrahydrofuran, then triethylamine (819 μl, 5.85 mmol) is added to the mixture. Propionyl chloride (308 μl, 3.51 mmol) is added dropwise to the mixture cooled down to 0° C. The medium is stirred for 1 h at 0° C. then for 1 h 30 at ambient temperature. Water and dichloromethane are added, then the phases are separated. The aqueous phase is extracted 3 times with dichloromethane. The combined organic phases are washed with water, with salt water, then dried over magnesium sulphate, filtered and concentrated to dryness in order to produce a yellow oil purified by chromatography on silica gel (heptane/ethyl acetate gradient). The expected product is obtained in the form of a yellow oil.

$^1$H-NMR (CDCl$_3$, 300 MHz) δ 7.04 (dd, J=7.8 Hz, 1H), 6.63 (d, J=7.8 Hz, 1H), 6.35 (d, J=7.8 Hz, 1H), 5.64 (s, 1H), 4.61 (t, J=8.7 Hz, 2H), 3.29 (m, 4H), 2.24 (q, J=7.5 Hz, 2H), 1.75 (m, 1H), 1.25 (m, 1H), 1.17 (t, J=7.5 Hz, 3H), 0.96 (m, 2H).

$^{13}$C-NMR (CDCl$_3$, 300 MHz) 174.2, 160.0, 139.3, 128.6, 126.4, 116.0, 107.2, 71.5, 44.0, 30.2, 29.0, 22.1, 20.1, 13.9, 10.3.

The invention claimed is:

1. Process for the preparation of a compound corresponding to the following formula (I-A)

(I-A)

in which:
X represents a substituted boron atom selected from the group consisting of B(OH)$_2$, B(OR)$_2$, BF$_3$M, and B(OR')$_3$M, in which:
R is an alkyl group comprising 1 to 14 carbon atoms or an aryl group, optionally substituted, or is such that (OR)$_2$ forms a ring between the two oxygen atoms,
R' is an alkyl group comprising 1 to 14 carbon atoms or is such that:
(OR')$_3$ forms a ring between two of the oxygen atoms, (OR')$_3$ then being in the form OR'(OR)$_2$, where R' is an alkyl group comprising 1 to 14 carbon atoms and (OR)$_2$ is as defined above, or
(OR')$_3$ forms a bicycle between the three oxygen atoms,
M represents the lithium Li$^+$ ion, the sodium Na$^+$ ion, the potassium K$^+$ ion, the caesium Cs$^+$ ion, the ammonium R$^c$R$^d$R$^e$R$^f$N$^+$ ion where R$^c$, R$^d$ R$^e$, R$^f$ are H or a saturated carbon-containing chain,
R$_1$ and R$_4$, identical or different, are selected from the group consisting of:
(i) H;
(ii) the aryls comprising rings with 6 to 15 carbon atoms, optionally substituted by:
one or more halogen atoms comprising fluorine, chlorine, bromine or iodine,
hydroxy, amino or thio radicals optionally protected by "ad hoc" protective groups,
—OR$^a$, —NHR$^a$, —NR$^a$R$^b$, —SR$^a$, —OCOR$^a$, —OCONHR$^a$, —OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N—(C=NCOR$^a$)NHCOR$^b$, —N(C=NCOOR$^a$)NHCOOR$^b$ radicals,
alkyl radicals with 1 to 15 carbon atoms, optionally substituted,
alkenyl radicals with 1 to 15 carbon atoms, optionally substituted,
alkynyl radicals with 1 to 15 carbon atoms, optionally substituted,
aryls with 6 to 12 carbon atoms, optionally substituted,
aromatic or non-aromatic heterocycles with 2 to 12 carbon atoms, optionally substituted,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted by:
one or more halogen atoms comprising fluorine, chlorine, bromine or iodine,
hydroxy, amino or thio radicals optionally protected by "ad hoc" protective groups,
—OR$^a$, —NHR$^a$, —NR$^a$R$^b$, —SR$^a$, —OCOR$^a$, —OCONHR$^a$, —OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N—(C=NCOR$^a$)NHCOR$^b$, —N(C=NCOOR$^a$)NHCOOR$^b$ radicals,
in which R$^a$ and R$^b$, identical or different, represent linear or branched, aromatic, or aromatic or non-aromatic heterocyclic alkyl, alkenyl, alkynyl groups comprising 1 to 15 carbon atoms,
alkyl radicals comprising 1 to 15 carbon atoms, linear or branched optionally substituted,
by the linear or branched alkenyl radicals comprising 1 to 15 carbon atoms, optionally substituted,
by the alkynyl radicals comprising 1 to 15 carbon atoms, linear or branched optionally substituted,
by the aryls with 6 to 12 carbon atoms, optionally substituted,
by the aromatic or non-aromatic heterocycles comprising 2 to 12 carbon atoms, optionally substituted;
(iii) the heterocycles or heteroaryls comprising rings with 2 to 15 carbon atoms, optionally substituted by:
one or more halogen atoms comprising fluorine, chlorine, bromine or iodine,
by the hydroxy, amino or thio radicals optionally protected by "ad hoc" protective groups,
—OR$^a$, —NHR$^a$, —NR$^a$R$^b$, —SR$^a$, —OCOR$^a$, —OCONHR$^a$, —OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N—(C=NCOR$^a$)NHCOR$^b$, —N(C=NCOOR$^a$)NHCOOR$^b$ radicals,
by the alkyl radicals comprising 1 to 15 carbon atoms, optionally substituted,
by the linear or branched alkenyl radicals comprising 1 to 15 carbon atoms, optionally substituted,
by the linear or branched alkynyl radicals comprising 1 to 15 carbon atoms, optionally substituted,
by the linear or branched aryl radicals comprising 6 to 12 carbon atoms, optionally substituted,
by the aromatic or non-aromatic heterocycles comprising 2 to 12 carbon atoms, optionally substituted, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted by:
one or more halogen atoms comprising fluorine, chlorine, bromine or iodine,
hydroxy, amino or thio radicals optionally protected by "ad hoc" protective groups,
—OR$^a$, —NHR$^a$, —NR$^a$R$^b$, —SR$^a$, —OCOR$^a$, —OCONHR$^a$, —OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N—(C=NCOR$^a$)NHCOR$^b$, —N(C=NCOOR$^a$)NHCOOR$^b$ radicals,
in which R$^a$ and R$^b$, identical or different, represent linear or branched, aromatic, or aromatic or non-aromatic heterocyclic alkyls, alkenyl, alkynyls groups comprising 1 to 15 carbon atoms,
alkyl radicals comprising 1 to 15 carbon atoms, optionally substituted,
linear or branched alkenyl radicals comprising 1 to 15 carbon atoms, optionally substituted,
linear or branched alkynyl radicals comprising 1 to 15 carbon atoms, optionally substituted,
linear or branched aryl radicals comprising 6 to 12 carbon atoms, optionally substituted,
aromatic or non-aromatic heterocycles comprising 2 to 12 carbon atoms, optionally substituted;
(iv) the linear or branched alkenyls comprising 1 to 12 carbon atoms, optionally substituted, or carbon rings comprising 3 to 12 carbon atoms and one or more C=C double bonds, optionally substituted by:
one or more halogen atoms comprising fluorine, chlorine, bromine or iodine,
by the hydroxy, amino or thio radicals optionally protected by "ad hoc" protective groups,
—OR$^a$, —NHR$^a$, —NR$^a$R$^b$, —SR$^a$, —OCOR$^a$, —OCONHR$^a$, —OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N—(C=NCOR$^a$)NHCOR$^b$, —N(C=NCOOR$^a$)NHCOOR$^b$ radicals,
by the alkyl radicals comprising 1 to 15 carbon atoms, optionally substituted,
by the linear or branched alkenyl radicals comprising 1 to 15 carbon atoms, optionally substituted,
by the linear or branched alkynyl radicals comprising 1 to 15 carbon atoms, optionally substituted,
by the linear or branched aryl radicals comprising 6 to 12 carbon atoms, optionally substituted,
by the aromatic or non-aromatic heterocycles comprising 2 to 12 carbon atoms, optionally substituted,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted by:
one or more halogen atoms comprising fluorine, chlorine, bromine or iodine,
by the hydroxy, amino or thio radicals optionally protected by "ad hoc" protective groups, —OR$^a$, —NHR$^a$, —NR$^a$R$^b$, —SR$^a$, —OCOR$^a$, —OCONHR$^a$, —OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N(C=NCOR$^a$)NHCOR$^b$, —N(C=NCOOR$^a$)NHCOOR$^b$ radicals, in which R$^a$ and R$^b$, identical or different, represent linear or branched, aromatic, or aromatic or non-aromatic heterocyclic alkyl, alkenyl, alkynyl, groups comprising 1 to 15 carbon atoms, by the alkyl radicals comprising 1 to 15 carbon atoms, optionally substituted, by the linear or branched alkenyl radicals comprising 1 to 15 carbon atoms, optionally substituted, by the linear or branched alkynyl radicals comprising 1 to 15 carbon atoms, optionally substituted, by the linear or branched aryl radicals comprising 6 to 12 carbon atoms, optionally substituted, by the aromatic or non-aromatic heterocycles comprising 2 to 12 carbon atoms, optionally substituted;

(v) the linear or branched alkynyls comprising 1 to 15 carbon atoms, optionally substituted by:

one or more halogen atoms comprising fluorine, chlorine, bromine or iodine, by the hydroxy, amino or thio radicals optionally protected by "ad hoc" protective groups, —OR$^a$, —NHR$^a$, —NR$^a$R$^b$, —SR$^a$, —OCOR$^a$, —OCONHR$^a$, —OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N(C=NCOR$^a$)NHCOR$^b$, —N(C=NCOOR$^a$)NHCOOR$^b$ radicals, by the alkyl radicals comprising 1 to 15 carbon atoms, optionally substituted, by the linear or branched alkenyl radicals comprising 1 to 15 carbon atoms, optionally substituted, by the linear or branched alkynyl radicals comprising 1 to 15 carbon atoms, optionally substituted, by the linear or branched aryl radicals comprising 6 to 12 carbon atoms, optionally substituted, by the aromatic or non-aromatic heterocycles comprising 2 to 12 carbon atoms, optionally substituted, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted by:

one or more halogen atoms comprising fluorine, chlorine, bromine or iodine, hydroxy, amino or thio radicals optionally protected by "ad hoc" protective groups, —OR$^a$, —NHR$^a$, —NR$^a$R$^b$, —SR$^a$, —OCOR$^a$, —OCONHR$^a$, —OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N(C=NCOR$^a$)NHCOR$^b$, —N(C=NCOOR$^a$)NHCOOR$^b$ radicals, in which R$^a$ and R$^b$, identical or different, represent linear or branched, aromatic, or aromatic or non-aromatic heterocyclic alkyl, alkenyl, alkynyl groups comprising 1 to 15 carbon atoms, alkyl radicals comprising 1 to 15 carbon atoms, optionally substituted, linear or branched alkenyl radicals comprising 1 to 15 carbon atoms, optionally substituted, linear or branched alkynyl radicals comprising 1 to 15 carbon atoms, optionally substituted, linear or branched aryl radicals comprising 6 to 12 carbon atoms, optionally substituted, aromatic or non-aromatic heterocycles comprising 2 to 12 carbon atoms, optionally substituted;

(vi) linear, cyclic or branched alkyl groups comprising 1 to 15 carbon atoms, optionally substituted by:

one or more halogen atoms comprising fluorine, chlorine, bromine or iodine, hydroxy, amino or thio radicals optionally protected by "ad hoc" protective groups, —OR$^a$, —NHR$^a$, —NR$^a$R$^b$, —SR$^a$, —OCOR$^a$, —OCONHR$^a$, —OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N(C=NCOR$^a$)NHCOR$^b$, —N(C=NCOOR$^a$)NHCOOR$^b$ radicals, alkyl radicals comprising 1 to 15 carbon atoms, optionally substituted, linear or branched alkenyl radicals comprising 1 to 15 carbon atoms, optionally substituted, linear or branched alkynyl radicals comprising 1 to 15 carbon atoms, optionally substituted, linear or branched aryl radicals comprising 6 to 12 carbon atoms, optionally substituted, aromatic or non-aromatic heterocycles comprising 2 to 12 carbon atoms, optionally substituted, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted by:

one or more halogen atoms comprising fluorine, chlorine, bromine or iodine, hydroxy, amino or thio radicals optionally protected by "ad hoc" protective groups, —OR$^a$, —NHR$^a$, —NR$^a$R$^b$, —SR$^a$, —OCOR$^a$, —OCONHR$^a$, OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N(C=NCOR$^a$)NHCOR$^b$, —N(C=NCOOR$^a$)NHCOOR$^b$ radicals, in which R$^a$ and R$^b$, identical or different, represent linear or branched, aromatic, or aromatic or non-aromatic heterocyclic alkyl, alkenyl, alkynyl groups comprising 1 to 15 carbon atoms, alkyl radicals comprising 1 to 15 carbon atoms, optionally substituted, linear or branched alkenyl radicals comprising 1 to 15 carbon atoms, optionally substituted, linear or branched alkynyl radicals comprising 1 to 15 carbon atoms, optionally substituted, linear or branched aryl radicals comprising 6 to 12 carbon atoms, optionally substituted, aromatic or non-aromatic heterocycles comprising 2 to 12 carbon atoms, optionally substituted, at least one of the R$_1$ and R$_4$ groups representing H;

$R_2$ is selected from the group consisting of the groups represented by $R_1$ or $R_4$ as defined above, —COR$^a$, —COOR$^a$, —CONH$_2$, —CONHR$^a$, —CONR$^a$R$^b$, —CN and —NO$_2$, in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted by:

one or more halogen atoms comprising fluorine, chlorine, bromine or iodine, hydroxy, amino or thio radicals optionally protected by "ad hoc" protective groups, —OR$^a$, —NHR$^a$, —NR$^a$R$^b$, —SR$^a$, —OCOR$^a$, —OCONHR$^a$, —OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N(C=NCOR$^a$)NHCOR$^b$, —N(C=NCOOR$^a$)NHCOOR$^b$ radicals, in which R$^a$ and R$^b$, identical or different, represent linear or branched, aromatic, or aromatic or non-aromatic heterocyclic alkyl, alkenyl, alkynyl groups comprising 1 to 15 carbon atoms, alkyl radicals comprising 1 to 15 carbon atoms, optionally substituted, linear or branched alkenyl radicals comprising 1 to 15 carbon atoms, optionally substituted, linear or branched alkynyl radicals comprising 1 to 15 carbon atoms, optionally substituted, linear or branched aryl radicals comprising 6 to 12 carbon atoms, optionally substituted, aromatic or non-aromatic heterocycles comprising 2 to 12 carbon atoms, optionally substituted, R$^a$ and R$^b$ being able to be linked in order to form a ring, optionally substituted;

W represents a functional group selected from the group consisting of —CHO, —COR$^a$, —COOH, —COOR$^a$, —CONH$_2$, —CONHR$^a$, —CONR$^a$R$^b$, —CONH—SO$_2$—R$^a$, —CH$_2$OH, —CH$_2$OR$^a$, —CHR$^b$OH, —CHR$^b$OR$^a$, —CR$^b$R$^b$' OH, —CR$^b$R$^b$'OR$^a$, —CH$_2$NH$_2$, —CH$_2$NHZ, —CHR$^a$NHZ, and —CH$_2$—NH—COR$^a$, in which Z represents a protective group of an amine function, and in which R$^a$, R$^b$ and R$^b'$, identical or different, represent linear, cyclic or branched, aromatic, or aromatic or non-aromatic heterocyclic alkyl, alkenyl, alkynyl groups comprising 1 to 15 carbon atoms, optionally substituted by:

one or more halogen atoms comprising fluorine, chlorine, bromine or iodine, hydroxy, amino or thio radicals optionally protected by "ad hoc" protective groups, —OR$^a$, —NHR$^a$, —NR$^a$R$^b$, —SR$^a$, —OCOR$^a$, —OCONHR$^a$, —OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N(C=NCOR$^a$)NHCOR$^b$, —N(C=NCOOR$^a$)NHCOOR$^b$ radicals, in which R$^a$ and R$^b$, identical or different, represent linear or branched, aromatic, or aromatic or non-aromatic heterocyclic alkyl, alkenyl, alkynyl groups comprising 1 to 15 carbon atoms, alkyl radicals comprising 1 to 15 carbon atoms, optionally substituted, linear or branched alkenyl radicals comprising 1 to 15 carbon atoms, optionally substituted, linear or branched alkynyl radicals comprising 1 to 15 carbon atoms, optionally substituted, linear or branched aryl radicals comprising 6 to 12 carbon atoms, optionally substituted, aromatic or non-aromatic heterocycles comprising 2 to 12 carbon atoms, optionally substituted, said process comprising:

a step of reaction between:

a diazoic derivative of the following formula:

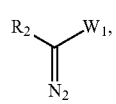

in which $R_2$ is as defined above, $W_1$ being chosen from the group consisting of —COR$^a$, —COOR$^a$, —CONH$_2$, —CONHR$^a$, and —CONR$^a$R$^b$, and a vinyltrifluoroborate compound of the following formula:

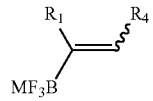

in which $R_1$, $R_4$ and M are as defined above, in the presence of a catalyst containing a transition metal, in order to obtain a compound of the following formula:

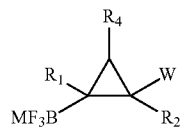

in which $R_1$, $R_2$, $R_4$, $W_1$ and M are as defined above;

wherein if W is different from $W_1$ and/or X is different from MF$_3$B, said process also comprising the following steps:

a step of conversion of $W_1$ to W making it possible to obtain

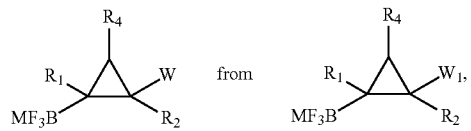

and when $W_1$=COOR$^a$ and W=CHO, by reduction in order to form the corresponding alcohol, then oxidation of said alcohol, when $W_1$=—COOR$^a$ and W=CH$_2$OH or —CH$_2$OR$^b$, by the formation of an aldehyde as described previously, then by reduction of said aldehyde and optional alkylation, when $W_1$=—$COR^a$ and W=—$CHR^aOH$, —$CHR^aOR^b$, by reduction then optional alkylation of the alcohol obtained, when $W_1$=—$COR^a$ and W=$CR^aR^bOH$ or —$CR^aR^bOR^{b'}$ by addition of a Grignard reagent then optional alkylation of the alcohol obtained, when $W_1$=—$CONH_2$, —$CONHR^a$ or —$CONR^aR^b$ and W=—$CH_2NH_2$, —$CH_2NHR^a$, —$CH_2NR^aR^b$, —$CH_2NHZ$ or —$CH_2$—NH—$COR^a$, by reduction then optional protection by Z of the amine obtained or optional reaction with the acid chloride $R^aCOCl$, and when $W_1$=—$CONH_2$ and W=—$CONHSO_2R^a$, by the action of sulphonyl chloride $ClSO_2R^a$ on the amide, and a step of conversion of —$BF_3M$ to —X making it possible to obtain

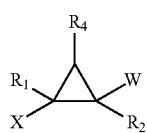 from 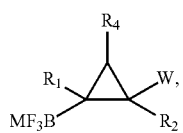

and when X=$B(OH)_2$, by basic or acid hydrolysis, or by passing via a dihalogenoborane, when X=$B(OR)_2$, by passing via X=$B(OH)_2$ as described previously then by the action of an alcohol, or by passing via a dihalogenoborane, then by the action of an alcohol, or a step of conversion of —$BF_3M$ to —X making it possible to obtain

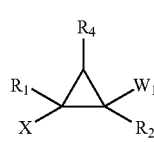 from 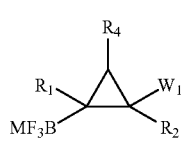

and a step of conversion of $W_1$ to W making it possible to obtain

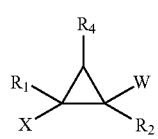 from 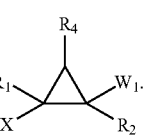

2. The process according to claim 1, in which said catalyst containing a transition metal comprises a palladium (II) complex, $Pd(OAc)_2$, $Pd(acac)_2$, a copper (II) complex, $CuSO_4$, $Cu(acac)_2$, $Cu(tBuSalen)_2$, $Cu(OTf)_2$, a copper (I) complex, CuI, Cu(OTf), a rhodium (II) complex, $Rh_2(OAc)_4$, $Rh_2(Octanoate)_4$ or $Rh_2(5S-MEPY)_4$ (Doyle catalyst).

3. The process according to claim 1, in which $W_1$ represents —$COOR^a$, $R^a$ being as defined previously, said process comprising:

a step of reaction between:
a diazoic derivative of the following formula:

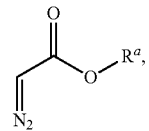

in which $R^a$ is as defined previously, and
a vinyltrifluoroborate compound of the following formula:

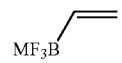

in which M is as defined previously,
in the presence of a catalyst containing a transition metal, in order to obtain a compound of the following formula:

in which $R^a$ and M are as defined above,
wherein if W is different from —$COOR^a$ and/or X is different from $MF_3B$, said process also comprising the following steps:
a step of conversion of —$COOR^a$ to W making it possible to obtain

and
a step of conversion of —$BF_3M$ to —X making it possible to obtain

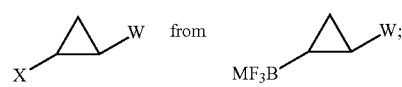

or
a step of conversion of —$BF_3M$ to —X making it possible to obtain

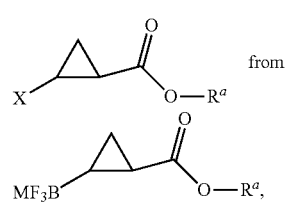

and
a step of conversion of —COOR$^a$ to W making it possible to obtain

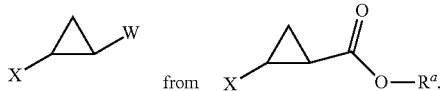

4. The process according to claim 1, in which:
R$_2$ is selected from the group consisting of —COR$^a$, —COOR$^a$, —CONH$_2$, —CONHR$^a$, —CONR$^a$R$^b$, —CN and —NO$_2$,
in which R$^a$ and R$^b$, identical or different, represent linear, cyclic or branched, aromatic, or aromatic or non-aromatic heterocyclic alkyl, alkenyl, alkynyl groups comprising 1 to 15 carbon atoms, optionally substituted by:
one or more halogen atoms comprising fluorine, chlorine, bromine or iodine,
hydroxy, amino or thio radicals optionally protected by "ad hoc" protective groups,
—OR$^a$, —NHR$^a$, —NR$^a$R$^b$, —SR$^a$, —OCOR$^a$, —OCONHR$^a$, —OCONR$^a$R$^b$, —CHO, —COR$^a$, —COOH, —CN, —COOR$^a$, —CONHR$^a$, —CONR$^a$R$^b$, —CF$_3$, —NO$_2$, —N=C—NHR$^a$, —N=C—NR$^a$R$^b$, —N=C—NH$_2$, —N=C—NHCOR$^a$, —N=C—NH—COOR$^a$, —N(C=NH)NH$_2$, —N—(C=NCOR$^a$)NHCOR$^b$, —N(C=NCOOR$^a$)NHCOOR$^b$ radicals,
in which R$^a$ and R$^b$, identical or different, represent linear or branched, aromatic, or aromatic or non-aromatic heterocyclic alkyl, alkenyl, alkynyl groups comprising 1 to 15 carbon atoms,
alkyl radicals comprising 1 to 15 carbon atoms, optionally substituted,
linear or branched alkenyl radicals comprising 1 to 15 carbon atoms, optionally substituted,
linear or branched alkynyl radicals comprising 1 to 15 carbon atoms, optionally substituted,
linear or branched aryl radicals comprising 6 to 12 carbon atoms, optionally substituted,
aromatic or non-aromatic heterocycles comprising 2 to 12 carbon atoms, optionally substituted,
R$^a$ and R$^b$ being able to be linked in order to form a ring, optionally substituted,
or in which R$_2$ represents H,
or in which R$_1$, R$_2$ and R$_4$ represent H,
or in which R$_1$ represents H,
or in which R$_1$ represents H and R$_4$ represents an aryl, a heterocycle, a heteroaryl or an alkyl as defined previously,
or in which R$_4$ represents H,
or in which R$_4$ represents H and R$_1$ represents an aryl, a heterocycle, a heteroaryl or an alkyl as defined previously,
or in which R$_1$ and R$_2$ represent H and R$_4$ represents an aryl, a heterocycle, a heteroaryl or an alkyl as defined previously,
or in which R$_2$ and R$_4$ represent H and R$_1$ represents an aryl, a heterocycle, a heteroaryl or an alkyl as defined previously.

5. The process according to claim 1, in which W represents a functional group chosen from the group consisting of —CONH—SO$_2$-cyclopropyl, —CH$_2$—NH—CO—CH$_2$—CH$_3$, and the group of the following formula:

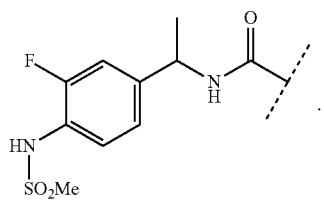

6. The process according to claim 3, in which W represents a functional group selected from the group consisting of —CONH—SO$_2$-cyclopropyl, —CH$_2$—NH—CO—CH$_2$—CH$_3$, and the group of the following formula:

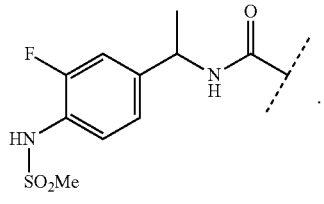

7. The process according to claim 4, in which W represents a functional group selected from the group consisting of —CONH—SO$_2$-cyclopropyl, —CH$_2$—NH—CO—CH$_2$—CH$_3$, and the group of the following formula:

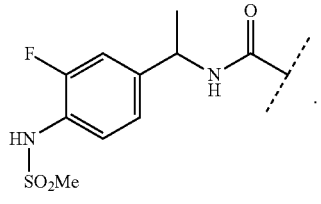

* * * * *